United States Patent
Schimmel

(10) Patent No.: US 9,630,373 B2
(45) Date of Patent: Apr. 25, 2017

(54) GAS-CONTAINING SURFACE COVER, ARRANGEMENT, AND USE

(71) Applicant: Baden-Württemberg Stiftung gGmbH, Stuttgart (DE)

(72) Inventor: Thomas Schimmel, Karlsruhe (DE)

(73) Assignee: Baden-Württemberg Stiftung gGmbH, Stuttgart (DE)

( * ) Notice: Subject to any disclaimer, the term of this patent is extended or adjusted under 35 U.S.C. 154(b) by 239 days.

(21) Appl. No.: 14/382,482

(22) PCT Filed: Feb. 22, 2013

(86) PCT No.: PCT/EP2013/000523
§ 371 (c)(1),
(2) Date: Sep. 2, 2014

(87) PCT Pub. No.: WO2013/131618
PCT Pub. Date: Sep. 12, 2013

(65) Prior Publication Data
US 2015/0273791 A1      Oct. 1, 2015

(30) Foreign Application Priority Data

Mar. 3, 2012   (DE) ................. 10 2012 004 067
Mar. 10, 2012  (DE) ................. 10 2012 004 574
(Continued)

(51) Int. Cl.
*B63B 1/38*     (2006.01)
*F16L 58/02*    (2006.01)
(Continued)

(52) U.S. Cl.
CPC .............. *B32B 3/30* (2013.01); *B05D 5/083* (2013.01); *B63B 1/38* (2013.01); *A41D 2400/24* (2013.01);
(Continued)

(58) Field of Classification Search
CPC ............... Y02T 70/122; Y02T 70/123; B63B 2001/387; B63B 1/38; F16L 57/06; F16L 58/02; A41D 2400/24
See application file for complete search history.

(56) References Cited

U.S. PATENT DOCUMENTS

| | | | | |
|---|---|---|---|---|
| 4,863,121 A | * | 9/1989 | Savill ................ | B63B 1/34 244/130 |
| 6,994,045 B2 | * | 2/2006 | Paszkowski ........ | B63B 1/38 114/67 R |
| 2010/0236466 A1 | | 9/2010 | Costas | |

FOREIGN PATENT DOCUMENTS

| EP | 0 616 940 A1 | 9/1993 |
|---|---|---|
| JP | 1991-500508 | 2/1991 |

(Continued)

OTHER PUBLICATIONS

Office Action mailed Dec. 20, 2016 for Japanese Patent Application No. 2014-559125.

*Primary Examiner* — Carson Gross
(74) *Attorney, Agent, or Firm* — McDonnell Boehnen Hulbert & Berghoff LLP

(57) ABSTRACT

An aspect of the invention relates to a surface cover for a body which can be brought into contact with a liquid, comprising: a layer which at least partly contains gas and which is designed and arranged such that at least some sections of a layer face facing the liquid contacts the liquid; a gas-permeable layer which is arranged on the gas-containing layer on a face that faces the body and is opposite the face facing the liquid or which is integrally formed with the gas-containing layer; and a gas-supplying device which is connected to the gas-permeable layer such that gas can flow from the gas-supplying device to the gas-containing layer through the gas-permeable layer. The invention also relates to an arrangement and a use.

28 Claims, 35 Drawing Sheets

(30) Foreign Application Priority Data

Mar. 17, 2012 (DE) .......................... 10 2012 005 163
Apr. 11, 2012 (DE) .......................... 10 2012 007 068

(51) Int. Cl.
*B32B 3/30* (2006.01)
*B05D 5/08* (2006.01)
*F16L 57/06* (2006.01)
*B05D 5/02* (2006.01)

(52) U.S. Cl.
CPC ............ *B05D 5/02* (2013.01); *B32B 2250/02* (2013.01); *B32B 2307/724* (2013.01); *B32B 2307/728* (2013.01); *B32B 2307/73* (2013.01); *B32B 2307/752* (2013.01); *B32B 2307/756* (2013.01); *B32B 2597/00* (2013.01); *B32B 2605/12* (2013.01); *B63B 2001/387* (2013.01); *F16L 57/06* (2013.01); *F16L 58/02* (2013.01); *Y02T 70/122* (2013.01); *Y02T 70/123* (2013.01); *Y10T 156/10* (2015.01)

(56) References Cited

FOREIGN PATENT DOCUMENTS

| | | |
|---|---|---|
| JP | 1995-017476 | 1/1995 |
| JP | 2005-048904 | 2/2005 |
| JP | 2005-507313 | 3/2005 |
| JP | 2009-247949 | 10/2009 |
| JP | 2010-155604 | 7/2010 |
| WO | WO 8911343 | 11/1989 |
| WO | 03/037702 A1 | 5/2003 |
| WO | WO 03/037702 | 5/2003 |

\* cited by examiner

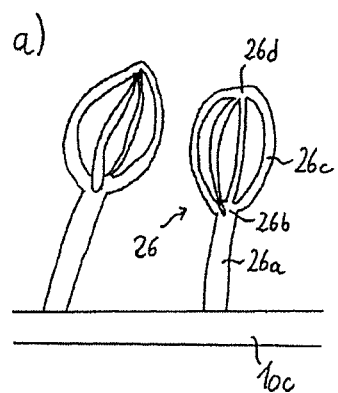
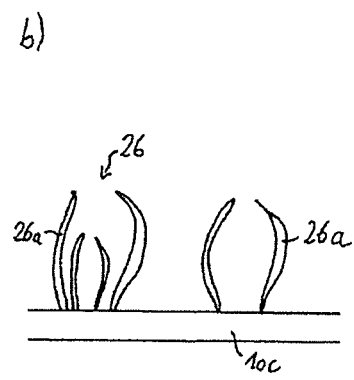
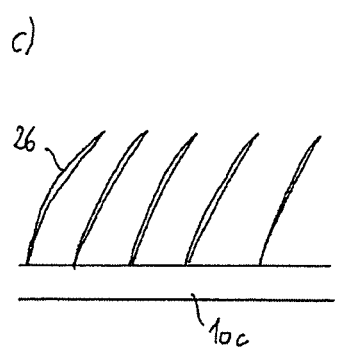
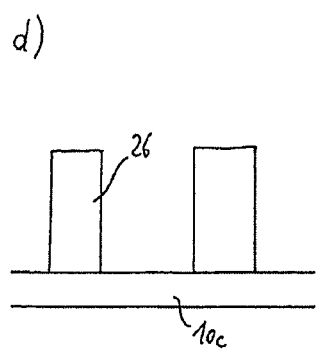
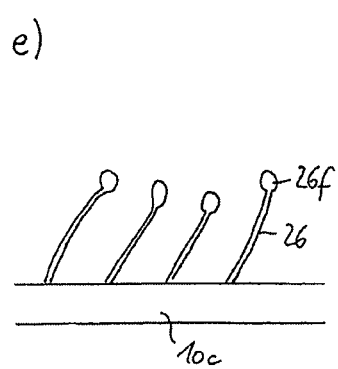
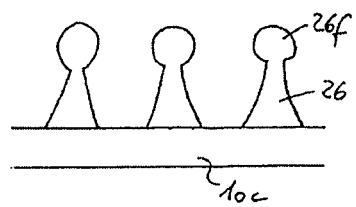
Fig. 3

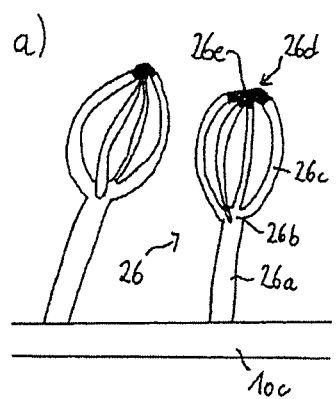
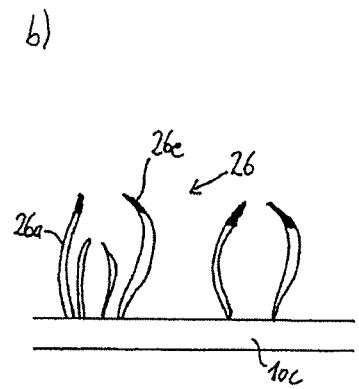
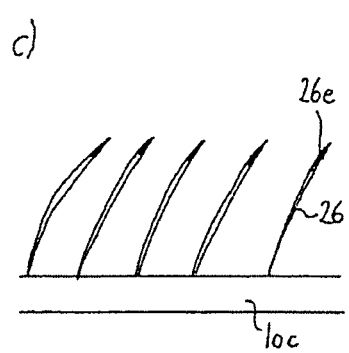
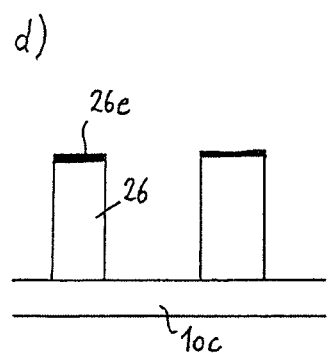
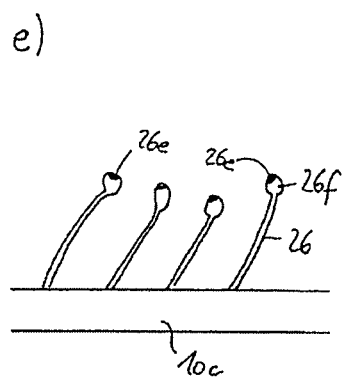
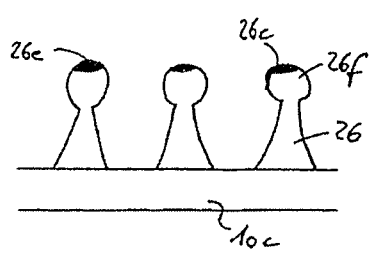
Fig. 4 a)
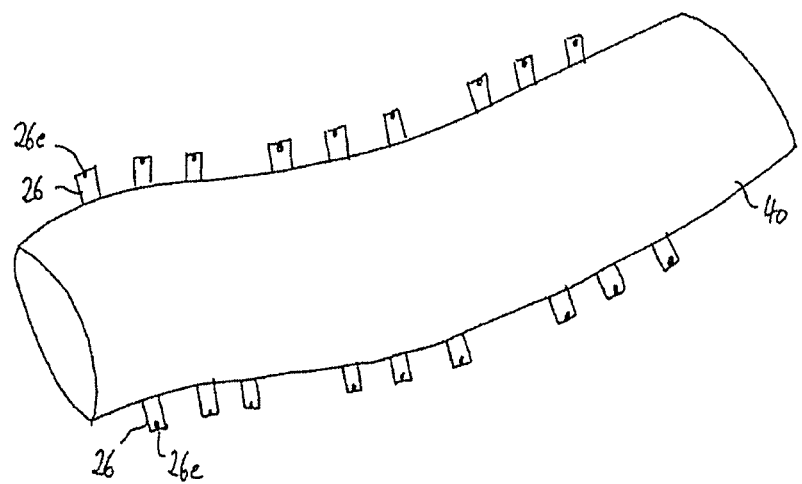
b)
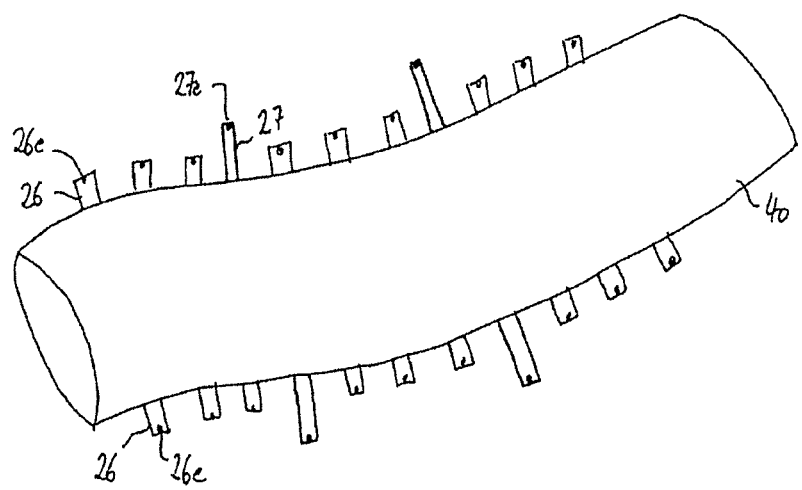
Fig. 13

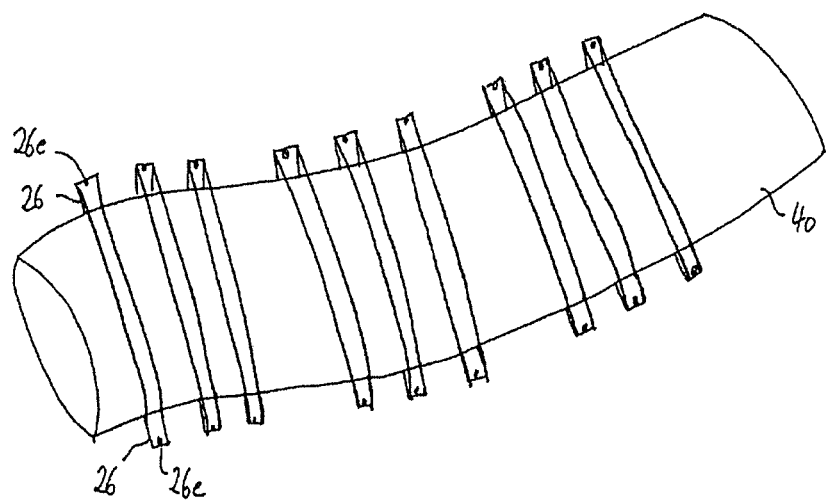
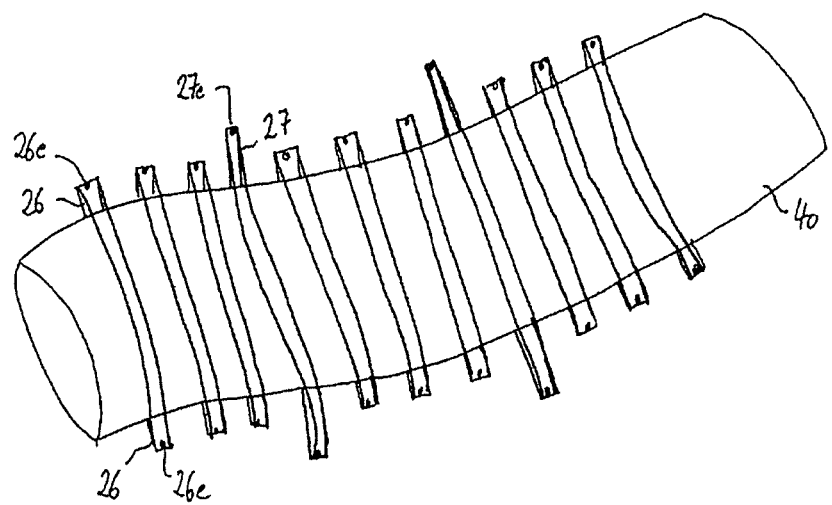
Fig. 14

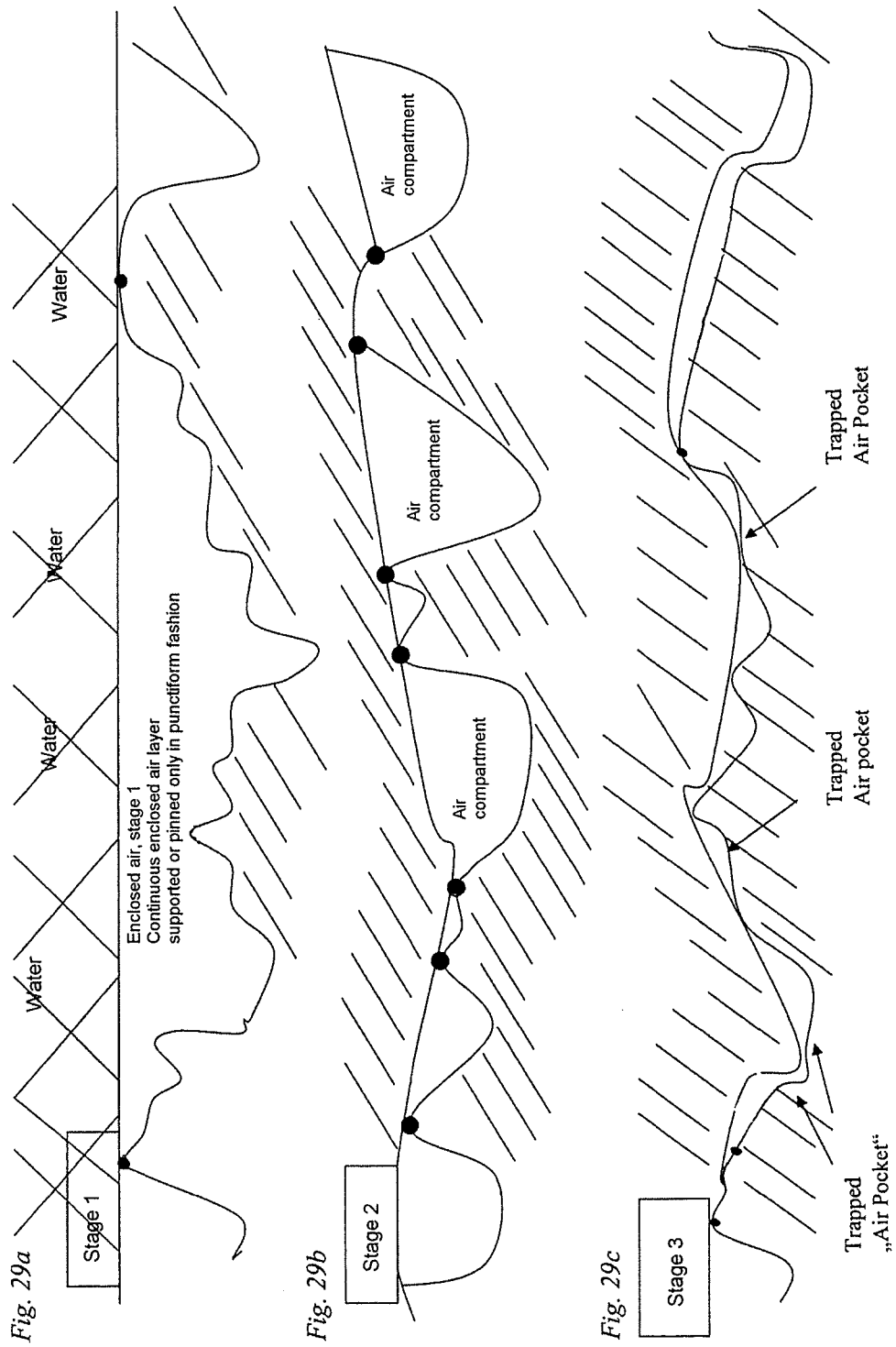

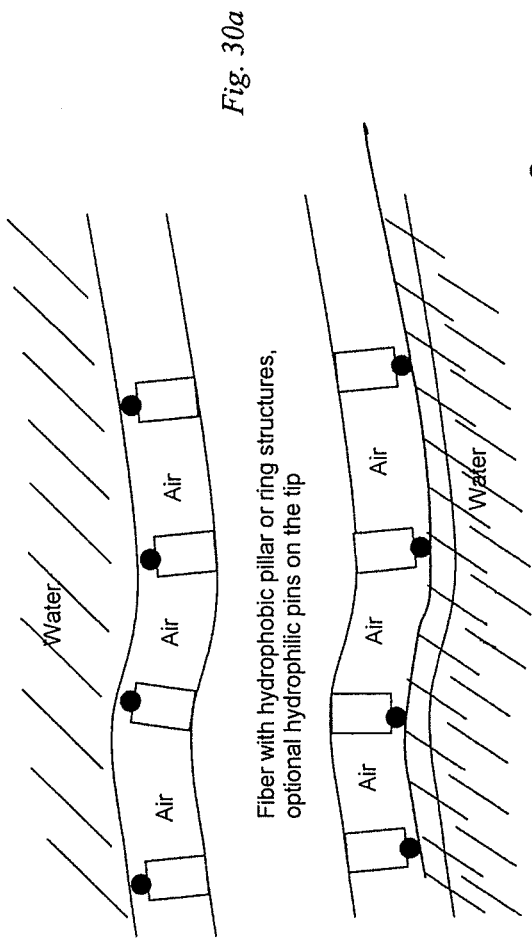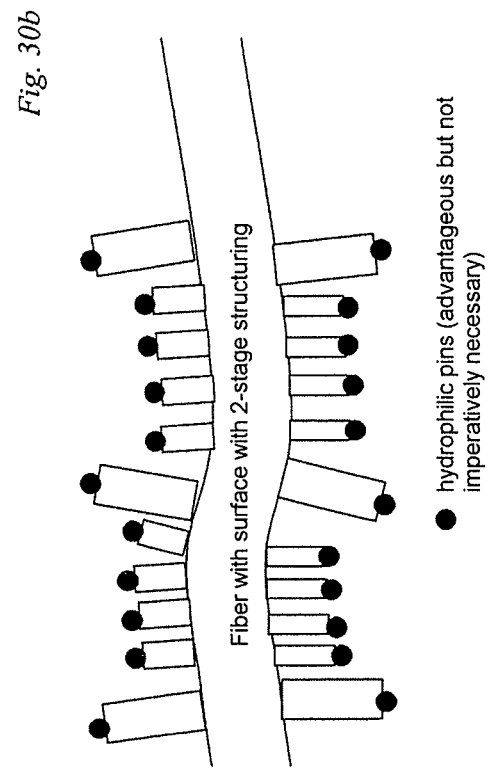

GAS-CONTAINING SURFACE COVER, ARRANGEMENT, AND USE

CROSS-REFERENCE

This application is a section 371, of International application no. PCT/EP2013/000523, filed Feb. 22, 2013, which claims priority from German Patent application no. 10 2012 004 067.9, filed Mar. 3, 2012; German Patent application no. 10 2012 004 574.6, filed Mar. 10, 2012; German Patent application no. 10 2012 005 163.8, filed Mar. 17, 2012; and German Patent application no. 10 2012 007 068.3, filed Apr. 11, 2012.

FIELD

The invention relates to a gas-retaining surface covering for a body that can be placed in contact with a liquid, and to a corresponding arrangement and to a use.

BACKGROUND

From nature, surfaces of plants and animals are known which, when immersed in water, are wetted to a small extent by the water by virtue of the fact that air is retained in the structure of the surface, such that the immersed parts of the plant or of the animal are not wetted by the water. Said surfaces can be found inter alia in floating aquatic ferns (for example *Salvinia molesta*) or in water bugs (for example *Notonecta glauca*). With the aid of the air retained on the surface with layer thicknesses of approximately 1 μm to approximately 1 mm, floating aquatic ferns, for example, can increase their buoyancy, and water bugs can use the air supply carried along underwater for breathing.

However, air escapes as a result of detachment of gas bubbles and as a result of dissolution of the air in the surrounding liquid from the air layer retained on the surface of the plant or of the animal into the surrounding water, such that the air layer is depleted over time. Since the immersion time of a water bug and of a vital floating aquatic fern leaf is however shorter than the time required for consuming the air layer, the dissolution of gases from the air layer into the surrounding water is not a problem.

For technical applications, however, a problem is that of permanently separating the surface of an immersed body from the surrounding liquid by means of an air layer.

Said problem is solved by means of the subjects of the independent claims. The dependent claims relate to preferred embodiments.

SUMMARY

DESCRIPTION OF THE DRAWINGS

Preferred embodiments of the surface covering will be explained below by way of an example and on the basis of the appended drawings, in which:

FIG. 3: shows preferred embodiments of a gas-retaining layer of the surface covering, FIG. 4: shows further preferred embodiments of the gas-retaining layer, FIG. 13: shows two embodiments of a hydrophobic, gas-retaining fiber, FIG. 14: shows two further embodiments of a hydrophobic, gas-retaining fiber, FIG. 29: shows a gas-retaining layer which is formed by a rough surface, FIG. 30: shows a gas-retaining layer which is formed on a filiform element.

DETAILED DESCRIPTION

Use According to One Aspect

Figure 1:
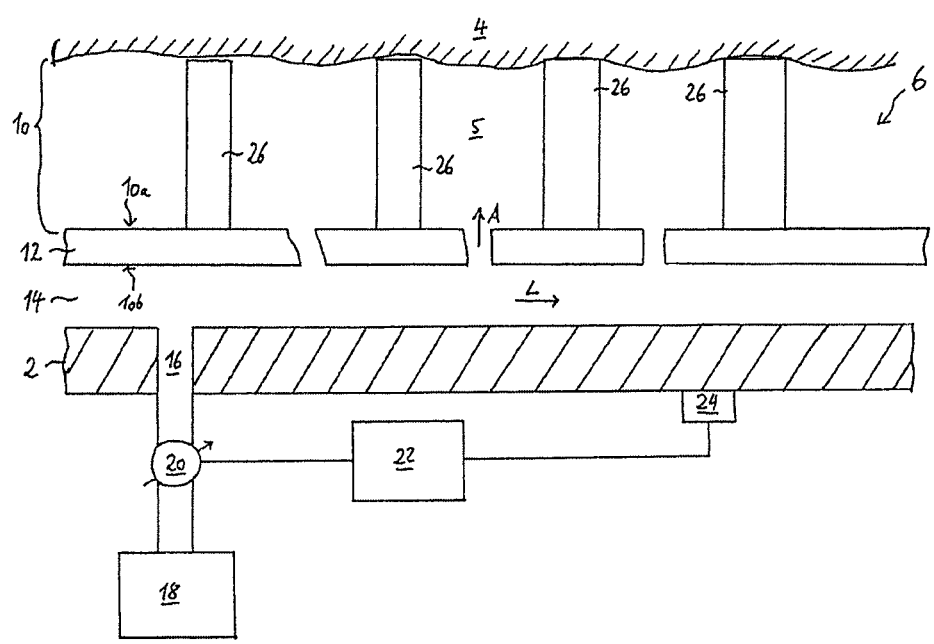
FIG. 1: shows a sectional view through a preferred embodiment of an arrangement of a surface covering on a body.

One aspect relates to the use of a gas-retaining layer which is designed, and arranged on a body that can be immersed in a liquid, so as to make contact at least regionally by way of a liquid-facing side, with a liquid when the body is immersed, at least regionally, in the liquid, wherein a gas layer which is retained in the immersed region of the gas-retaining layer separates the liquid and the immersed region of the body from one another at least regionally.

It is advantageously possible by means of the gas-retaining layer for a substantially constant gas volume to be retained on the body for a predetermined, in particular arbitrary, length of time, such that the body can be separated from the liquid surrounding the body by the gas-retaining layer or by the gas retained by said layer. In particular, the body can advantageously be protected from corrosive liquids in this way. Furthermore, it is advantageously possible for the flow resistance of the body in the case of a relative movement between body and liquid to be reduced.

Within the context of the application, the body may be any solid body which can be immersed, at least regionally, in a liquid. In other words, the body, when immersed in the liquid, cannot dissolve in said liquid and is not destroyed by the acting liquid pressure. Here, the liquid pressure may on the one hand act from the outside in the direction of the centre of gravity of the body if the body is immersed in the liquid, and may on the other hand act from the inside if the liquid fills a cavity of the body. Exemplary bodies within the context of this application are ships, buoys, pontoons, conduits, pipelines, undersea cables, oil drilling platforms, gas drilling platforms, foundations and water-exposed parts of offshore installations (in particular wind parks for electricity generation), underwater structures, underwater installations, liquid-exposed measurement equipment, shoreline structures, vessels and conduits for liquids or parts thereof. The body preferably comprises a substantially rigid wall which is subjected to the liquid pressure. The wall of the body is particularly preferably of resilient, in particular elastically deformable form.

The liquid, which may surround the body at least regionally or which may fill the body at least regionally, is in particular water (both fresh water and also sea water) or an aqueous solution, though the liquid may also comprise alcohols, alkanes, oils, polar and non-polar solvents and other organic and inorganic liquids.

The gas-retaining layer may be used to entirely or partially cover or form a face or surface of the body. Here, the gas-retaining layer may be detachably or non-detachably fastened to the body. The surface covering may preferably be in the form of a coating on the body. After the fastening of the gas-retaining layer to the body, the gas-retaining layer can form the surface of the body at least regionally or be regarded as a part of the body. In particular, the gas-retaining layer is attached to the body, so that the liquid cannot pass between the gas-retaining layer and the body.

The at least gas-retaining layer has a liquid-facing side and a body-facing side. The gas-retaining layer is designed such that, during operational use of the body, a gas of the gas-retaining layer is held in contact with the gas-retaining layer, wherein, by means of the gas, the liquid-facing side of the gas-retaining layer is at least partially, preferably entirely, spaced apart from the contact surface or interface between the retained gas and the liquid (liquid-gas interface). The gas which is retained by the gas-retaining layer is, within the context of the application, not part of the gas-retaining layer or of the body but part of a gas-containing layer which comprises the gas-retaining layer and the gas retained thereon. In other words, said retained gas is fixed by the gas-retaining layer such that, advantageously, it does not rise to the liquid surface and is not entrained by a liquid flow.

The gas-retaining layer may have a base or base ply which may preferably have structural elements such as projections, protruding elements and/or recesses, which are in particular designed so as to retain the gas, and which are preferably formed integrally with the base. The base may be of mesh-like form or in the form of a closed ply.

The gas-retaining layer accordingly also has a contact surface between the gas contained in the gas-retaining layer and a solid material. The liquid-facing side or the gas-facing side of the gas-retaining layer is preferably of hydrophobic form or may be coated with a hydrophobic material. Within the context of this application, the expression "hydrophobic" means the same as "liquid-repellent", that is to say "liquidophobic". The expression "hydrophobic" duly implies that the liquid is water or an aqueous solution or generally a polar solvent. It is however self-evident that the selection of the liquid with which contact is to be made is crucial. If the liquid with which contact is to be made is for example an alkane, the expression "hydrophobic" is also to be understood as "alkanophobic".

The question of whether a surface or a material is liquid-repellent can be determined on the basis of the contact angle of a liquid droplet on a surface of the material. The magnitude of the contact angle between liquid and solid is in this case dependent on the interaction between the liquid and the solid at the contact surface. The weaker said interaction is, the greater the contact angle is. Hydrophilic solids enclose contact angles from approximately 0° to approximately 90°, in particular angles of less than approximately 80°, with the surface of the liquid, in particular with water. Contact angles of approximately 90° and greater arise in the case of hydrophobic solids. Solids which have a contact angle of considerably greater than 90°, in particular contact angles of approximately 160° and greater, with the liquid, in particular with water, are referred to as superhydrophobic. The expression "hydrophobic" thus also encompasses the preferred case that a material is "superhydrophobic".

The subject matter of the invention relates in particular to the coexistence of hydrophilic and hydrophobic regions and/or elements. Within the context of the invention, it is thus the case in particular that a first element is distinguished, as hydrophobic, from a second, hydrophilic, element even if both elements should be classed as hydrophobic or hydrophilic in accordance with the absolute criteria described above with regard to the contact angle with a liquid, but the first element is more hydrophobic than the second element. In other words, the relatively hydrophobic element or the relatively hydrophobic region is referred to as hydrophobic, and the relatively hydrophilic, that is to say less hydrophobic element or the relatively hydrophilic regions are referred to as hydrophilic. In other words, within the context of the invention, the expressions hydrophobic and hydrophilic can describe a relative hydrophobicity or a contrast in hydrophobicity.

During operational use, the gas-retaining layer may for example be fed with air, carbon dioxide or some other gas.

The gas-retaining layer preferably has recesses and/or depressions at least regionally on the liquid-facing side. The surface of the gas-retaining layer may preferably be of hydrophobic form in the region of the recesses and/or depressions. For example, the material of the gas-retaining layer may be composed of a hydrophobic material. Alternatively, the gas-retaining layer may comprise a hydrophilic material which is provided regionally with a hydrophobic coating. In particular, the hydrophobic coating may be formed only on the walls of the recesses or depressions. The gas-retaining layer is particularly preferably composed at least regionally of a porous material, wherein the recesses or depressions are formed by pores that are connected to the surface.

The gas-retaining layer preferably has projections or protruding elements at least regionally on the liquid-facing side, wherein the surface of the gas-retaining layer is substantially hydrophobic in the region of the projections or protruding elements. The spacing between the protruding elements is expediently dimensioned such that no liquid droplets can become disposed between the protruding elements. The individual droplets of the liquid are advantageously borne by a multiplicity of protruding elements, such that the interface between liquid and the gas situated between the protruding elements is substantially in the form of an envelope of the protruding elements. In particular, the spacing between two adjacent protruding elements may be approximately 50 µm to approximately 500 µm, preferably approximately 100 µm to approximately 200 µm.

The projections or protruding elements preferably have a central surface region which is hydrophilic and which is surrounded by a hydrophobic surface region of the projections or protruding elements. The interface between the liquid and the gas is advantageously localized at the regions which are of hydrophilic form. In this way, it is furthermore advantageously achieved that detachment of gas bubbles by a flow of the liquid is prevented.

The gas-retaining layer is preferably divided into a multiplicity of sub-regions (also referred to as "compartments") by fluid-impermeable partitions. The partitions (42) are preferably at least regionally or entirely of hydrophilic form or provided at least regionally or entirely with a hydrophilic surface. A fluid is to be understood to mean a gas, a liquid and a mixture of these. Consequently, the partition prevents a liquid flow or a gas flow between adjacent sub-regions. It is advantageously the case that, in the presence of a pressure difference between two adjacent sub-regions, the partitions prevent gas from flowing away from one sub-region to the adjacent sub-region and as a result the flow resistance in relation to a liquid with which contact is made being locally increased and, by contrast, excess gas being released into the liquid from the sub-region into which the gas flows.

The partitions may preferably be formed in one piece or integrally together with further elements of the gas-retaining layer. It is furthermore preferable for a multiplicity of hydrophobic protruding elements to be situated in a two-dimensional arrangement in all of the sub-regions of the gas-retaining layer.

The gas-retaining layer preferably comprises an embossed plastics resin or an embossed lacquer. In particular, the gas-retaining layer may be cast from a liquid plastics resin, wherein preferably protruding elements are formed integrally or in one piece with a base ply of the gas-retaining layer and/or with the gas-permeable ply. In particular, the base ply of the gas-retaining layer may be identical to the gas-permeable ply. The gas-retaining layer is particularly preferably formed, by means of the plastics resin or the lacquer, indirectly or directly on the wall of the immersible body. In particular, the gas-retaining layer can be used to realize a surface coating or surface seal of the body.

The gas-retaining layer is preferably coated at least regionally with polytetrafluoroethylene (PTFE), also known under the trade name Teflon, or with the derivatives thereof. In particular, the coating may also comprise microparticles or nanoparticles of polytetrafluoroethylene or other materials. The coating composed of PTFE advantageously acts as a hydrophobic layer and as an anti-adhesion agent, such that adhesion of liquids or solids to the gas-retaining layer is prevented. The coating of the gas-retaining layer is preferably approximately 0.15 nm to approximately 500 nm thick.

The liquid is preferably water, and the body is preferably a watercraft whose wall is immersed, at least regionally, in the water when the watercraft is in an operating position.

It is advantageously the case that the water, in particular sea water, at least regionally cannot wet the wall of the watercraft, such that the watercraft is protected against the influence of the water. The watercraft may for example be a ship, a drilling platform or a buoy. The influence of the water refers in particular to the corrosion of the wall of the watercraft. Sea water or brackish water in particular promote the corrosion of the wall of the watercraft owing to their salt content. Since the contact between the water and the wall of the watercraft is prevented by means of the interposed gas which is retained by the gas-retaining layer, corrosion is also reduced.

A further advantage consists in that the fouling of the wall of the watercraft by organisms living in the water, for example algae, mussels, barnacles and others, is prevented. The gas layer makes it difficult for said organisms to attach to the wall of the watercraft. In other words, the surface covering according to the invention has an antifouling action, wherein it is advantageously possible to dispense with biocides, the poisonous substances of which dissolve in the water over time. Owing to the reduced adhesion of organisms on the wall of the watercraft, the flow resistance of the watercraft is also reduced.

It is preferably the case that between the gas-retaining layer is charged with a gas at least regionally so as to reduce the flow resistance between the water and the watercraft. In particular, the gas layer may have a thickness of approximately 10 nm to approximately 10 mm, preferably from approximately 500 nm to approximately 3 mm, in particular approximately 0.1 mm to approximately 3 mm. If the gas layer is intended to serve merely for corrosion prevention, even a relatively thin gas layer with a thickness of approximately 5 nm to approximately 3 mm, preferably of approximately 50 nm to approximately 1 nm, in particular of approximately 100 nm to approximately 100 µm, may suffice in order to obtain the corrosion prevention action. Since the gas layer decouples the wall of the watercraft from the water flowing past, and in particular, the contact surface between the gas and the water can be deformed by the flow, such that an extremely streamlined contact surface is formed, the flow resistance of the watercraft as it travels through the water is advantageously reduced. In particular, the fuel consumption of the watercraft can advantageously be reduced owing to the reduced flow resistance between the watercraft and the water.

A corrosion prevention coating and/or an antifouling coating is preferably arranged between the gas-retaining layer and the wall of the watercraft, wherein the gas-retaining layer separates the corrosion prevention coating and/or the antifouling coating from the water at least regionally.

The corrosion prevention coating is generally formed as a paint coat on the wall of the watercraft and may contain poisonous substances such as, for example, heavy metals. The dissolution of said poisonous substances from the corrosion prevention coating in the water is reduced or prevented by the arrangement of the gas-retaining layer between the corrosion prevention coating and the water. In this way, contamination of the water, in particular of the sea water, with poisonous substances is advantageously prevented. In particular, heavy metals are prevented from passing from a corrosion prevention paint coat into the water and accumulating in the food chain there.

Alternatively or in addition, an antifouling coating may be formed on the wall of the watercraft, for example in the form of a paint coat on the wall. The antifouling coating generally includes biocides, that is to say poisonous substances which are lethal to the organisms that adhere to the wall of the watercraft. The dissolution of said poisonous substances from the antifouling coating in the water is reduced or prevented by the arrangement of the gas-retaining layer between the antifouling coating and the water. In this way, contamination of the water, in particular of the sea water, with the biocides is advantageously prevented. In particular, the biocides are prevented from harming or killing organisms living in the water, such as for example plankton, which would disrupt the food chain in the water.

The gas-retaining layer is preferably fed with a fouling-inhibiting gas. The fouling-inhibiting gas may for example contain carbon dioxide in order that the organisms that have accumulated on the wall of the watercraft are deprived of oxygen or saturated with carbon dioxide. Said organisms thus die off without the need to use a toxic substance in an antifouling coating. This advantageously leads to reduced contamination of the water with poisonous substances.

The body is preferably a vessel wall which can be wetted with a liquid and on the wall of which the gas-retaining layer is arranged at least regionally.

It is advantageously the case that the liquid at least regionally cannot wet the vessel wall, such that the vessel wall is protected against the influence of the liquid. The vessel that has the vessel wall may for example be a tank, a conduit, a reactor or the like. The influence of the liquid refers in particular to the corrosion of the vessel wall, the chemical reaction of the liquid with the vessel wall, or the mechanical loading of the vessel wall by particles contained in the liquid. The corrosion of the vessel wall is promoted in particular by salty solutions, brines or acids. Since the contact between the liquid and the vessel wall is prevented by the gas which is arranged in between and which is retained by the gas-retaining layer, corrosion is also reduced.

The vessel wall particularly preferably comprises a sensor window on which a gas-retaining layer is arranged. The detection of sensor data can advantageously be improved because no deposits, for example particles or organisms, can accumulate on the sensor window. In particular, the sensor window and/or the gas-retaining layer is optically transparent.

A corrosion prevention coating is preferably arranged between the gas-retaining layer and the wall of the vessel, wherein the gas-retaining layer separates the corrosion prevention coating from the liquid at least regionally.

The corrosion prevention coating is generally in the form of a paint coat on the vessel wall or formed by galvanizing or anodizing, and may contain poisonous substances such as, for example, heavy metals. The dissolution of said poisonous substances from the corrosion prevention coating in the liquid is reduced or prevented by the arrangement of the gas-retaining layer between the corrosion protection coating and the liquid. In this way, contamination of the liquid, in particular with poisonous substances, is advantageously prevented. In particular, said substances from the corrosion prevention coating are prevented from influencing a chemical reaction within the vessel.

The gas-retaining layer is preferably charged with gas from a body-facing side, situated opposite the liquid-facing side, of the gas-retaining layer.

A gas-permeable ply is preferably arranged on the body-facing side on the gas-retaining layer. In other words, the gas-permeable ply may be arranged on and/or fastened to the body-facing side of the gas-retaining layer. Alternatively, the gas-permeable ply may also be formed in one piece with the gas-retaining layer or may be an integral constituent part of the gas-retaining layer. A gas can be fed to the gas-retaining layer through the liquid-facing side of the gas-permeable ply, which may be in contact with the body-facing side of the gas-retaining layer. In other words, the gas-permeable ply may be permeable to a gas, in particular in a direction oriented perpendicular to the body-facing side of the gas-retaining ply.

The gas-permeable ply is preferably in the form of a liquid-impermeable and/or hydrophobic ply. The liquid advantageously can not flow through the gas-permeable ply in the direction of the body, for example if the liquid pressure is temporarily higher than the gas pressure in the gas-permeable ply. In other words, the gas-permeable ply repels water and other polar solvents, whereby said polar solvents are advantageously prevented from ingressing into the gas-permeable ply.

A gas feed device is preferably connected to the gas-permeable ply such that gas can flow from a gas feed device to the gas-retaining layer through the gas-permeable ply.

It is advantageously possible for gas to be fed to the gas-retaining layer by means of the gas feed device and via the gas-permeable ply. In particular, it is possible for at least the amount of gas that escapes from the gas-retaining layer into the surrounding liquid to be fed in. In this way, it is advantageously possible for a substantially constant gas volume to be kept within the gas-retaining layer for any desired length of time, whereby the body and the surrounding liquid can be permanently separated by means of the gas in the gas-retaining layer.

The gas may be provided by means of the gas feed device, which is connected to the gas-permeable ply. The gas feed device may preferably be a ply of a porous material with a continuous pore space, such that gas can flow from the gas feed device to the gas-retaining layer through the gas-permeable ply.

The gas-permeable ply preferably comprises a woven or non-woven textile, a flock material, a porous ceramic, a porous metal, a felt composed of polymer or metal fibers, and/or a metal wire mesh. The gas-permeable ply may for example be woven from polymer fibers or be composed of a felt or nonwoven composed of polymer fibers. A gas-permeable ply composed of a polymer may be connected to the gas-retaining layer in particular by lamination. The gas-permeable ply may alternatively or additionally comprise a fabric composed of metal wire, in particular corrosion-resistant metal wire, for example rust-resistant high-grade steel wire, whereby a high level of mechanical tear resistance and resistance to UV radiation and chemical influences is advantageously obtained. Alternatively, the gas-permeable ply may also comprise a flock material, for example polymer flock or elastomer flock, composed in particular of a foamed material. The weight of the gas-permeable ply can advantageously be reduced in this way. Furthermore, the gas-permeable ply may preferably comprise a sintered material, such as for example a porous sintered material composed of metal particles. The gas-permeable ply may preferably be connected to the gas-retaining layer by way of an adhesive. Alternatively, the gas-retaining layer and the gas-permeable ply may be connected to one another by welding, in particular ultrasound welding (ultrasonic welding). The gas-retaining layer and the gas-permeable ply are particularly preferably formed in one piece with one another, for example from a polymer by way of a (continuous) molding or casting process. The gas-permeable ply is preferably in the form of a porous semipermeable membrane. The gas-permeable ply may in particular be in the form of a gas-permeable foil composed of a polymer. Gas-permeable foils may for example have a thickness of approximately 0.5 µm to 5 µm. It is possible in this way to provide a surface covering with a small thickness and a low weight. In particular, foils composed of a polymer can be connected to the gas-retaining layer by lamination. The gas feed device is preferably in the form of a gas-permeable layer which is arranged on the body-facing side of the gas-permeable layer. In particular, the gas feed device may also comprise a porous material which has continuous pores. The gas permeability through the gas feed device is expediently higher than the gas permeability through the gas-permeable ply.

The gas feed device is preferably in the form of an aerenchyma. An aerenchyma is an air passage structure in aquatic plants which permits gas transport and gas storage. In particular, the expression "aerenchyma" is understood to mean a form of plant base structure in which the intercellular spaces are so large that a true "air passage structure" is formed. This is encountered in particular in marsh plants and aquatic plants and serves for the gas exchange of the immersed plant organs.

In other words, the gas feed device is in the form of a gas store, such that, with rising liquid pressure, gas can be displaced via the gas-permeable ply back into the gas feed device and stored there in order that it can be displaced into the gas-retaining layer again via the gas-permeable ply in the event of a decrease in liquid pressure. The gas feed device may for example have a porous material in which gas can be stored. Furthermore, the material may be resiliently expandable such that the volume increases with rising gas pressure, and gas can be forced through the gas-permeable ply into the gas-retaining layer owing to the resilient force of the material. It is furthermore preferable for the inner walls of the gas feed device, which come into contact with the gas, to be at least regionally of hydrophobic form. It is advantageously possible for the gas from the gas-retaining layer to be temporarily stored in the gas feed device, rather than being released from the gas-retaining layer, in the event of liquid pressure fluctuations.

The gas-retaining layer is preferably charged with gas from the liquid-facing side of the gas-retaining layer.

It is preferable for at least one gas discharge device to be provided which has a gas discharge opening at the liquid-facing side of the gas-retaining layer, wherein a gas feed device is provided which is connected to the gas discharge device, wherein gas provided by the gas feed device flows out of the gas discharge device and is at least partially received by the gas-retaining layer.

The gas discharge device preferably extends through the gas-retaining layer. In other words, a gas discharge opening of the gas discharge device is arranged at the liquid-facing side of the gas-retaining layer.

The gas feed device is preferably in the form of a gas-permeable layer which is arranged on the body-facing side of the gas-permeable layer. The gas feed device is particularly preferably in the form of an aerenchyma. The gas feed device can advantageously be fluidically connected in a simple manner to a multiplicity of gas discharge devices, wherein the gas discharge devices may in particular be arranged in a regular or irregular manner over an area.

Watercraft According to One Aspect

One aspect relates to a watercraft having:
a wall which is immersed, at least regionally, in water when the watercraft is in an operating position, wherein an at least partially gas-retaining layer is arranged on a side facing toward the water; and having:
a gas-permeable ply which is arranged on a wall-facing side, situated opposite the water-facing side, between the gas-retaining layer and the wall;
a gas feed device which is connected to the gas-permeable ply such that gas can flow from the gas feed device to the gas-retaining layer through the gas-permeable ply, or having:
at least one gas discharge device which has a gas discharge opening at the water-facing side of the gas-retaining layer;
a gas feed device which is connected to the gas discharge device, wherein gas provided by the gas feed device can flow out of the gas discharge device and can be at least partially received by the gas-retaining layer.

It is preferable for a corrosion prevention coating and/or an antifouling coating to be arranged between the gas-retaining layer and the wall of the watercraft, wherein the gas-retaining layer separates the corrosion prevention coating and/or the antifouling coating from the water at least regionally.

The gas-retaining layer can preferably be fed with a fouling-inhibiting gas.

One aspect relates to a liquid vessel comprising:
a vessel wall which can be wetted at least regionally with a liquid, wherein an at least partially gas-retaining layer is arranged on a side, which faces toward the liquid, of the vessel wall; and comprising:
a gas-permeable ply which is arranged on a wall-facing side, situated opposite the water-facing side, between the gas-retaining layer and the vessel wall; and
a gas feed device which is connected to the gas-permeable ply such that gas can flow from the gas feed device to the gas-retaining layer through the gas-permeable ply, or comprising:
at least one gas discharge device which has a gas discharge opening at the liquid-facing side of the gas-retaining layer; and
a gas feed device which is connected to the gas discharge device, wherein gas provided by the gas feed device can flow out of the gas discharge device and can be at least partially received by the gas-retaining layer.

It is preferable for a corrosion prevention coating to be arranged between the gas-retaining layer and the wall of the liquid vessel, wherein the gas-retaining layer separates the corrosion prevention coating from the liquid at least regionally.

Surface Covering According to One Aspect

One aspect relates to a surface covering for a body that can be placed in contact with a liquid, comprising:
an at least partially gas-retaining layer which is designed and arranged so as to make contact, at least regionally by way of a liquid-facing side, with the liquid;
a gas-permeable ply which is arranged on a body-facing side, situated opposite the liquid-facing side, on the gas-retaining layer or which is formed integrally with the gas-retaining layer;

a gas feed device which is connected to the gas-permeable ply such that gas can flow from the gas feed device to the gas-retaining layer through the gas-permeable ply.

It is advantageously possible for gas to be fed to the gas-retaining layer by means of the gas feed device and via the gas-permeable ply. In particular, it is possible for at least the amount of gas that escapes from the gas-retaining layer into the surrounding liquid to be fed in. In this way, it is advantageously possible for a substantially constant gas volume to be kept within the gas-retaining layer for any desired length of time, whereby the body and the surrounding liquid can be permanently separated by means of the gas in the gas-retaining layer. In particular, the body can advantageously be protected from corrosive liquids in this way. Furthermore, it is advantageously possible for the flow resistance of the body in the case of a relative movement between body and liquid to be reduced.

Within the context of the application, the body that can be placed in contact with the liquid may be any solid body which can be immersed, at least regionally, in a liquid. In other words, the body, when immersed in the liquid, does not dissolve in said liquid and is likewise not destroyed by the acting liquid pressure. Here, the liquid pressure may on the one hand act from the outside in the direction of the center of gravity of the body if the body is immersed in the liquid, and may on the other hand act from the inside if the liquid fills a cavity of the body. Exemplary bodies within the context of this application are ships, buoys, pontoons, shoreline structures, vessels and conduits for liquids. The body preferably comprises a substantially rigid wall which is subjected to the liquid pressure. The wall of the body is particularly preferably of resilient, in particular elastically deformable form.

Within the context of the application, the expression "resilient" encompasses in particular that the wall of the body can be deformed under the action of an external force, such as for example the liquid pressure, wherein the deformation is substantially fully reversed when the external force ceases to act, that is to say the body substantially returns to its original shape or position after the external force has acted.

The liquid, which may surround the body at least regionally or which may fill the body, may comprise in particular water (both fresh water and also sea water) and aqueous solutions, but also alcohols, alkanes, oils, polar and non-polar solvents and other organic and inorganic liquids.

The surface covering may entirely or partially cover a face or surface of the body. Furthermore, the surface covering may be detachably or non-detachably fastened to the body. In particular, the surface covering may be in the form of a coating on the body. After the fastening of the surface covering to the body, the surface covering can be regarded as a part of the body.

The at least partially gas-retaining layer has a liquid-facing side and a body-facing side. The gas-retaining layer is designed such that, during operational use of the body or the surface covering, a gas of the gas-retaining layer is held in contact with the gas-retaining layer, wherein, by means of the gas, the liquid-facing side of the gas-retaining layer is at least partially, preferably entirely, spaced apart from the contact surface or interface between the retained gas and the liquid (liquid-gas interface). The gas which is retained by the gas-retaining layer is, within the context of the application, not part of the gas-retaining layer or of the surface covering but part of a gas-containing layer which comprises the gas-retaining layer and the gas retained thereon. In other words, said retained gas is fixed by the gas-retaining layer such that, advantageously, it does not rise to the liquid surface and is not entrained by a liquid flow.

The gas-retaining layer may have a base or base ply which may preferably have structural elements such as projections, protruding elements and/or recesses, which are in particular designed so as to retain the gas, and which are preferably formed integrally with the base. The base may be of mesh-like form or in the form of a closed ply.

The gas-retaining layer accordingly also has a contact surface between the gas contained in the layer and a solid material. The liquid-facing side or the gas-facing side of the gas-retaining layer is of hydrophobic form or may be coated with a hydrophobic material. Within the context of this application, the expression "hydrophobic" means the same as "liquid-repellent", that is to say "liquidophobic". The expression "hydrophobic" duly implies that the liquid is water or an aqueous solution or generally a polar solvent. It is however self-evident that the selection of the liquid with which contact is to be made is crucial. If the liquid with which contact is to be made is for example an alkane, the expression "hydrophobic" is also to be understood as "alkanophobic".

The question of whether a surface or a material is liquid-repellent can be determined on the basis of the contact angle of a liquid droplet on a surface of the material. The magnitude of the contact angle between liquid and solid is in this case dependent on the interaction between the liquid and the solid at the contact surface. The weaker said interaction is, the greater the contact angle is. Hydrophilic solids enclose contact angles from approximately 0° to approximately 90°, in particular angles of less than approximately 80°, with the surface of the liquid, in particular with water. Contact angles of approximately 90° and greater arise in the case of hydrophobic solids. Solids which have a contact angle of considerably greater than 90°, in particular contact angles of approximately 160° and greater, with the liquid, in particular with water, are referred to as superhydrophobic. The expression "hydrophobic" thus also encompasses the preferred case that a material is "superhydrophobic".

The gas-permeable ply is arranged on and/or fastened to the body-facing side of the gas-retaining layer. Alternatively, the gas-permeable ply may also be formed in one piece with the gas-retaining layer or may be an integral constituent part of the gas-retaining layer. A gas can be fed to the gas-retaining layer through the liquid-facing side of the gas-permeable ply, which may be in contact with the body-facing side of the gas-retaining layer. In other words, the gas-permeable ply is permeable to a gas, in particular in a direction oriented perpendicular to the body-facing side of the gas-retaining layer.

The gas fed to the gas-retaining layer may for example be air, nitrogen, carbon dioxide or some other gas. The gas may be provided by means of the gas feed device, which is connected to the gas-permeable ply. The gas feed device may preferably be a ply of a porous material with a continuous pore space, such that gas can flow from the gas feed device to the gas-retaining layer through the gas-permeable ply.

The gas-permeable ply is preferably impermeable to liquid, in particular impermeable to water or impervious to liquid. It is advantageously possible for a gas to flow from the gas feed device to the gas-retaining layer counter to the liquid pressure, but the liquid cannot flow through the gas-permeable ply in the direction of the gas feed device, for example if the liquid pressure is temporarily higher than the gas pressure in the gas feed device.

The gas-permeable ply preferably comprises a woven or non-woven textile, a flock material, a porous ceramic, a porous metal, a felt composed of polymer or metal fibers, and/or a metal wire mesh. The gas-permeable ply may for example be woven from polymer fibers or be composed of a felt or nonwoven composed of polymer fibers. A gas-permeable ply composed of a polymer may be connected to the gas-retaining layer in particular by lamination. The gas-permeable ply may alternatively or additionally comprise a fabric composed of metal wire, in particular corrosion-resistant metal wire, for example rust-resistant high-grade steel wire, whereby a high level of mechanical tear resistance and resistance to UV radiation and chemical influences is advantageously obtained. Alternatively, the gas-permeable ply may also comprise a flock material, for example polymer flock or elastomer flock, composed in particular of a foamed material. The weight of the gas-permeable ply can advantageously be reduced in this way. Furthermore, the gas-permeable ply may preferably comprise a sintered material, such as for example a porous sintered material composed of metal particles. The gas-permeable ply may preferably be connected to the gas-retaining layer by way of an adhesive. Alternatively, the gas-retaining layer and the gas-permeable ply may be connected to one another by welding, in particular ultrasound welding (ultrasonic welding). The gas-retaining layer and the gas-permeable ply are particularly preferably formed in one piece with one another, for example from a polymer by way of a (continuous) molding or casting process.

The gas-permeable ply is preferably in the form of a porous, in particular microporous or nanoporous, semipermeable membrane. The gas-permeable ply may in particular be in the form of a gas-permeable foil composed of a polymer. Gas-permeable foils may for example have a thickness of approximately 0.5 µm to 5 µm. It is possible in this way to provide a surface covering with a small thickness and a low weight. In particular, foils composed of a polymer can be connected to the gas-retaining layer by lamination.

The gas-permeable ply is preferably in the form of a hydrophobic or superhydrophobic ply. In other words, the gas-permeable ply repels water and other polar solvents, whereby said polar solvents are advantageously prevented from ingressing into the gas-permeable ply.

The gas feed device is preferably in the form of a gas-permeable layer which is arranged on the body-facing side of the gas-permeable layer. In particular, the gas feed device may also comprise a porous material which has continuous pores. The gas permeability through the gas feed device is expediently higher than the gas permeability through the gas-permeable ply.

The gas feed device is preferably in the form of an aerenchyma. An aerenchyma is an air passage structure in aquatic plants which permits gas transport and gas storage. In particular, the expression "aerenchyma" is understood to mean a form of plant base structure in which the intercellular spaces are so large that a true "air passage structure" is formed. This is encountered in particular in marsh plants and aquatic plants and serves for the gas exchange of the immersed plant organs.

In other words, the gas feed device is in the form of a gas store, such that, with rising liquid pressure, gas can be displaced via the gas-permeable ply back into the gas feed device and stored there in order that it can be displaced into the gas-retaining layer again via the gas-permeable ply in the event of a decrease in liquid pressure. The gas feed device may for example have a porous material in which gas can be stored. Furthermore, the material may be resiliently expandable such that the volume increases with rising gas pressure, and gas can be forced through the gas-permeable ply into the gas-retaining layer owing to the resilient force of the material. It is furthermore preferable for the inner walls of the gas feed device, which come into contact with the gas, to be at least regionally of hydrophobic form. It is advantageously possible for the gas from the gas-retaining layer to be temporarily stored in the gas feed device, rather than being released from the gas-retaining layer, in the event of liquid pressure fluctuations.

The gas-retaining layer preferably has recesses or depressions at least regionally on the liquid-facing side, wherein the surface of the gas-retaining layer is preferably of hydrophobic form in the region of the recesses or depressions. For example, the material of the gas-retaining layer may be composed of a hydrophobic material. Alternatively, the gas-retaining layer may comprise a hydrophilic material which is provided regionally with a hydrophobic coating. In particular, the hydrophobic coating may be formed only on the walls of the recesses or depressions. The gas-retaining layer is particularly preferably composed at least regionally of a porous material, wherein the recesses or depressions are formed by pores that are connected to the surface.

The gas-retaining layer preferably has projections or protruding elements at least regionally on the liquid-facing side, wherein the surface of the gas-retaining layer is substantially hydrophobic in the region of the projections or protruding elements. The spacing between the protruding elements is expediently dimensioned such that no liquid droplets can become disposed between the protruding elements. The individual droplets of the liquid are advantageously borne by a multiplicity of protruding elements, such that the interface between liquid and the gas situated between the protruding elements is substantially in the form of an envelope of the protruding elements. In particular, the spacing between two adjacent protruding elements may be approximately 50 µm to approximately 500 µm, preferably approximately 100 µm to approximately 200 µm.

The projections or protruding elements preferably have a central surface region which is hydrophilic and which is surrounded by a hydrophobic surface region of the projections or protruding elements. The interface between the liquid and the gas is advantageously localized at the regions which are of hydrophilic form. In this way, it is furthermore advantageously achieved that detachment of gas bubbles by a flow of the liquid is prevented.

The gas-retaining layer is preferably divided into a multiplicity of sub-regions (also referred to as "compartments") by fluid-impermeable partitions. A fluid is to be understood to mean a gas, a liquid and a mixture of these. Consequently, the partition prevents a liquid flow or a gas flow between adjacent sub-regions. It is advantageously the case that, in the presence of a pressure difference between two adjacent sub-regions, the partitions prevent gas from flowing away from one sub-region to the adjacent sub-region and the flow resistance in relation to a liquid with which contact is made thereby being locally increased and, by contrast, excess gas being released into the liquid from the sub-region into which the gas flows.

The partitions may preferably be formed in one piece or integrally together with the further elements of the gas-retaining layer. It is furthermore preferable for a multiplicity of hydrophobic protruding elements to be situated in a two-dimensional arrangement in all of the sub-regions of the gas-retaining layer.

The gas-retaining layer preferably comprises an embossed plastics resin or an embossed lacquer. In particular, the gas-retaining layer may be cast from a liquid plastics resin, wherein it is preferably possible for protruding elements to be formed integrally or in one piece with a base ply of the gas-retaining layer and/or with the gas-permeable ply. In particular, the base ply of the gas-retaining layer may be identical to the gas-permeable ply.

The gas-retaining layer is preferably coated at least regionally with polytetrafluoroethylene (PTFE), also known under the trade name Teflon, or with the derivatives thereof. In particular, the coating may also comprise microparticles or nanoparticles of polytetrafluoroethylene or other materials. The coating composed of PTFE advantageously acts as a hydrophobic layer and as an anti-adhesion agent, such that adhesion of liquids or solids to the gas-retaining layer is prevented. The coating of the gas-retaining layer is preferably approximately 0.15 nm to approximately 500 nm thick.

Surface Covering According to One Aspect

One aspect relates to a surface covering for a body that can be placed in contact with a liquid, comprising:
- an at least partially gas-retaining layer which is designed and arranged so as to make contact, at least regionally by way of a liquid-facing side, with the liquid;
- at least one gas discharge device which has a gas discharge opening at the liquid-facing side of the gas-retaining layer;
- a gas feed device which is connected to the gas discharge device, wherein gas is provided by the gas feed device can flow out of the gas discharge device and can be at least partially received by the gas-retaining layer.

The gas discharge device preferably extends through the gas-retaining layer. In other words, a gas discharge opening of the gas discharge device is arranged at the liquid-facing side of the gas-retaining layer.

The gas feed device is preferably in the form of a gas-permeable layer which is arranged at the body-facing side of the gas-permeable layer. The gas feed device is particularly preferably in the form of an aerenchyma. The gas feed device can advantageously be fluidically connected in a simple manner to a multiplicity of gas discharge devices, wherein the gas discharge devices may in particular be arranged in a regular or irregular manner over an area.

Furthermore, preferred features of the gas-retaining layer and of the recesses, depressions or protruding elements thereof, as have been described with regard to the aspect of the invention above, may be provided analogously in this embodiment.

Arrangement According to One Aspect

One aspect relates to an arrangement comprising:
- a surface covering according to the invention, and
- a gas source which is fluidically connected to the gas feed device of the surface covering.

The gas source may preferably comprise a compressor, a pressure vessel for the storage of gas, a gas-generating reactor or other devices that can provide gas at a gas pressure sufficient to cause the gas to flow into the gas-retaining layer. The gas-generating reactor may preferably be a combustion engine, the exhaust gases of which are utilized to maintain the gas layer.

The arrangement preferably furthermore comprises:
- at least one sensor device for determining the gas content in the gas-retaining layer of the surface covering, and
- a regulating device by means of which measurement data can be received from the at least one sensor device and which regulates the gas flow from the gas source to the gas feed device on the basis of the received measurement data.

It is advantageously possible by means of the regulating device for a constant gas pressure or a constant gas layer thickness to be maintained within the gas-retaining layer. Preferred sensor devices may therefore comprise pressure sensors, ultrasound sensors and/or sensors for determining the gas layer thickness. Alternatively, a regulating device may also be provided which is configured so as to feed gas to the gas-retaining layer at predetermined time intervals.

Use According to One Aspect

One aspect relates to the use of a surface covering according to the invention, wherein the surface covering covers a face of a body at least regionally, wherein, in the event that the body is immersed in a liquid at least regionally by way of the face covered by the surface covering, a gas layer permanently spaces the liquid and the immersed region apart from one another at least regionally.

It is advantageously the case that at least regionally cannot be wetted by the liquid, such that the body is protected from corrosive liquids. It is furthermore advantageously the case that the body can be moved relative to the liquid with reduced expenditure of force, because the flow resistance is reduced owing to the liquid-gas interface.

The body may in particular be a ship, such that the fuel consumption can advantageously be reduced owing to the reduced flow resistance between the ship wall and the water. Furthermore, the gas layer between the ship wall and the water advantageously protects against corrosion of the ship, in particular in sea water, and against fouling with organisms, for example algae, mussels, barnacles and others. In other words, the surface covering according to the invention has an antifouling action, wherein it is advantageously possible to dispense with biocides, the poisonous substances of which dissolve in the water over time.

The surface of the body is preferably a wall of a watercraft or of a structure arranged in the water, or an internal wall of a liquid vessel or of a liquid conduit.

Use According to One Aspect

One aspect relates to the use of a surface covering according to the invention, wherein the surface covering covers a mounting face of a body at least regionally, wherein, in the event that the body is immersed in a liquid by way of the mounting face covered by the surface covering, a gas layer permanently spaces the liquid and the mounting face apart from one another, such that a second body to be mounted can be mounted on the mounting face such that a gas layer is situated at least regionally between the body and the second body.

By means of the gas layer, it is advantageously possible for the second body to be mounted on the body substantially without contact and without friction.

The face of the body is preferably a bore whose internal wall forms the mounting surface. The second body to be mounted is then preferably a shaft, such that the arrangement composed of the body with surface covering and of the shaft has the action of a ball bearing.

FIG. 1 shows a wall 2 of a body which is designed to be immersed at least regionally in a liquid 4. On the liquid-facing side of the wall 2, a surface covering 6 is arranged on and/or fastened to the wall 2 at least regionally.

The surface covering 6 comprises an at least partially gas-retaining layer 10 which makes contact, at least regionally by way of a liquid-facing side 10a, with the liquid 4. The surface covering 6 furthermore comprises a gas-permeable ply 12 which is arranged on and/or fastened to a body-facing side 10b, situated opposite the liquid-facing side 10a, of the gas-retaining layer 10. In the preferred embodiment shown in FIG. 1, the gas-retaining layer 10 and the gas-permeable ply 12 are formed in one piece or integrally. It is however self-evident that the gas-retaining layer 10 and the gas-permeable ply 12 may be formed separately from one another and connected to one another or fastened to one another.

The surface covering furthermore comprises a gas feed device 14 which is connected to the gas-permeable ply 12. In other words, the gas feed device 14 and the gas-permeable ply 12 are at least fluidically connected to one another such that gas can flow from the gas feed device 14 to the gas-retaining layer 10 through the gas-permeable ply 12. In the embodiment shown in FIG. 1, the gas feed device 14 is in the form of a gas-conducting duct which is arranged between the gas-permeable ply 12 and the wall 2. The gas feed device 14 may preferably also be in the form of a gas-permeable, in particular porous layer, wherein the pore space of the gas feed device particularly preferably has continuous pores such that gas can flow through the gas feed device along a longitudinal direction L. In this way, the gas feed device can advantageously provide gas to the gas-permeable ply 12 over an area, which gas then flows through the gas-permeable ply 12 into the gas-retaining layer 10 preferably along an outflow direction A which may be oriented substantially perpendicular to the longitudinal direction L. The gas feed device 14 may furthermore preferably serve for connecting the gas-permeable ply 12, and the gas-retaining layer 10 connected thereto, to the wall 2. The gas feed device 14 and the gas-permeable ply 12 may for example be mechanically connected to one another, for example by adhesive bonding or lamination, such that the surface covering 6 can be fastened to the body by virtue of a body-facing side of the gas feed device being fastened to the wall 2. It is furthermore preferably possible for the gas-permeable ply 12 and the gas feed device 14 to be formed in one piece or integrally with one another. It is particularly preferable for the gas-retaining layer 10, the gas-permeable ply 12 and the gas feed device 14 to be formed together in one piece. The gas feed device 14 is fluidically connected by means of a gas feed device duct 16 to a gas source 18, wherein the amount of gas flowing into the gas feed device 14 can be regulated or controlled by means of a valve 20 and a regulating device 22 connected to said valve. The preferred embodiment shown in FIG. 1 furthermore comprises a sensor device 24 which is configured to determine the gas content in the gas-retaining layer 10 of the surface covering 6. This may be performed for example by means of the reflection of an ultrasound signal or of an electromagnetic wave. The measurement of the gas content in the gas-retaining layer 10 is preferably performed by the sensor device 24 in contactless fashion, such that the sensor device 24 does not need to be arranged such that the sensor device 24 is wetted by the liquid 4. In particular, the sensor device 24 may be arranged on a liquid-averted side of the wall 2, wherein the measurement of the gas content can preferably be performed through the wall 2. Based on the gas quantity within the gas-retaining layer 10 of the surface covering 6 as measured by the sensor device 24, the regulating device 22 determines the amount of gas that must be fed to the gas-retaining layer 10 via the gas feed device 14 in order to keep the amount of gas in the gas-retaining layer 10, or the thickness of the gas layer in the gas-retaining layer 10, and thus the spacing between the liquid-gas contact face and the wall 2, constant.

The gas-retaining layer 10 comprises a multiplicity of protruding elements 26 which are composed of a hydrophobic material or are coated with a hydrophobic material. The protruding elements 26 may be arranged on the gas-retaining layer 10 at regular or irregular intervals along the longitudinal direction L. The gas that emerges via the gas-permeable ply 12 is retained by the protruding elements 26 in the volumes situated between them, such that the liquid 4 substantially cannot ingress into the volumes formed between the protruding elements 26. In particular, the liquid 4 is prevented from wetting the gas-permeable ply 12. The protruding elements 26 shown in FIG. 1 have a turret structure, which is advantageously particularly easy to produce. It is however self-evident that other designs of the protruding elements 26 can also lead to the desired effect. Further advantageous designs of the protruding elements 26 are shown in FIGS. 3 and 4.

Figure 2:
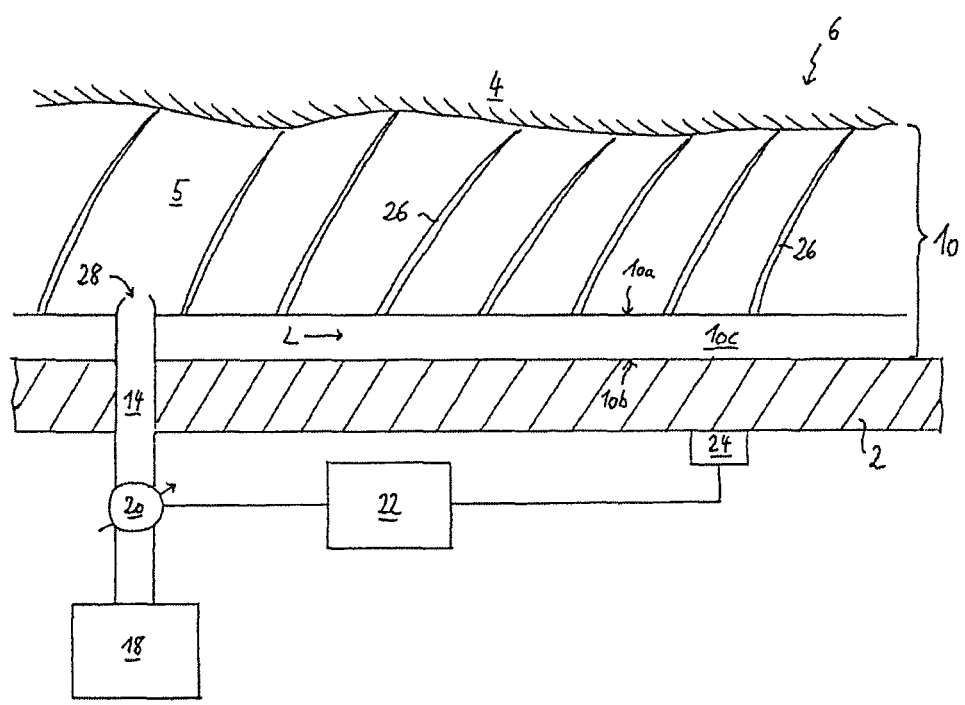
FIG. 2: shows a further embodiment of an arrangement of a preferred surface covering on a body.

FIG. 2 shows a section through a further embodiment of an arrangement of a surface covering 6 on the wall 2 of a body. The gas-retaining layer 10 comprises a multiplicity of protruding elements 26 in the form of thin hairs which have a diameter of approximately 1 μm to approximately 100 μm and which are formed from a hydrophobic material. The protruding elements 26 of the gas-retaining layer 10 are integrally connected to a base 10c, of the gas-retaining layer 10. The body-facing side 10b, of the gas-retaining layer 10 is arranged on and/or fastened to the wall 2 of the body. The fastening of the gas-retaining layer 10 to the wall 2 may be realized for example by adhesive bonding using an adhesive. Furthermore, the gas-retaining layer 10 may preferably also be formed by virtue of a substantially liquid material being applied to the wall and solidifying there in the form of the gas-retaining layer 10.

The embodiment shown in FIG. 2 comprises a gas discharge device 28 which is fluidically connected by means of a gas feed device 14, which is in the form of a duct, to a regulable gas source 18. The regulation of the amount of gas fed to the gas-retaining layer 10 through the gas discharge device 28 is regulated or controlled by means of the valve 20, the regulating device 22 and preferably by means of the sensor device 24. Here, the control or regulation is performed analogously to the embodiment described with reference to FIG. 1.

By means of the gas discharge device 28, the gas is conducted into the intermediate spaces formed between the protruding elements 26. It is self-evident that the gas emerging from the gas discharge device 28 can flow along the longitudinal direction L through the intermediate spaces formed between the protruding elements 26. Since the embodiment shown in FIG. 2 has a gas source 18 which is arranged on a liquid-averted side of the wall 2, the gas feed device 14 extends through the wall 2 at at least one point. It is self-evident that the gas feed device 14 may extend along the longitudinal direction L both on the liquid-facing side of the wall 2 and also on the liquid-averted side of the wall 2 in order to provide a feed to a multiplicity of gas discharge devices 28. Accordingly, the wall 2 may have a multiplicity of passage openings, wherein each passage opening in the wall 2 is assigned a gas discharge device 28. It is thus advantageously possible for gas to be fed to the gas-retaining layer 10 over an area.

FIGS. 3a, to 3f, show different forms of the protruding elements 26. The protruding elements may for example have a form corresponding to the hairs on the leaves of the *Salvinia molesta*, aquatic fern. Said protruding elements 26 comprise a stem 26a, which projects substantially at right angles from the base 10c, from the stem head 26b, of which stem there extends a multiplicity of branches 26c, which diverge from one another and which are joined together by their ends at a common tip point 26d. Owing to the appearance of this protruding element 26, this is also referred to as an eggbeater shape.

FIG. 3b, shows an alternative design of the protruding elements in coronet form, said elements having one, two or more pairs of stems 26a, of concave-convex form, which stems are connected by way of a first end region to the base 10c, and extend, by way of an oppositely situated end region, along a direction substantially perpendicular to the base 10c, wherein the spacing between said end points is smaller than the spacing between the stems 26a, at the middle of the stems.

FIG. 3c, shows a multiplicity of protruding elements 26 in the form of thin hairs which may have a diameter of approximately 1 µm to approximately 100 µm, preferably of approximately 10 µm to approximately 50 µm.

FIG. 3d, shows protruding elements 26 in the form of turrets which, in a sectional view, have a substantially rectangular form. The turrets may however also be of substantially cylindrical, oval, prismatic or similar shape.

FIG. 3e, shows protruding elements 26 in the form of a hair which has a spherical tip end 26f, at that end of the hair 26 which is situated opposite the base 10c.

FIG. 3f, shows protruding elements 26 which have substantially the shape of a frustum which has a spherical tip end 26f, at the tip of the frustum. It is self-evident that, in the embodiments shown in FIGS. 3e, and 3f, provision may also be made of a tip end in the form of a spheroid.

FIGS. 4a, to 4f, show modified protruding elements 26 which substantially correspond to the protruding elements shown in FIGS. 3a, to f. However, the protruding elements 26 in the embodiments shown in FIGS. 4a, to d, have a hydrophilic surface region 26e. The hydrophilic surface region 26e, is preferably arranged or formed on a central region of the surface of the protruding elements 26. The hydrophilic surface region 26e, is in particular surrounded by a hydrophobic surface region of the protruding elements 26. The hydrophilic surface region 26e, is advantageously suitable for achieving that the contact surface between the gas retained in the gas-retaining layer 10 and the liquid 4 with which contact is made is localized at the hydrophilic surface region 26. In this way, it is furthermore advantageously possible for a breakaway of the contact surface between gas and liquid at said locations to be prevented, such that the gas losses from the gas-retaining layer 10 can be reduced.

FIG. 4e, shows protruding elements 26 in the form of a hair which has a spherical tip end 26f, at that end of the hair 26 which is situated opposite the base 10c, wherein a hydrophilic region 26e, is formed on the spherical tip end. It is self-evident evident that the spherical tip end may also be entirely of hydrophilic form.

FIG. 4f, shows protruding elements 26 which have substantially the shape of a frustum which has a spherical tip end 26f, at the tip of the frustum, wherein a hydrophilic region 26e, is formed on the spherical tip end. It is self-evident that the spherical tip end may also be entirely of hydrophilic form. It is furthermore self-evident that, in the embodiments shown in FIGS. 4e, and 4f, provision may also be made of a tip end in the form of a spheroid.

Figure 5:
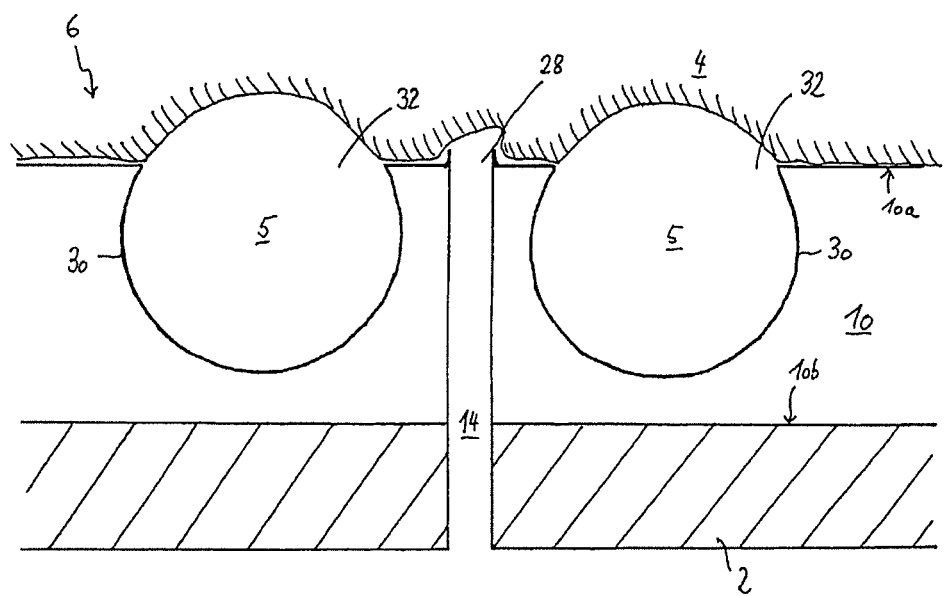
FIG. 5: shows a further embodiment of a surface covering.

FIG. 5 shows a section through a further embodiment of the surface covering 6 which is arranged on a wall 2. Similarly to the embodiment shown in FIG. 2, the embodiment shown in FIG. 5 has a gas discharge device 28 which is connected to a gas feed device 14 extending through the wall 2. The gas-retaining layer 10 which, by way of a body-facing side 10b, is arranged on and/or fastened to the wall 2 comprises depressions 30 instead of the protruding elements. The depressions 30 comprise a passage opening in the liquid-facing side of the gas-retaining layer 10, wherein the diameter of the passage opening 32 is preferably smaller than the diameter of the depressions 30. In particular, the depressions 30 may be of substantially spherical form. It is however self-evident that the depressions 30 may also be of polygonal or oval form.

The material of the gas-retaining layer 10 in which the depressions 30 are formed is a hydrophobic material. It is however self-evident that the internal wall of the depressions 30 in the gas-containing layer 10 can also be coated with a hydrophobic material.

The gas emerging through the gas discharge opening 28 can be stored or retained in the depressions 30 of the gas-containing layer 10. Owing to the surface tension at the contact surface between the gas and the liquid 4 with which contact is made, the contact surface between gas and liquid protrudes beyond the surface of the solid material of the gas-retaining layer 10, that is to say beyond the area of the passage opening 32. In this way, a gas cushion is formed between the liquid 4 and the wall 2, or the solid material of the gas-retaining layer 10, at least in the region of the depressions 30.

Figure 6:
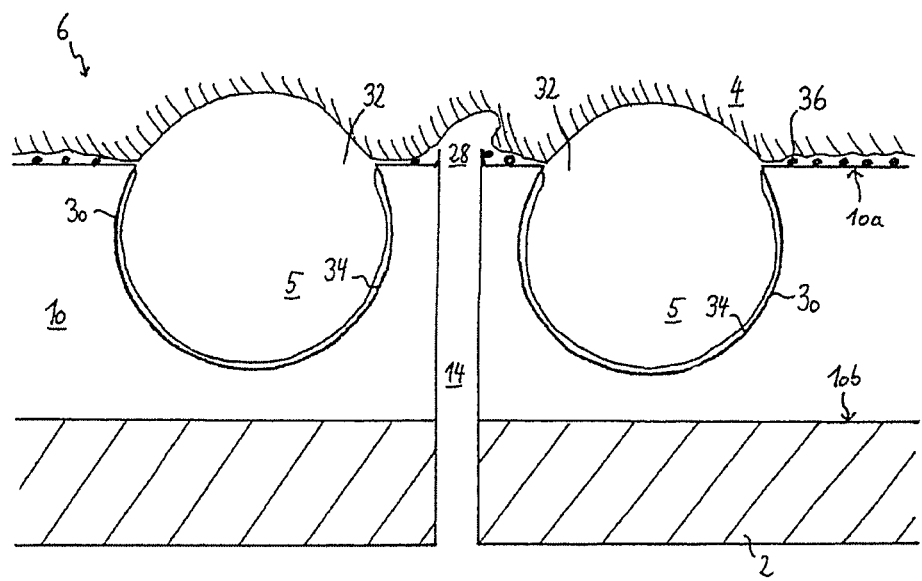
FIG. 6: shows a further embodiment of a surface covering.

FIG. 6 shows a modified form of the embodiment shown in FIG. 5, wherein identical elements are denoted by identical reference signs. The depressions 30 formed in the gas-retaining layer 10 have a hydrophobic coating on the internal wall of the depressions 30, such that the solid material of the gas-retaining layer does not need to be composed entirely of the hydrophobic material. The contact surface between gas and liquid is formed analogously to the embodiment shown in FIG. 5.

To further minimize the flow resistance of a liquid flow along the longitudinal direction L at the contact surface between the liquid and the solid material of the gas-retaining layer 10, the gas-retaining layer 10 may at least regionally have a surface coating 36 with an adhesion-reducing material. The surface coating may for example comprise microparticles or nanoparticles, which form a defined surface roughness in the range from approximately 10 nm to approximately 10 µm.

Furthermore, the surface coating may also have a continuous coating with Teflon or Nano Teflon, which may have a coating thickness of approximately 0.15 nm to approximately 500 nm. Furthermore, to form a surface structure, the surface coating 36 may preferably comprise particles composed of polymers, PDMS, silicon, silicon dioxide, silicon hydroxide, metals, in particular steel and steel fibers, and epoxy resins.

Figure 7:
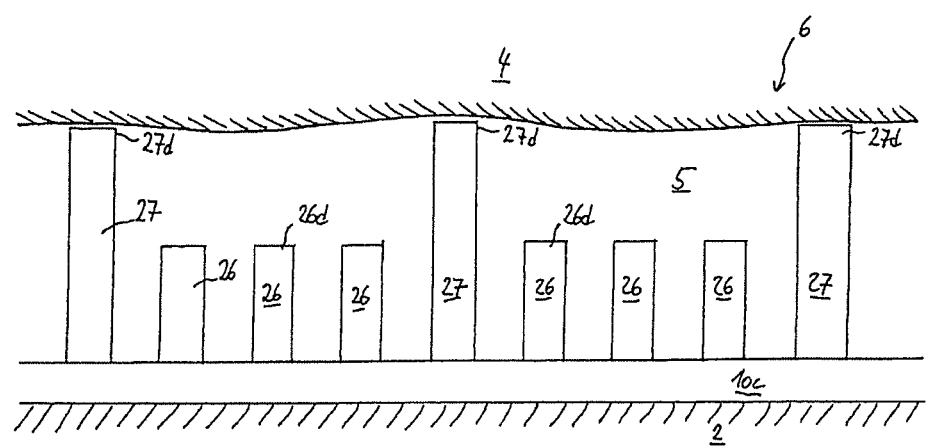
FIG. 7: shows a further preferred embodiment of the gas-retaining layer of a surface covering in a first state.

FIG. 7 shows a structure composed of similar protruding elements 26, 27, wherein the protruding elements 26, 27 are of different sizes. Accordingly, the protruding elements 27 may protrude from the base 10c, in the direction of the liquid 4 further than the protruding elements 26 by a factor of approximately 1.1 to approximately 2. This advantageously results in two structuring planes of the liquid-gas interface. Said structures advantageously have the effect of preventing a complete elimination of the gas, which is retained in the gas-retaining layer 10, in regions of the gas-retaining layer 10.

In the case of low flow speeds of the liquid 4 along the longitudinal direction L or in the case of a small positive pressure of the liquid 4 in relation to the gas pressure within the gas-retaining layer 10, the liquid-gas boundary runs substantially in the form of an envelope of the tip regions 27d, of those protruding elements 27 which protrude further away from the wall 2 than the protruding elements 26. This advantageously gives rise to a substantially continuous air layer which is borne or supported substantially only by the protruding elements 27. The friction between the liquid 4 and the wall 2 is advantageously greatly reduced, for example to a value of less than 5% of the friction value without gas in the gas-retaining layer 10. However, in this state, the gas-retaining layer 10 exhibits a slight tendency for gas losses to occur in the event of pressure fluctuations between the gas 5 retained in the gas-retaining layer and the adjoining liquid 4. In other words, the force per unit of area, or activation energy per unit of area, required for an escape of gas bubbles or for a breakaway of gas bubbles is relatively low.

Figure 8:
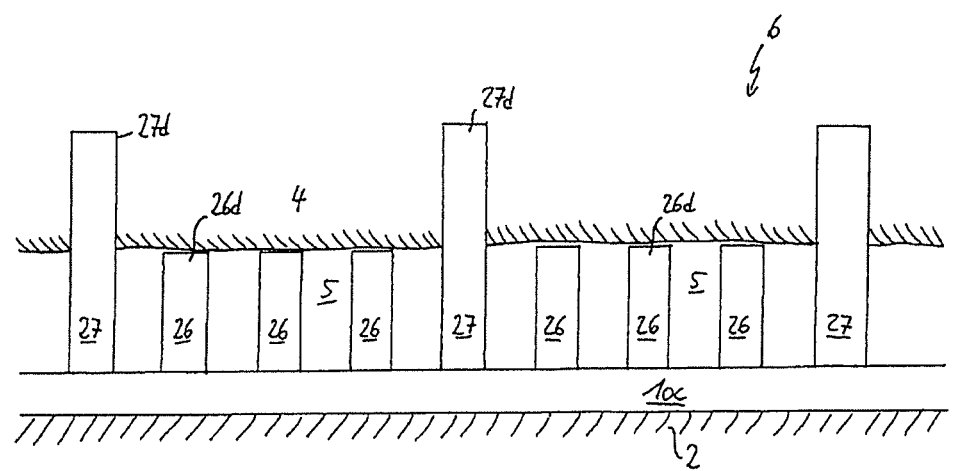
FIG. 8: shows the embodiment shown in FIG. 7 in a second state.

FIG. 8 shows the embodiment shown in FIG. 7 after a loss of gas from the gas-retaining layer 10. The liquid-gas boundary now substantially follows an envelope of those protruding elements 26 which project to a lesser extent in the direction of the liquid 4. The individual gas-filled regions of the gas-retaining layer 10 which are formed by the intermediate spaces between the protruding elements 26 are delimited by the protruding elements 27, which now project regionally into the liquid 4. In particular, an exchange of gas between individual regions formed by the protruding elements 27 can be prevented by the protruding elements 27.

The reduction of the flow resistance is still significant in this state, but is considerably reduced in relation to the state shown in FIG. 7. However, the base 10c, is still substantially entirely, that is to say approximately 90% to approximately 98%, spatially separated from the liquid 4 by the gas 5 in the gas-retaining layer 10. The force required for further gas 5 to be removed from the gas-retaining layer 10 by the flow of the liquid 4 is advantageously greater in the state shown in FIG. 8 than in the state shown in FIG. 7. It is thus advantageously the case that, after an initial gas loss from the gas-retaining layer 10, it is prevented that relatively large amounts of gas are released from the gas-retaining layer.

In the event of yet further gas losses from the gas-retaining layer 10, for example owing to very large pressure fluctuations between the gas and the adjoining liquid 4, a small gas volume remains in the hydrophobic niches between the protruding elements 26. In this way, although the friction-reducing effect of the gas layer with respect to the flow resistance of a liquid 4 flowing along the longitudinal direction L is reduced, it is advantageously the case that only up to approximately 10% of the surface of the base 10c, is in direct contact with the liquid 4, such that there is still substantially complete separation between the wall 2 or the base 10c, and the liquid 4.

Figure 9:
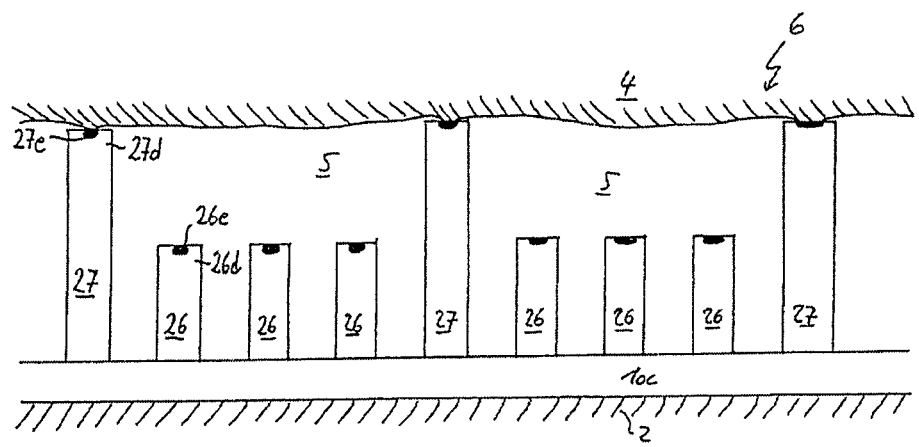
FIG. 9: shows a further embodiment of a gas-retaining layer of a preferred surface covering in a first state.
Figure 10:
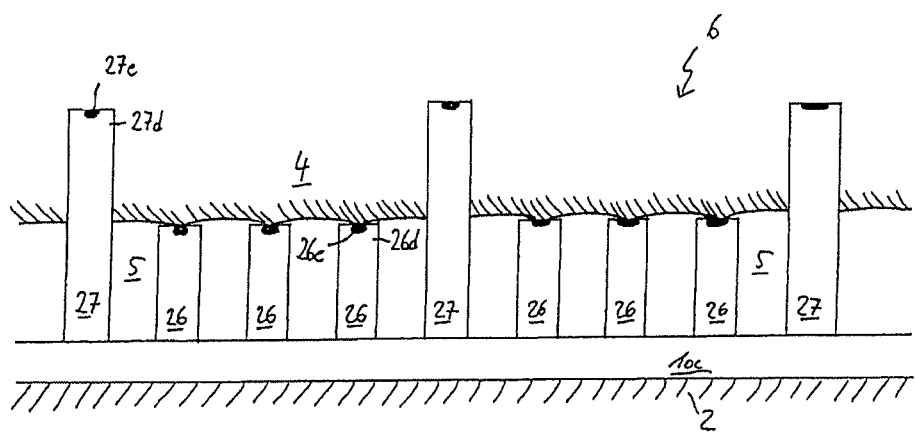
FIG. 10: shows the embodiment shown in FIG. 9 in a second state.

FIGS. 9 and 10 show a modified embodiment of the surface covering 6 shown in FIGS. 7 and 8. Identical elements are therefore denoted by identical reference signs. The protruding elements 26, 27 additionally comprise hydrophilic surface regions 26e, 27e, which permit improved adhesion of the interface between liquid and gas to the associated protruding elements 26, 27, in particular to the tip regions 26d, 27d thereof. This local fixing of the gas-liquid boundary is also referred to as "pinning", such that the hydrophilic surface regions 26e, 27e, can also be referred to as "pinning centers". It is advantageously the case that, through the provision of the hydrophilic surface regions 26e, 27e, the force per unit area required for detachment of gas bubbles from the gas-retaining layer 10 is increased, such that the gas losses from the gas-retaining layer 10 can be reduced. This furthermore advantageously results in a reduced flow resistance at the gas-retaining layer 10, and in improved separation between the liquid 4 and the base 10c, or the wall 2.

It is furthermore preferably possible for further hydrophilic surface regions (not shown) to be formed on the base 10c, between the protruding elements 26e, 27e. Said hydrophilic surface regions prevent a detachment or outflow of gas that has accumulated in the region adjacent to the base 10c. Said gas that has accumulated at the base 10c, advantageously serves as a final gas reservoir which can be eliminated only with difficulty and which in particular covers approximately 60% to approximately 98% of the surface of the base 10c, or of the wall 2 and thus separates the covered surface from the liquid 4. It is advantageously also achieved in this way that the surface of the wall 2 is substantially entirely protected against oxidation or corrosion by a small gas volume. It is furthermore advantageously the case that the gas residues remaining at the base 10c, act as nuclei for the restoration of the gas layer by means of the gas feed device (as shown for example in FIGS. 1, 2, 5 and 6).

It is self-evidently also possible for three or more hierarchical structures of protruding elements to be formed in the gas-retaining layer 10. In other words, in addition to the protruding elements 26, 27 shown in FIGS. 7 to 10, further protruding elements may be provided which project from the base 10 in the direction of the liquid 4 further than the protruding elements 27.

It is self-evident that the protruding elements 26, 27 may be spatially distributed in regular, quasi-regular or random fashion in the gas-retaining layer 10. Furthermore, depressions or recesses which serve as gas pockets, that is to say as a gas reservoir, may be provided at various locations. Of equal suitability to surface coatings with a certain roughness are porous surfaces, whose pores situated at the surface can serve as depressions or gas pockets. For example, the depressions 30 of FIGS. 5 and 6 may also be formed by virtue of the base c being composed of a porous material, wherein the pores are connected, in the region of the passage openings 32, to the exterior of the base 10c.

In the case of the protruding elements 26, 27 being structured so as to protrude in the direction of the liquid 4 by multiple different lengths, it is particularly preferable for the relatively long protruding elements, which determine the position of the liquid-gas interface in FIGS. 7 and 9, to also have a relatively low areal density (number of protruding elements 27 per square centimeter). By contrast, those protruding elements 26 which determine the liquid-gas interface in the situation in which the gas-retaining layer has already lost a not inconsiderable amount of gas, as shown in FIGS. 8 and 10, preferably have a relatively high areal density. It is furthermore preferable for said protruding elements 26 to be of relatively small diameter and to have hydrophilic surface regions, if such are provided, of relatively small size or diameter.

It is preferably possible for the protruding elements 26, 27, which are composed of a superhydrophobic material or have a hydrophobic or superhydrophobic surface, to be provided with hydrophilic surface regions by virtue of the surface of the protruding elements 26, 27 being applied by application or growth of nanoparticulate material, and subsequently or at the same time the nanorough surface thus formed being made hydrophobic with hydrophobic, non-polar end groups or tetrafluoroethylene groups or by adsorption of tetrafluoroethlylene-based molecules or other non-polar or hydrophobic molecules or fats or organic or inorganic oils. Said hydrophobic regions can subsequently be made less hydrophobic in targeted fashion by interaction with a plasma. Those regions whose hydrophobization is reduced, in other words which have hydrophilic function imparted to them, may for example be tips, hair ends, highest elevations, protruding corners, tips and edges, rough surfaces and the like.

If the surfaces of the protruding elements 26, 27 are electrically conductive, for example if electrically conductive polymers are used for forming the protruding elements 26, 27, then an electrical discharge can be utilized for the reduction of the hydrophobization, which electrical discharge, owing to the tip effect, preferably takes place exactly at the tips and at the most intense curvatures and at the furthest protruding surface points, that is to say precisely where the hydrophilic surface regions should preferably be arranged. By means of the discharge, the hydrophobic protective layer is locally destroyed at the discharge points, such that surface regions are formed which are relatively hydrophilic in relation to the hydrophobic regions of the protruding elements 26, 27.

Figure 11:
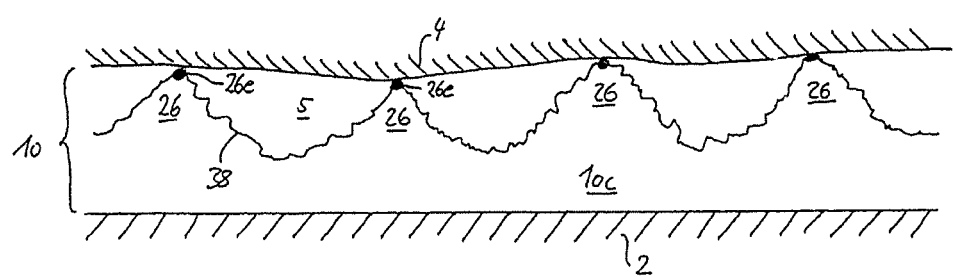
FIG. 11: shows a further embodiment of a gas-retaining layer.

FIG. 11 shows a structure composed of protruding elements 26 of substantially uniform size, wherein the gas-retaining layer 10 has a rough surface 38 which is preferably formed with uniform roughness both in the region of the base 10c, and also in the region of the protruding elements 26. Accordingly, the structures of the rough surface may preferably have a size which is smaller than the size of the protruding elements 26 by a factor of approximately 5 to approximately 20. The rough surface may also have a multimodal roughness distribution encompassing roughnesses from approximately 10 μm to approximately 3 mm, wherein in particular, the protruding elements 26 may be regarded as the greatest roughness within the roughness distribution.

This advantageously gives rise to two or more structuring planes of the liquid-gas interface, as has already been described with regard to FIGS. 7 to 10. The statements made in that regard apply analogously to the embodiment shown in FIG. 11. The rough surface 38 advantageously has the effect of preventing a complete elimination of the gas, which is retained in the gas-retaining layer 10, in regions of the gas-retaining layer 10.

It is furthermore preferably possible for the protruding elements 26 to have hydrophilic surface regions 26e, which permit improved adhesion of the interface between liquid and gas to the associated protruding elements 26. It is self-evident that the rough surface 38 may have a regular, a quasi-regular or a random spatial surface structure.

Figure 12:
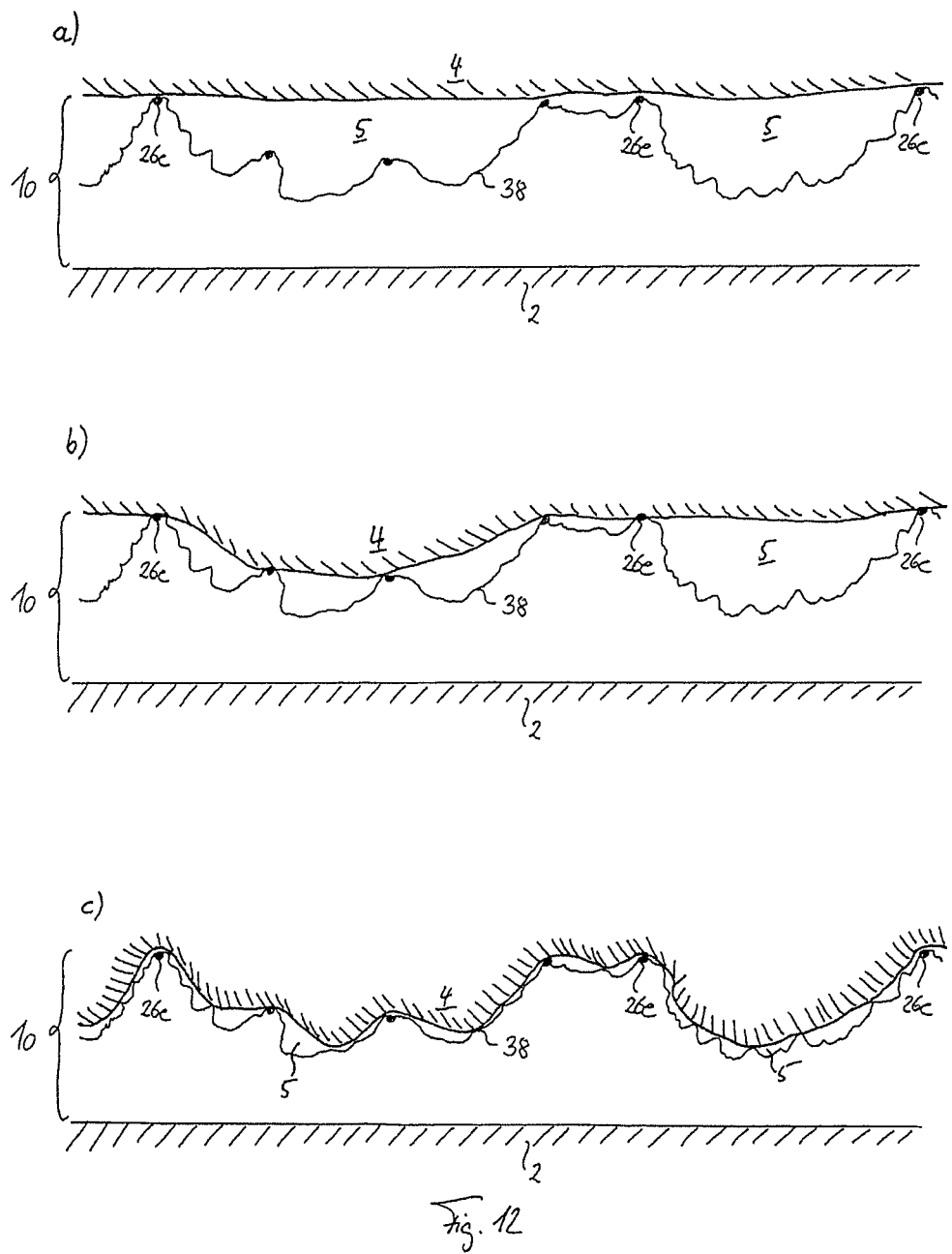
FIG. 12: shows a further embodiment of a gas-retaining layer in different states.

FIGS. 12a, to 12c, show an embodiment similar to the embodiment shown in FIG. 11. In the state shown in FIG. 12a, the gas-retaining layer 10 is completely filled with gas 5. After a loss of gas from the gas-retaining layer 10 has occurred, the liquid-gas interface is displaced as shown in FIG. 12c. As a result of a further loss of gas, the liquid-gas interface is displaced as shown in FIG. 12b. As a result of the loss of gas, although the flow resistance of the wall 2 relative to a flowing liquid 4 is increased, the liquid is substantially prevented from coming into direct contact with the gas-retaining layer 10 or the wall 2, whereby the wall 2 is for example protected against a corrosive influence of the liquid.

FIGS. 13a, and 13b, show fibers 40, the hydrophobic surfaces of which are provided with protruding elements 26, 27. Here, FIG. 13a, shows a structure or arrangement of protruding elements 26 as also shown in FIG. 1. FIG. 13b, shows a structure or arrangement of protruding elements 26, 27 as also shown in FIGS. 9 and 10. The fibers 40 therefore have the properties described with reference to said figures. The protruding elements may optionally be provided with hydrophilic regions 26e, 27e. The fibers 40 may serve as protruding elements of the gas-retaining layer of the surface covering and be formed integrally therewith.

FIGS. 14a, and 14b, show fibers 40 which each have a ring structure of protruding elements 26, 27 corresponding to the structures shown in FIGS. 13a and 13b. It is also optionally possible for hydrophilic regions 26e, 27e, to be formed on the rings 26, 27 that extend along the circumference of the fibers 40.

Figure 15:
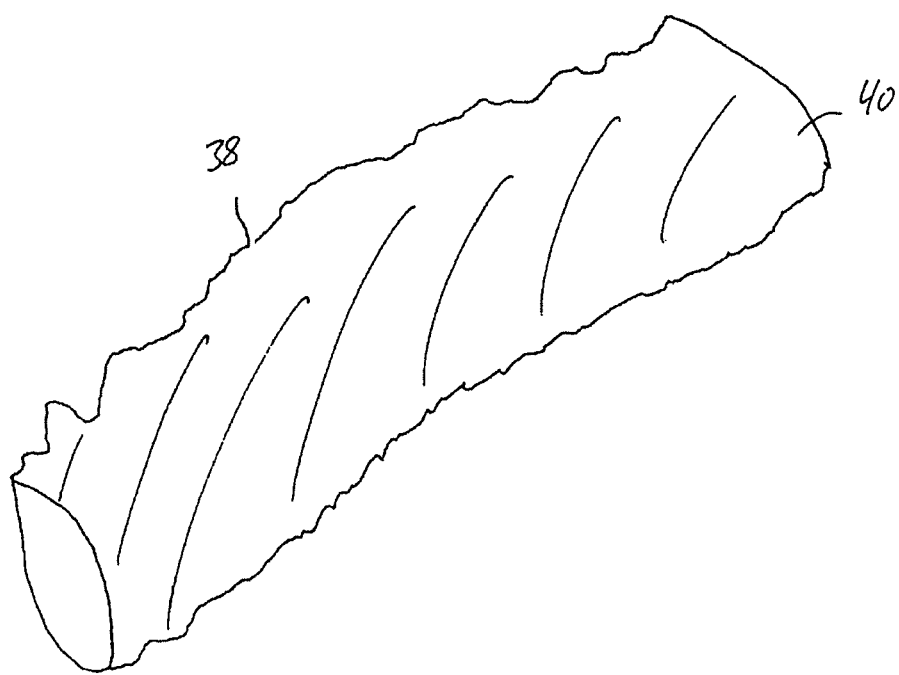
FIG. 15: shows a further embodiment of a hydrophobic, gas-retaining fiber.

FIG. 15 shows a fiber 40 whose hydrophobic rough surface 38 has a structure or arrangement as shown in FIG. 11.

Figure 16A:
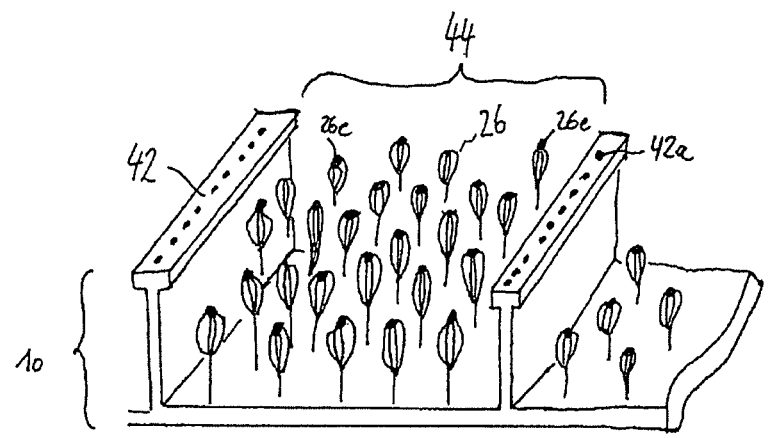
FIG. 16*a*: shows a perspective view of a preferred gas-retaining layer.
Figure 16B:
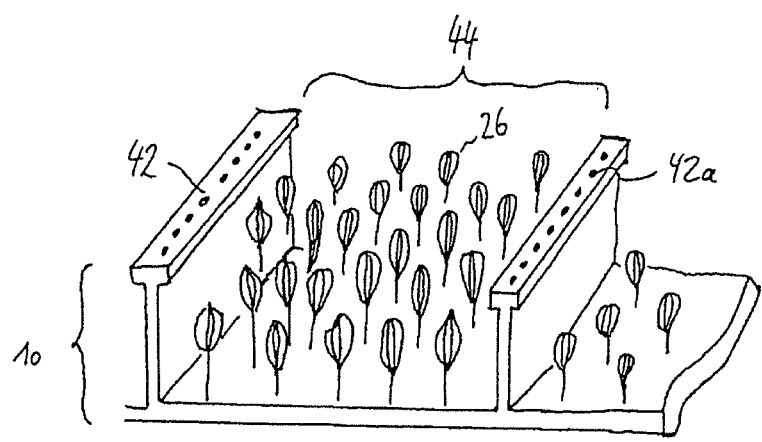
FIG. 16*b*: shows a perspective view of a preferred gas-retaining layer.
Figure 16C:
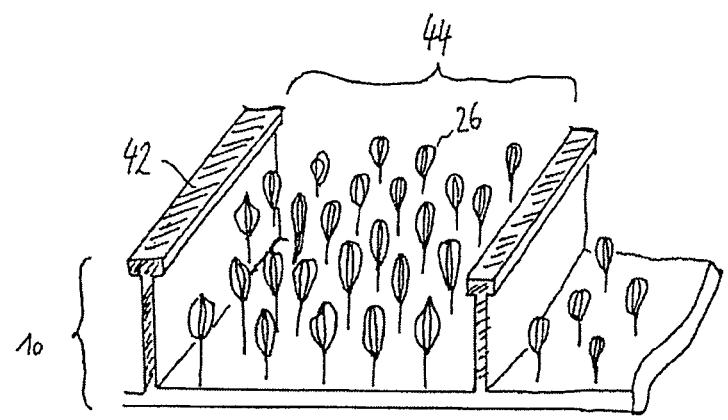
FIG. 16*c*: shows a perspective view of a preferred gas-retaining layer.
Figure 16D:
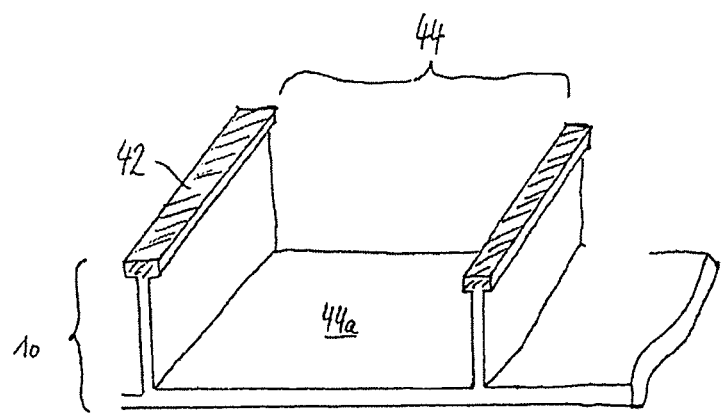
FIG. 16*d*: shows a perspective view of a preferred gas-retaining layer.
Figure 17A:
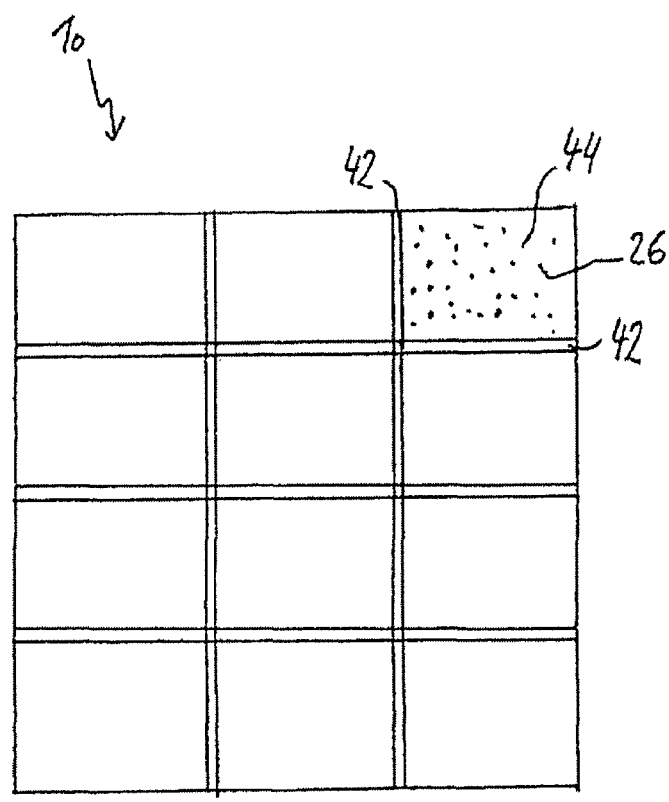
FIG. 17*a*: shows a plan view of the gas-retaining layer shown in FIG. 16, FIG. 17*b*: shows a plan view of a further preferred gas-retaining layer.

FIGS. 16a, to 16d, each show a perspective view of a preferred two-dimensional arrangement of the protruding hydrophobic elements 26 of a gas-retaining layer 10. FIG. 17a, shows a plan view of the preferred two-dimensional arrangement shown in FIG. 16a.

The protruding elements 26 are designed in the form shown in FIG. 3a. It is however self-evident that the protruding elements may also have any other expedient design, for example the designs shown in FIGS. 3 and 4.

As shown in FIGS. 16a, and 17, the two-dimensional arrangement of the protruding elements 26 is divided into individual sub-regions 44, so-called "compartments", wherein each sub-region 44 of the gas-retaining layer 10 comprises a multiplicity of protruding elements 26. The individual sub-regions 44 are preferably delimited with respect to adjacent sub-regions 44 or with respect to the surroundings by a fluid-impermeable partition 42. A fluid is to be understood to mean a gas, a liquid and a mixture of these. Consequently, the partition 42 prevents a liquid flow or a gas flow between the sub-regions 44. In particular, in the presence of a pressure difference between two adjacent sub-regions 44, the partitions 42 advantageously prevent gas from flowing away from one sub-region 44 to the adjacent sub-region and the flow resistance in relation to a liquid with which contact is made thus being locally increased.

In particular, a situation is prevented in which a sub-region 44 is charged with gas beyond its gas capacity by inflowing gas, with gas thereupon passing into the liquid and thus being lost.

The partitions 42 may preferably be formed from the same material as the protruding elements 26. In particular, the gas-retaining layer 10 may be formed with the protruding elements 26 and the partitions 42 together or in one piece. It is furthermore preferable for the partitions 42 of a sub-region 44 to be of substantially the same height as the protruding elements 26 contained in the sub-region 44. It is furthermore preferable for the protruding elements 26 to have hydrophilic surface regions 26e, and/or for the partitions 42 to have hydrophilic surface regions 42a.

As shown in FIG. 16b, it may also be provided that the protruding elements 26 are of entirely hydrophobic form, whereas the fluid-impermeable partitions 42 have hydrophilic surface regions 42a.

Alternatively, the partitions 42 may also be formed entirely or regionally from a hydrophilic material, as shown in FIG. 16a, whereas the protruding elements 26 may be entirely hydrophobic or else may (in a manner not shown in FIG. 16c) have hydrophilic surface regions 26a, correspondingly to the protruding elements 26 shown in FIG. 16a. For example, it may be provided that only those surfaces of the partitions 42 which face toward the liquid are of hydrophilic form or provided with a hydrophilic coating.

Finally, the partitions 42 may also form a sub-region 44 in its entirety, as shown in FIG. 16*d*. In other words, the sub-region 44 comprises no protruding elements. The base 44*a*, of the sub-region 44 preferably has a hydrophobic surface. The partitions may be entirely or regionally of hydrophilic form. For example, it may be provided that only those surfaces of the partitions 42 which face toward the liquid are of hydrophilic form or provided with a hydrophilic coating. In particular, the partitions 42 may be of substantially hydrophobic form, with an areal or linear hydrophilic region being formed on the top edge, that is to say on those surfaces of the partitions 42 which face toward the liquid, it preferably being the case that said hydrophilic region is continuous or is not interrupted by one or more hydrophobic regions, such that the exchange of gas between two adjacent sub-regions 44 is prevented in an effective manner even over the top edges of the partitions 42. The partitions may in this case enclose a self-contained volume of the sub-region 44, such that the gas is retained within said sub-region 44 and substantially cannot escape into an adjacent sub-region.

It is self-evident that the various embodiments of the protruding elements 26 may be combined in any desired manner with the various embodiments of the partitions 42 in order to form a (self-contained) sub-region 44.

In particular, at least one sub-region 44, optionally with a partition 42 or multiple partitions 42, may be formed as a tile or slab that can be fastened to a body. In particular, a tile or slab (these hereinafter also being referred to as air tiles) may have a multiplicity of more than 1000 more than 10,000 or more than 100,000 sub-regions 44. It is advantageously possible for a wall of any size to be equipped or covered with a multiplicity of such tiles or slabs with a gas-retaining layer, which furthermore advantageously results in flexible assembly and has the effect that only a small number of different tiles or slabs need be provided.

The sub-regions 44 are shaped or formed, and attached to the body, such that the longitudinal extent of the sub-regions 44 is smaller along the vertical than along the horizontal that is perpendicular thereto. In particular, if the sub-regions 44 are fastened to the hull of a ship, the longitudinal extent is advantageously smaller along the direction of gravitational force (vertical) than along the water flow direction while the ship is traveling (substantially horizontal), because the gas contained in the gas-retaining layer owing to the then smaller spacing of the partitions 42 the pressure difference between two adjacent sub-regions 44 becomes smaller. At the same time, larger spacings between the partitions along the horizontal permit a minimization of the hydrophilic regions at which friction arises between the water and the ship.

The sub-regions 44 therefore are preferably of rectangular form, as shown in FIG. 17*a*.

Figure 17B:
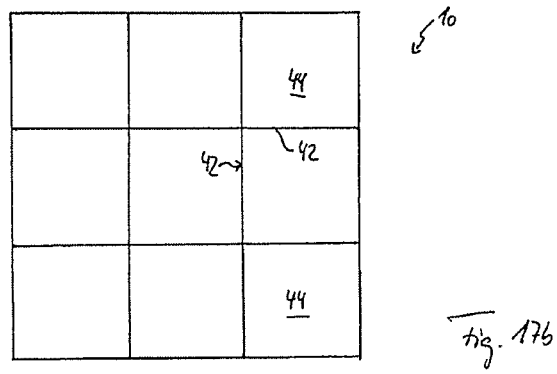
FIG. 17*c*: shows a plan view of a further preferred gas-retaining layer.
FIG. 17*d*: shows a plan view of a further preferred gas-retaining layer.
Figure 17C:
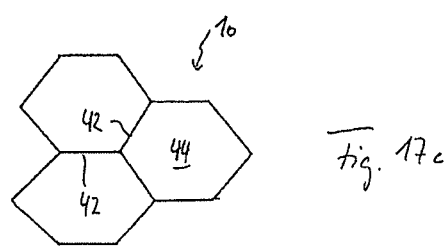
Figure 17D:
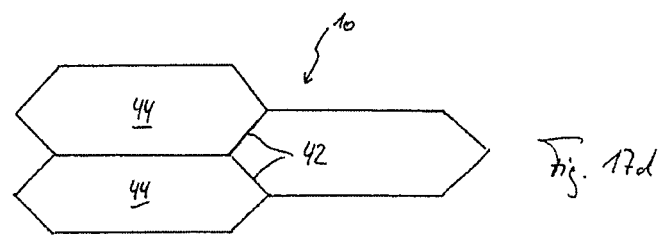

It is however self-evident that the sub-regions 44 may preferably also be of hexagonal or honeycomb-shaped, triangular, square or some other form. FIG. 17*b*, shows a plan view of a preferred embodiment in which the partitions 42 are arranged so as to form square sub-regions 44. FIG. 17*c*, shows a plan view of a preferred embodiment in which the partitions 42, which are of equal length, are arranged so as to form hexagonal sub-regions 44. FIG. 17*d*, shows a plan view of a preferred embodiment in which the partitions 42 are arranged so as to form an elongate honeycomb-shaped or hexagonal sub-regions 44.

Coating for the Protection of Surfaces Under Liquid

In summary, one aspect describes a method for achieving an antifouling action, and protection against corrosion and chemical attack of surfaces under liquid, through the use of a coating which retains a gas layer under liquid.

The surface—for example of the ship, pipe, window, measurement instrument, water vessel etc.—may additionally be equipped with a coating which imparts a chemical or biological antifouling action by way of a toxic or biocide-containing layer or by way of other additives. The advantage lies in the fact that the active substances are released only when required, specifically when the surface is briefly not covered by a gas layer and comes into contact with water or with marine organisms. In this way, the release of toxic or biocidic additives occurs only rarely, specifically exactly when required—with the result that the amount of toxic substances released to the liquid, for example the sea water or fresh water, per unit of time and area can be reduced by many orders of magnitude, which in turn has two advantageous effects:

(i) the release of toxic and biocidic substances is drastically reduced, without a reduction in antifouling action, and
(ii) as a result, the time period for which the reserve of such substances in the ship's paint coat or in the coating lasts before being consumed to such an extent that the antifouling action diminishes is also drastically lengthened, thus also lengthening the service intervals of ships and other installations. This is an enormous advantage in particular in the case of oil platforms, offshore wind parks and other objects that are difficult to access.

An antifouling action can be obtained through the use of air-retaining layers, or more generally gas-retaining layers, under water on their own or in combination with the addition, via the gas layer, of gases or aerosols which are toxic or biocidic or which have an effect on biological fouling by some other means.

The gas layer on its own already forms a barrier that prevents marine organisms from settling. This applies in particular to the settling of bacteria, diatoms, unicellular organisms and microorganisms that form the so-called slime or are responsible for microfouling and which often form the basis for the settlement of larger organisms. If the surface, for example of a ship etc., is surrounded by an air layer and does not come into contact with water, settling and reproduction of said organisms is thus no longer possible.

The surface—for example of the ship, pipe, window, measurement instrument, water vessel etc.—may additionally be equipped with a coating which imparts a chemical or biological antifouling action by way of a toxic or biocide-containing layer or by way of other additives. The advantage lies in the fact that the active substances are released only when required, specifically when the surface is briefly not covered by a gas layer and comes into contact with water or with marine organisms. In this way, the release of toxic or biocidic additives occurs only rarely, specifically exactly when required—with the result that the amount of toxic substances released to the liquid, for example the sea water or fresh water, per unit of time and area can be reduced by many orders of magnitude, which in turn has two advantageous effects:

(i) the release of toxic and biocidic substances is drastically reduced, without a reduction in antifouling action, and
(ii) as a result, the time period for which the reserve of such substances in the ship's paint coat or in the coating lasts before being consumed to such an extent that the antifouling action diminishes is also drastically lengthened, thus also lengthening the service intervals of ships and other installations. This is an enormous advantage in particular in the case of oil platforms, offshore wind parks and other objects that are difficult to access.

The fouling of ships and other watercraft and of water-exposed technical installations, walls, structures etc. by the growth of biological systems is a major technical problem both in fresh water and also in sea water. In the case of the fouling of ships, this is exacerbated by the fact that the fouling considerably increases the friction of the ships in the water and thus also the fuel consumption. The previous solution for protecting against such fouling, that of equipping the ships etc. with toxic paints, lacquers and coatings, is no longer acceptable for environmental protection reasons and is increasingly prohibited, because it can be proven that these highly poisonous ship coatings release considerable amounts of poisonous substances and compounds, in particular heavy metals and the heavy metal compounds, into the sea water.

Non-toxic substances that provide adequate protection against biofouling have however yet to be found. The chances of this happening even in the future are likely to be low, because on the one hand, the systems should prevent biological fouling with marine organisms, but at the same time, said systems specifically must not, by their action, harm the marine organisms, in order that the fauna and flora of seas and coasts are not harmed. The problem addressed thus possibly constitutes an inherent contradiction. It is thus necessary to find a way of selectively compromising the aquatic and marine organisms on the surface without causing significant harm to the organisms in the ecosystem of the surrounding fresh water or sea water. The present invention presents one technical solution for such an approach.

Since, on the one hand, marine organisms and other living organisms that seek to settle on the ship or on other technical surfaces in fresh water and salt water should be hindered from settling and combated, but the measures should act very selectively only at said surfaces and should not harm the biological organisms or marine organisms at other locations, it is self-evident to use a local measure which relates exclusively to the surfaces to be protected and the immediate vicinity thereof.

With the method according to the invention and the device according to the invention, the specified technical problem is solved as follows: since it is technically possible to retain gas layers on a surface under water and introduce gas into said layer in targeted fashion via fabric, porous layers or small openings or nozzles, it is self-evident to equip the surface to be protected with a gas-retaining surface or layer of said type and, at regular or irregular time intervals or when required, that is to say upon the onset or in the presence of biological fouling, to introduce a gas or aerosol (with correspondingly active sol particles) which combats said fouling into the gas layer via the surface. The treatment has no side effects for the ecosystem in particular if the gas or aerosol is only slightly soluble in water or if the compound breaks down after a certain time into non-poisonous constituents or is toxic only in high concentrations or if use is simply made of $CO_2$, for suffocating the marine organisms that have settled on the surface of the ship. The treatment and dosing may in this case be performed manually or automatically.

Optional variants and features relate to a
  combination with sensor means and/or cameras for automatic detection of the extent and/or type of biological fouling, with or without quantitative evaluation of the extent of fouling.
  combination with spatially selective sensor means and/or cameras for automatic detection and localization of the biological fouling, with or without quantitative evaluation of the extent.
  possibility of spatially selective discharge of the active gas or aerosol selectively at the locations at which fouling has taken place or is commencing.
  possibility of spatially selective dosing depending on intensity and type of fouling.
  gas sensor means for spatially resolved detection of the gas composition or of the active substance concentration in the gas layer.
  gas analysis by extraction of gas or aerosol from the layer, also in conjunction with mass spectroscopy, IR analysis, gel chromatography, gas chromatography etc. for spatially resolved and/or temporally resolved analysis of the composition and/or active substance concentration in the gas layer.
  accompanying analysis of dissolved components of the gas or aerosol in the surrounding water in order to remain below specified limit values at all times and at all locations and reliably meet all environmental requirements at all locations and at all times and to manually or—preferably—automatically stop the treatment at any time when required by immediate stoppage of the feed of the active gas or aerosol.

The attainment of an antifouling action may also be achieved through the use of air-retaining layers under water in combination with toxic materials, additives and surface coatings.

The fouling of ships and other watercraft and of water-exposed technical installations, walls, structures etc. by the growth of biological systems is a major technical problem both in fresh water and also in sea water. In the case of the fouling of ships, this is exacerbated by the fact that the fouling considerably increases the friction of the ships in the water and thus also the fuel consumption. The previous solution for protecting against such fouling, that of equipping the ships etc. with toxic paints, lacquers and coatings, is no longer acceptable for environmental protection reasons and is increasingly prohibited, because it can be proven that these highly poisonous ship coatings release considerable amounts of poisonous substances and compounds, in particular heavy metals and the heavy metal compounds, into the sea water.

Non-toxic substances that provide adequate protection against biofouling have however yet to be found. The chances of this happening even in the future are likely to be low, because on the one hand, the systems should prevent biological fouling with marine organisms, but at the same time, said systems specifically must not, by their action, harm the marine organisms, in order that the fauna and flora of seas and coasts are not harmed. The problem addressed thus possibly constitutes an inherent contradiction. It is thus necessary to find a way of selectively compromising the aquatic and marine organisms on the surface without causing significant harm to the organisms in the ecosystem of the surrounding fresh water or sea water. The present invention presents one technical solution for such an approach.

Since, on the one hand, marine organisms and other living organisms that seek to settle on the ship or on other technical surfaces in fresh water and salt water should be hindered from settling and combated, but the measures should act very selectively only at said surfaces and should not harm the biological organisms or marine organisms at other locations, it is self-evident to use a local measure which relates exclusively to the surfaces to be protected and the immediate vicinity thereof.

Ship coatings which are highly effective in preventing fouling with aquatic or marine organisms already exist. The problem with said coatings lies not in the fact that they are toxic—they must or at least should be so in order to be effective in preventing settlement of the marine organisms. The problem with said coatings rather lies in the fact that, as a result of the enduring, long-term contact with the water, the poisonous compounds and heavy metals pass into the sea water.

The method according to the invention and the coating according to the invention address this: the coatings which are effective in preventing fouling are maintained, and the antifouling action is thus ensured and technically proven. Use may be made not only of newly developed antifouling coatings but also of coatings that have been proven over the years and decades. A release thereof to the surrounding water and thus to the surrounding ecosystem is however prevented by virtue of the surface with the antifouling coating being in the form of an air-retaining or gas-retaining surface, and the water thus not coming to contact at all with the surface with the antifouling coating, because a permanent air or gas layer, which in particular persists even under operating conditions, is situated between the—possibly toxic—surface and the water. In the event of gas losses as a result of peak loads, the layer is, in a preferred variant of the method, recharged with gas ("regenerated"): it is technically possible, in accordance with an invention filed in parallel, for a gas layer of said type to be retained on a surface under water and for gas to be introduced into said layer in targeted fashion via fabric, porous layers or small openings or nozzles. It is thus possible, in the event of a loss of gas, for the layer to be immediately regenerated again. The hairs, fibers, pillars, spines or spikes etc., which "span" or maintain the air layer, may but need not imperatively impart an antifouling action themselves or by way of their coating.

Optional variants and features relate to a
  combination with an automatic—preferably spatially selective—sensor means for monitoring against air losses.
  combination with a sensor means of said type with an automatic—preferably spatially selective—replenishment device such that a constant presence of the gas layer is ensured and enduring contact between the sea water and the antifouling coating is prevented.
  accompanying analysis of dissolved toxic components of the coating in the surrounding water in order to remain below specified limit values at all times and at all locations and reliably meet all environmental requirements at all locations and at all times.
  use of the method and of the device even in fresh water.
  use of the method and of the device even with toxic, antibiotic, biocidic, heavy metal-containing and other lacquers, coatings and paints.
  use of the method and of the device even with non-poisonous lacquers, coatings and paints.
  use of the gas layer also for the reduction of friction of the ship, boat, etc.
  use of the stated techniques, methods and devices according to the invention in fresh water or in brackish water or in sea water.
  use of the stated techniques, methods and devices according to the invention not only for the surface of ships but also for the external and internal surfaces of other technical components which come into contact with water, and for corresponding underwater walls, structures etc. and for pipelines, baths etc.

The attainment of an antifouling action through the use of air-retaining layers under water may be realized solely owing to the action of the gas layer or in combination with ultrasound, mechanical movements and deformations, shockwaves, repeated thermal treatment of the surface (for example by electric heating of electrically conductive hairs, fabric etc.) or UV treatment or electrical pulses including gases that are generated upon the electrochemical decomposition of water or salt water or sea water.

The fouling of ships and other watercraft and of water-exposed technical installations, walls, structures etc. by the growth of biological systems is a major technical problem both in fresh water and also in sea water. In the case of the fouling of ships, this is exacerbated by the fact that the fouling considerably increases the friction of the ships in the water and thus also the fuel consumption. The previous solution for protecting against such fouling, that of equipping the ships etc. with toxic paints, lacquers and coatings, is no longer acceptable for environmental protection reasons and is increasingly prohibited, because it can be proven that these highly poisonous ship coatings release considerable amounts of poisonous substances and compounds, in particular heavy metals and the heavy metal compounds, into the sea water.

Non-toxic substances that provide adequate protection against biofouling have however yet to be found. The chances of this happening even in the future are likely to be low, because on the one hand, the systems should prevent biological fouling with marine organisms, but at the same time, said systems specifically must not, by their action, harm the marine organisms, in order that the fauna and flora of seas and coasts are not harmed. The problem addressed thus possibly constitutes an inherent contradiction. It is thus necessary to find a way of selectively compromising the aquatic and marine organisms on the surface without causing significant harm to the organisms in the ecosystem of the surrounding fresh water or sea water. The present invention presents one technical solution for such an approach.

The use of underwater air-retaining or gas-retaining surfaces constitutes the basis for the method proposed here and the device according to the invention. Since it is technically possible, in accordance with an invention filed in parallel, for gas layers to be retained on a surface under water and for gas to be introduced into said layer in targeted fashion via fabric, porous layers or small openings or nozzles, it is self-evident to equip the surface to be protected with a gas-retaining surface or layer of said type and to initially suppress contact between biological systems and the surface to be protected simply by way of the gas layer itself. Such mechanical contact is however required as a starting point for adhesion, and is however prevented by an air or gas layer.

If such contact, and ultimately fouling, however arise for example as a result of impacts, intensive rubbing-together etc., further measures for physically combating the marine organisms may additionally be implemented at regular or irregular time intervals or when required, that is to say upon the onset or in the presence of biological fouling, in order to avoid the use of environmentally harmful chemicals, wherein two methods are particularly expedient: (i) mechanical reduction and elimination of the adhesive contact between the marine organisms and the surface to which they have attached by the movement of elastic hairs, by shockwaves and by ultrasound, and (ii) local heating (in particular resistive or by induction or by microwaves or a combination of said methods) for thermal destruction of the adherent cell layer.

In a preferred variant of the method, the structures (hairs, fibers etc.) that have the effect of retaining the air on the surface are of electrically conductive form and are heated directly. Alternatively or in addition to this, it is possible for the surface, in particular the aerenchyma claimed in an invention filed in parallel with this patent, to be of electrically conductive form and to serve for local heating.

In a further variant of the method, it is also possible for radiation, for example ultraviolet light, to be used in combination with the air-retaining surface.

Optional variants and features relate to the
use of metallic surface structures.
use of the method and of the device even in fresh water.
use of the method and of the device even with toxic, antibiotic, biocidic, heavy metal-containing and other lacquers, coatings and paints.
use of the method and of the device even together with non-poisonous lacquers, coatings and paints.
use of the gas layer also for the reduction of friction of the ship, boat, etc.
coating of ship surfaces—entirely or in part.
use of the stated techniques, methods and devices according to the invention in fresh water or in brackish water or in sea water.
use of the stated techniques, methods and devices according to the invention not only for the surface of ships but also for the external and internal surfaces of other technical components which come into contact with water, and for corresponding underwater walls, structures etc. and for pipelines, baths etc.

In other words, (preferred) subjects of the application can be described as follows:

Subject matter 1 relates to a coating for the protection of a surface or interface, which is permanently or intermittently entirely or partially exposed to a liquid, against corrosion, chemical attack and/or (bio)fouling, characterized in that the surface or interface is coated so as to retain under liquid a continuous or discontinuous, permanently or intermittently existing gas layer under liquid and said gas layer protects the surface against said corrosion, said chemical attack and/or said (bio)fouling.

Subject matter 2 relates to a coating according to subject matter 1, characterized in that the protection against fouling relates to biofouling, in particular in the form of microfouling, macrofouling, the attack of algae, mussels and/or other marine organisms or a combination of these forms.

Subject matter 3 relates to a coating according to subject matter 1 or 2, characterized in that the coating that is used that is permanently or intermittently entirely or partially covered by the gas layer itself comprises biocides, TBT, copper, silver, heavy metals or metal compounds or metal complexes or metal alloys or other fouling-reducing components or admixtures and the release rate of said substances (amount of said substances released per unit of time and area) is reduced by the gas layer.

Subject matter 4 relates to a coating according to subject matter 1, characterized in that the coating for the protection of surfaces is applied to the surface of ships, yachts, boats and other watercraft or to technical installations and structures installed at sea, in particular oil platforms, offshore wind turbines, steel structures, concrete structures or other technical installations installed in a positionally fixed or in a non-positionally fixed manner at sea or in fresh water, buoys, conduits and cables, drive devices, ship surfaces, ship propellers and control devices, windows etc. that are intermittently or permanently under water or are washed over by water, ship rudders, floodlights and other light-emitting optical functional units.

Subject matter 5 relates to a coating according to subject matter 1, characterized in that the gas of the continuous or discontinuous, permanently or intermittently existing gas layer is air, nitrogen, oxygen, carbon dioxide, argon, helium or mixtures of these gases, and/or the liquid is water, salt water, sea water or alcohol or aqueous or alcoholic solutions.

Subject matter 6 relates to a coating according to subject matter 1, characterized in that the coating comprises surface structures, pillars, hairs, studs.

Subject matter 7 relates to a coating according to subject matter 1 or 6, characterized in that the coating surface structures, pillars, hairs, studs or other structures have a height of 0.02 mm to 2 mm and have a hydrophobic surface with or without hydrophilic patches, end or side surfaces.

Subject matter 8 relates to a coating according to subject matter 1, characterized in that the gas-retaining coating is applied to the outside or inside of pipelines or of reaction vessels for chemical reactions or to the inside of vessels for storing liquids.

Subject matter 9 relates to a coating according to subject matter 1, characterized in that the air is retained utilizing the *Salvinia*, effect, the *Notonecta* effect or by means of hierarchically structured surfaces.

Subject matter 10 relates to a coating according to subject matter 1, characterized in that the discontinuous gas layer is composed of a regular, partially regular or irregular arrangement of gas bubbles on the surface coating.

Figure 18:
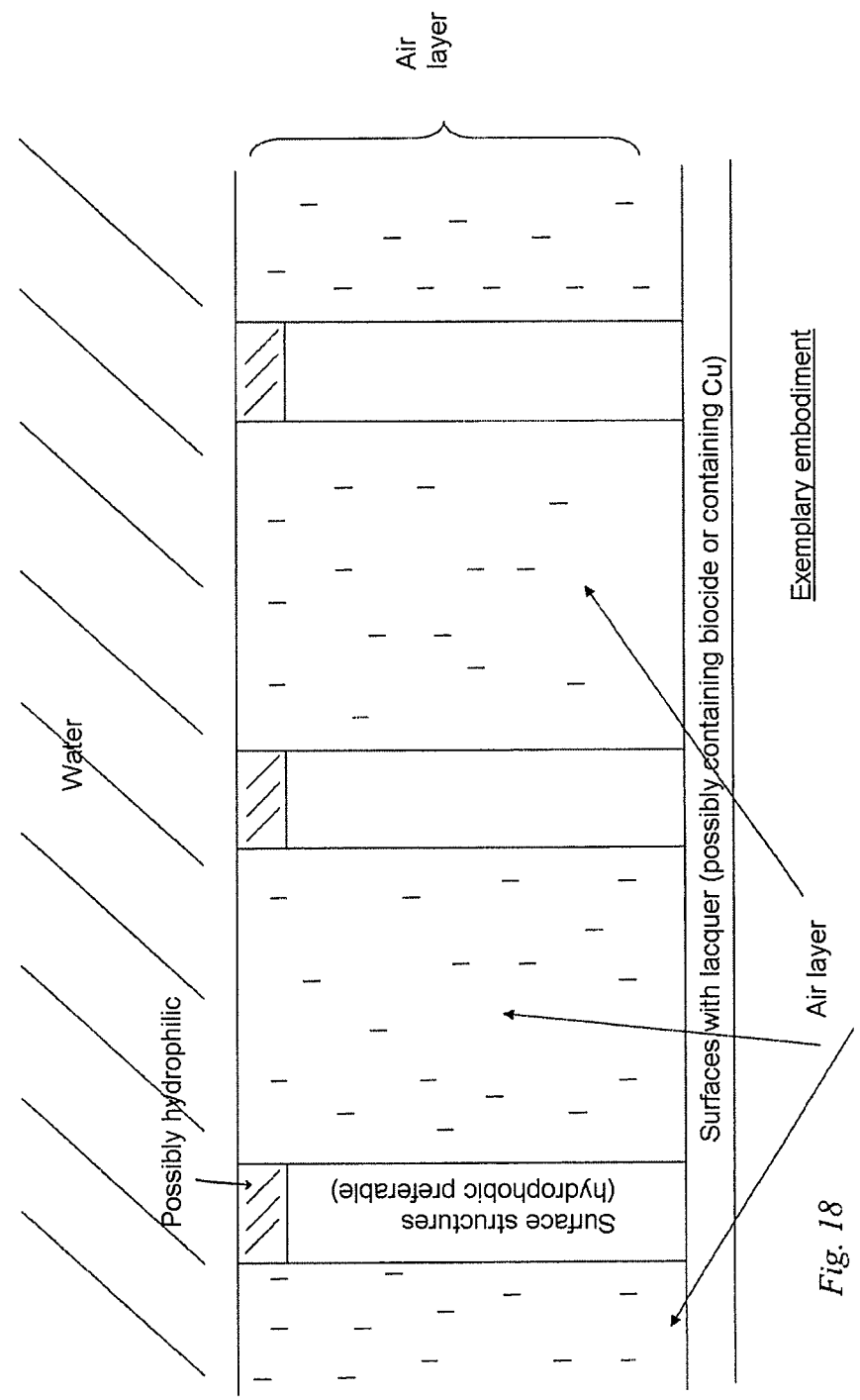
FIG. 18: shows a preferred gas-retaining layer.

FIG. 18 shows a preferred design of a gas-retaining layer which has a multiplicity of hydrophobic projections which optionally have a hydrophilic tip region which, during operational use, faces toward the water. The gas-retaining layer is arranged on a lacquer, which optionally comprises a biocide or copper.

Device for Obtaining a Gas Layer Under Liquid

In summary, one aspect describes gas layers on surfaces under liquid, which are of great technological interest for friction reduction in the case of ships and in pipelines and for protection of the surface against fogging, (bio)fouling, corrosion and chemical attack.

By means of suitable surface structuring, it is possible for a layer of gas or of gas bubbles, which adheres to the surface, to be entrained under liquid. The problem is that a gas layer of said type is stable only for a limited time, and is then lost. This problem is solved by way of a layer that can be recharged with gas.

According to one aspect, the present invention combines
(1) a structured layer that retains a gas layer or gas bubbles under liquid, having
(2) a recharging system composed, for example, of (i) gas feed lines or ducts and nozzles or micronozzles or (ii) a porous membrane, textile, fabric system, felt system, flock system or fiber system or sintered layer or (iii) gas recharging by virtue of (microscopic) gas bubbles generated for example by a sputterer being captured by way of surface hairs or surface structures that preferably have liquid-repelling surfaces, and having
(3) a recharging device composed, for example, of (i) a gas pump or (ii) a self-recharging means, for example utilizing the negative pressure generated by an object moving relative to the liquid, or by a flow, or (iii) a sputterer for the external generation of gas bubbles that are then captured by the structured surface.

Since gas that is lost from the gas layer can be recharged again, the gas layer is maintained, and performs its desired function, on a long-term basis. In one variant, the demand for recharging is measured by way of sensors, and recharging of the layer with gas is performed automatically.

Air layers on surfaces under water are of great technological interest for example and in particular for friction reduction in the case of ships and in pipeline systems and pipelines for the purpose of preventing deposits and the formation of undesired linings on surfaces under liquid, and for obtaining an antifouling action and protection against corrosion and chemical attack of surfaces under liquid, in each case through the use of a coating which retains a gas layer or a layer of gas bubbles or gas pockets under liquid.

By means of suitable surface structuring, it is possible, using textiles, structured and/or functionalized coatings, for example with biologically inspired coatings based on the example of water spiders or *Salvinia molesta*, or *Notonecta glauca*, to entrain a layer of gas, for example of air, under liquid if the surface is immersed under liquid proceeding from the gaseous atmosphere, for example under water proceeding from the air. The problem is merely that such a layer of air, typically 1 μm to 1 mm thick, adheres to the surface only for a limited time, with said gas layer then being lost, normally in the form of the emission of gas bubbles from the gas layer.

Figure 19:
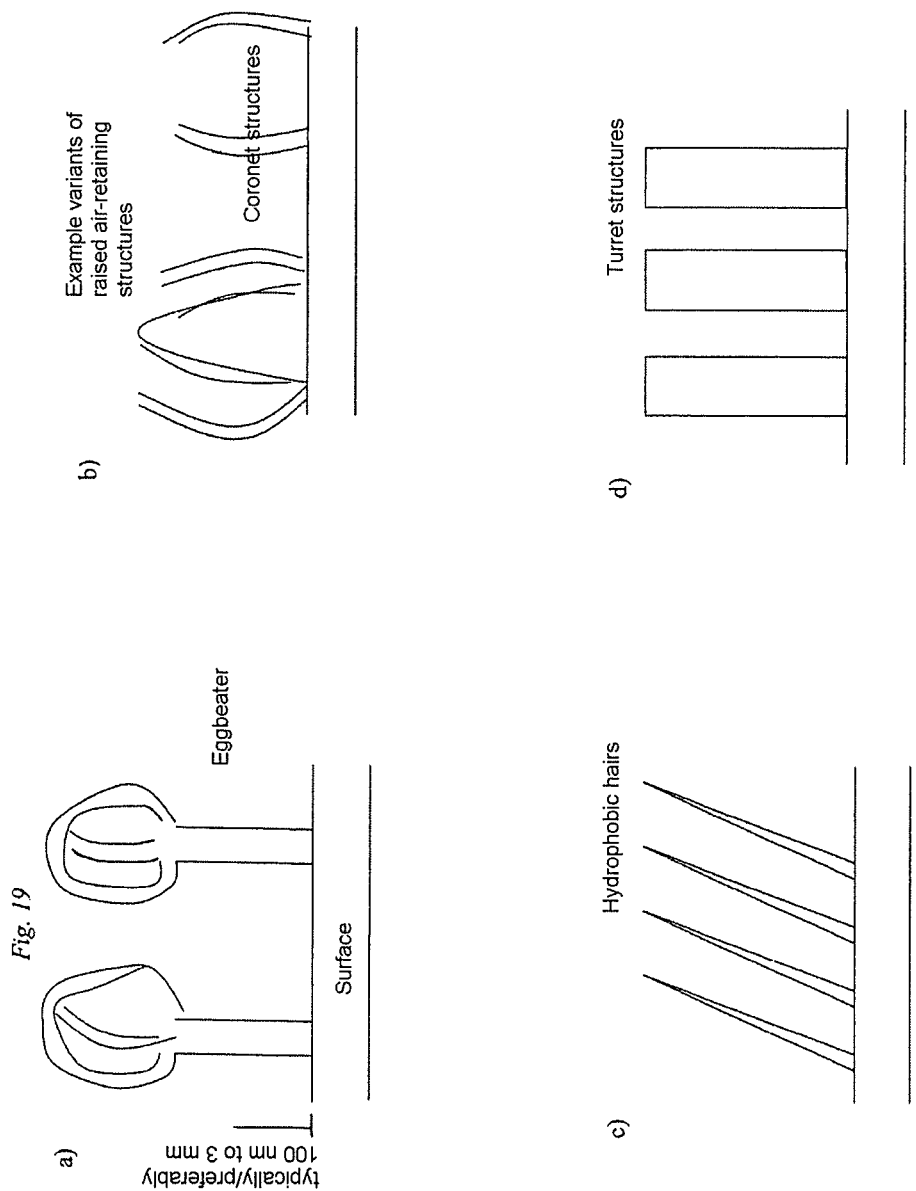
FIG. 19: shows different surface structures.

The present invention now solves said problem by virtue of the device according to the invention combining at least two of the following three things:

(1) a structured layer that retains gas under liquid or a structured layer that retains gas bubbles or gas pockets under liquid (see FIGS. 19 to 21), having (2) a recharging duct system, composed for example of (i) feed lines or ducts for the feed of gas and nozzles or micronozzles or (ii) a porous membrane, textile system, fabric system, felt system, flock system or fiber system or sintered layer or (iii) surface recharging by way of a capturing device for gas bubbles or microscopic gas bubbles generated for example by a sputterer, said capturing device being composed for example of surface hairs or structures which have liquid-repelling surfaces with or without hydrophilic centers and which thus, in the form of protruding hairs, pillars or coronets or by formation of corresponding hollows or depressions with liquid-repelling coating, capture the gas bubbles from the liquid and pin them to the surface or integrate them into an existing gas layer, and having (3) a recharging device, for example in the form of (i) a pump or other active recharging device or (ii) a self-recharging means, for example utilizing the negative pressure generated by a watercraft moving relative to the liquid or by the negative pressure generated by a flow of the liquid relative to a stationary buoy, measurement station, wall etc. (pressure difference is generated by flow of speed $v=0.5 \cdot$density of the liquid$\cdot v^2$) or (iii) a sputterer for the external generation of gas bubbles that are then captured by the structured surface (see point (2)).

Alternatively, it is also possible for a liquid or solid substance to be dosed in which, on its own or by chemical reaction with the surrounding liquid, releases a gas and thus builds up or supplements the gas layer or gas bubble layer again ("replenishing").

Since gas that is lost from the gas layer can be recharged again, the gas layer is maintained on the surface under liquid, and performs its desired function, even on a long-term basis.

The gas layer may also be substituted by a layer composed of individual gas bubbles or gas pockets (air pockets) or by a layer comprising these.

In one variant of the method, the demand for recharging is measured by means of sensors and, to replace the missing gas or the gas lost from the gas layer, overall or selectively in the region with which the respective sensor is associated, gas is fed into the corresponding region again by activating the pump or the sputterer or by opening the corresponding gas valves ("gas recharging on demand"). In this variation of the method, the demand for recharging is thus measured by means of sensors, and the gas that is lost, or the gas that is missing from the layer, is automatically recharged by means of the device according to the invention.

The initial build-up of a gas layer may self-evidently also be performed in this way if required.

A device for retaining an air layer under water, or more generally a gas layer under liquid, is characterized in that the layer can, in the event of a loss of gas, be recharged via a gas-permeable underply, wherein the gas-permeable underply may be a textile underply, some other fabric or felt, a flock material, a porous ceramic layer or ceramic layer suitable for gas diffusion, a metal layer with pores, a metal felt or wire mesh, a semipermeable membrane, a—preferably hydrophobic or superhydrophobic—porous, microporous or nanoporous layer (preferably constructed on the basis of polymers, ceramic materials, metals or composites).

The retention of a gas layer under liquids, for example under water, is of great technical interest. There is great usage potential for such surfaces for example in the field of ship coatings, inter alia for friction reduction and for the attainment of antifouling effects.

Such surfaces have already been produced on a laboratory scale. Among others, the *Salvinia*, effect, hierarchical structuring based on the example of *Notonecta*, and sharkskin and dolphin skin effects have been implemented successfully.

The problem consists in that, under adverse operating conditions (wave surge, wave impact in the case of ship coatings etc.) or over relatively long periods of time, partial or complete, local or extensive gas loss occurs in places or overall.

In the method according to the invention and the device according to the invention, areal elements (which are the subject of this invention) are used together with a device, said elements being such that, after a partial or total loss of gas, they can be recharged with gas again. The device according to the invention for retaining an air layer under water or generally a gas layer under liquid is characterized in that, in the event of a loss of air, the layer can be recharged again via a gas-permeable underply, wherein the gas-permeable underply may be a textile underply, some other fabric or felt, a flock material, a porous ceramic layer or ceramic layer suitable for gas diffusion, a metal layer with pores, a metal felt or wire mesh, a semipermeable membrane, a—preferably hydrophobic or superhydrophobic —porous, microporous or nanoporous layer (preferably constructed on the basis of polymers, ceramic materials, metals or composites).

In one variant of the method, an aerenchyma, such as is described in an invention filed in parallel, is used for the recharging of the gas.

Optional variants and features relate to a
- combination of the above charging of the gas layer ("replenishing") with additional devices for artificially refilling or replenishing the gas layer, for example capillaries, membranes, textiles etc.
- coating of the surfaces with Teflon, polytetrafluoroethylene and the derivatives thereof, in particular also microparticles and nanoparticles of said substances.
- coating of the surfaces with commercially available anti-adhesion sprays or else microparticles and nanoparticles.
- use of surface structures composed of polymers, resins, PDMS, silicon, silicon dioxide and silicon hydroxide, metals, steel and steel fibers, high-grade steel, epoxy.

embossing the surface structures into lacquer, including ship lacquer, with and without subsequent surface functionalization or coating, for example with Teflon or Nano Teflon (preferred layer thickness 0.15 nm to 500 nm).

device as described immediately above, possibly also coupled with measurement and/or control and/or regulating devices which measure and control the state of the gas layer overall or in spatially resolved fashion and automatically trigger gas replenishment if required.

coating of ship surfaces—entirely or in part.

use of metallic surface structures.

use of surfaces with continuous air layer.

use of surfaces which form, build up or retain a regular or irregular pattern of gas pockets or gas bubbles under liquid.

use of hydrophobic or superhydrophobic surfaces and surface structures for the gas-retaining surfaces.

use of hairs, pillars, coronet structures, eggbeater structures, turrets and other raised structures, which are preferably provided with a liquid-repelling coating (with a hydrophobic or superhydrophobic coating if the liquid is water), for the surfaces for the purpose of retaining gas in or between said structures.

use of depressions, hollows, holes and recesses and other recessed structures, which are preferably provided with a liquid-repelling coating (with a hydrophobic or superhydrophobic coating if the liquid is water), for the surfaces for the purpose of retaining gas in or between said structures.

use of a combination of hairs, pillars, coronet structures, eggbeater structures, turrets and other raised structures, and depressions, hollows, holes and recesses, which are preferably provided with a liquid-repelling coating (with a hydrophobic or superhydrophobic coating if the liquid is water), for the surfaces for the purpose of retaining gas in or between said structures.

use of valves and throughflow regulators and actuating elements for the control and/or regulation of the gas feed to the outlet openings which effect the initial filling or refilling of the gas layer.

use as a coating on ships, in flow ducts, in pipes or in chemical reaction vessels.

In other words, preferred subjects of the application can be described as follows:

Subject matter 1 relates to a device and surface coating for the charging and retaining of a gas layer under liquid, composed of (i) a structured surface or surface coating or textile coating which has a structure which makes it possible, when immersed under a liquid, for a continuous or discontinuous gas layer to be retained permanently or at least for a short time (the latter, i.e. the discontinuous gas layer, being composed for example of regularly or irregularly arranged gas bubbles or gas pockets, the gas pockets or air pockets, that is to say small pockets, which are filled with gas under liquid, in the surface topography), wherein the structuring of the surface may be either a regular or irregular topographical structuring ("relief") or a spatially varying chemical functionality (chemical pattern) or a combination of both, and (ii) a device which makes it possible, in the event of a loss of gas, for the surface to be recharged with gas, wherein the gas is fed either (a) from an external source, for example in the form of small gas bubbles flowing past in the liquid, which are then captured by the structured layer or (b) the gas is fed from an internal source from the layer, for example from nozzles or pores or ducts or a line system within or below the structured layer, wherein the gas is fed for example from a gas reservoir, a pressurized gas reservoir, from pressurized gas bottles or with the aid of a pump, or (c) the gas is generated directly in the layer, for example by catalytic and/or electrochemical decomposition of water or (d) the gas is extracted directly from the liquid in the form of dissolved gas present in the liquid or in the form of liquid which evaporates into the gas layer and forms or replaces the gas or a part of the gas of the continuous or discontinuous gas layer or of the gas bubbles or air pockets on the liquid ("self recharging gas layers"), wherein the initial charging or recharging is effected for example by way of a negative pressure in the gas layer, said negative pressure being effected by a relative movement between liquid and gas layer, for example by a ship that moves relative to the water.

Subject matter 2 relates to the use of the device and coating according to subject matter 1, characterized in that said surface or interface, which is permanently or intermittently entirely or partially exposed to a liquid, is protected, by means of a continuous or discontinuous, permanently or intermittently existing gas layer under liquid, (i) against fogging, for example with the interaction of organic and inorganic compounds and the biological and biogenic components from the liquid, and/or (ii) against corrosion and/or (iii) against chemical attack by the liquid and/or gases, molecules, complexes, droplets (in the case of emulsions) or solid particles dissolved in the liquid, and/or (iv) against (bio)fouling, wherein the fouling may refer in particular to biofouling, in particular in the form of microfouling, macrofouling, the attack of algae, mussels, barnacles and/or other marine organisms or a combination of these forms.

Subject matter 3 relates to a coating according to subject matter 1, characterized in that the device and coating for the protection of surfaces is applied to the surface of ships, yachts, boats and other watercraft or to technical installations and structures installed at sea, in particular oil platforms, offshore wind turbines, steel structures, concrete structures or other technical installations installed in a positionally fixed or in a non-positionally fixed manner at sea or in fresh water, buoys, conduits and cables, drive devices, ship surfaces, ship propellers and control devices, windows etc. that are intermittently or permanently under water or are washed over by water, ship rudders, floodlights and other light-emitting optical functional units.

Subject matter 4 relates to a device and coating according to subject matter 1, characterized in that the gas of the continuous or discontinuous, permanently or intermittently existing gas layer is air, nitrogen, oxygen, carbon dioxide, argon, helium or mixtures of these gases, and/or the liquid is water, salt water, sea water or alcohol or aqueous or alcoholic solutions.

Subject matter 5 relates to a device and coating according to subject matter 1, wherein the coating of the surface comprises surface structures, pillars, hairs, studs, which preferably have, entirely or in part, a hydrophobic or superhydrophobic surface, preferably characterized in that said surface structures, pillars, hairs, studs etc. are in turn coated with a thin hydrophobic coating which is preferably 0.1 nm to 2 μm thick, in particular 0.1 nm to 100 nm thick.

Subject matter 6 relates to a coating according to subject matter 1 or 5, characterized in that the coating surface structures, pillars, hairs, studs or other structures have a height of 0.01 mm to 5 mm and have a hydrophobic surface with or without hydrophilic patches, end or side surfaces.

Subject matter 7 relates to a coating according to subject matter 1, characterized in that the gas-retaining coating is applied to the outside or inside of pipelines or of reaction vessels for chemical reactions or to the inside of vessels for storing liquids.

Subject matter 8 relates to a coating according to subject matter 1, characterized in that the air is retained utilizing the *Salvinia*, effect, the *Notonecta* effect or by means of hierarchically structured surfaces.

Subject matter 9 relates to a device and coating according to subject matter 1, characterized in that the surface coating involves textiles, fabrics, fiber composites or gas-permeable coatings, semipermeable membranes or microporous or nanoporous layers, and the gas feed and/or recharging is performed through said pores and ducts in the textiles, fabrics, fiber composites or gas-permeable coatings, semipermeable membranes or microporous or nanoporous layers.

Subject matter 10 relates to a device and coating according to subject matter 1, characterized in that the (re)charging of the surface with a gas layer or the recharging of gas is performed via small nozzles or micronozzles, preferably through nozzles or micronozzles that are embedded into the surface structure of the structured surface, particularly preferably lying in the depressions of the surface layer, for example at the base of the hairs, pillars or other raised surface structures, wherein, in a preferred variant, the structures or pillars themselves may function as gas feed nozzles or micronozzles.

FIG. 19*a*, shows a surface structure composed of eggbeater-shaped elements. FIG. 19*b*, shows a surface structure composed of coronet-shaped elements. FIG. 19*c*, shows a surface structure composed of hydrophobic hairs. FIG. 19*d*, shows a surface structure composed of turret-like elements.

Figure 20:
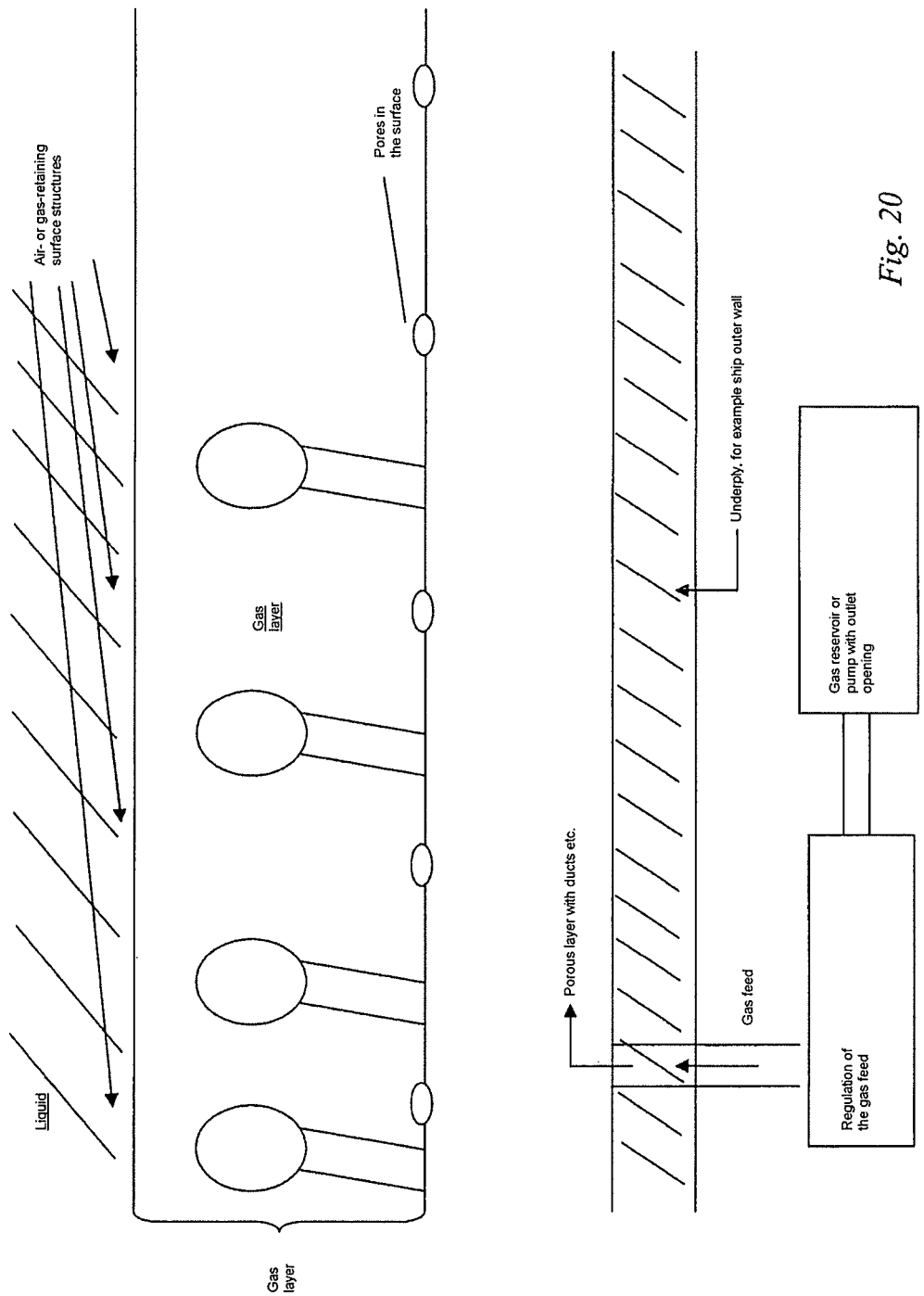
FIG. 20: shows an arrangement of a gas-retaining layer on a ship wall.

FIG. 20 shows an arrangement of a surface covering or of a gas-retaining layer on a ship wall, wherein the gas-retaining layer is fed with gas from the water-averted side.

Figure 21:
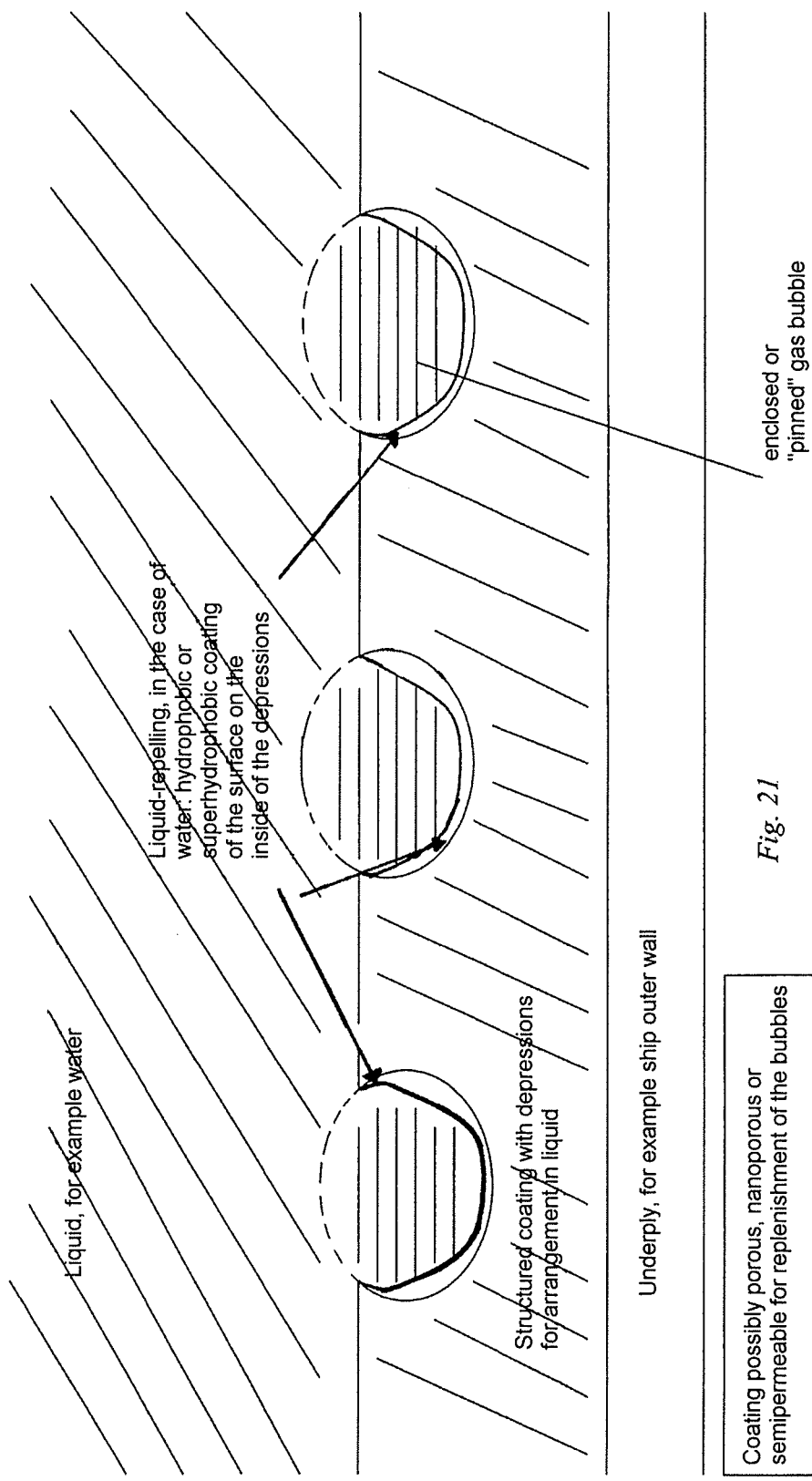
FIG. 21: shows a surface structure composed of depressions.
Figure 22:
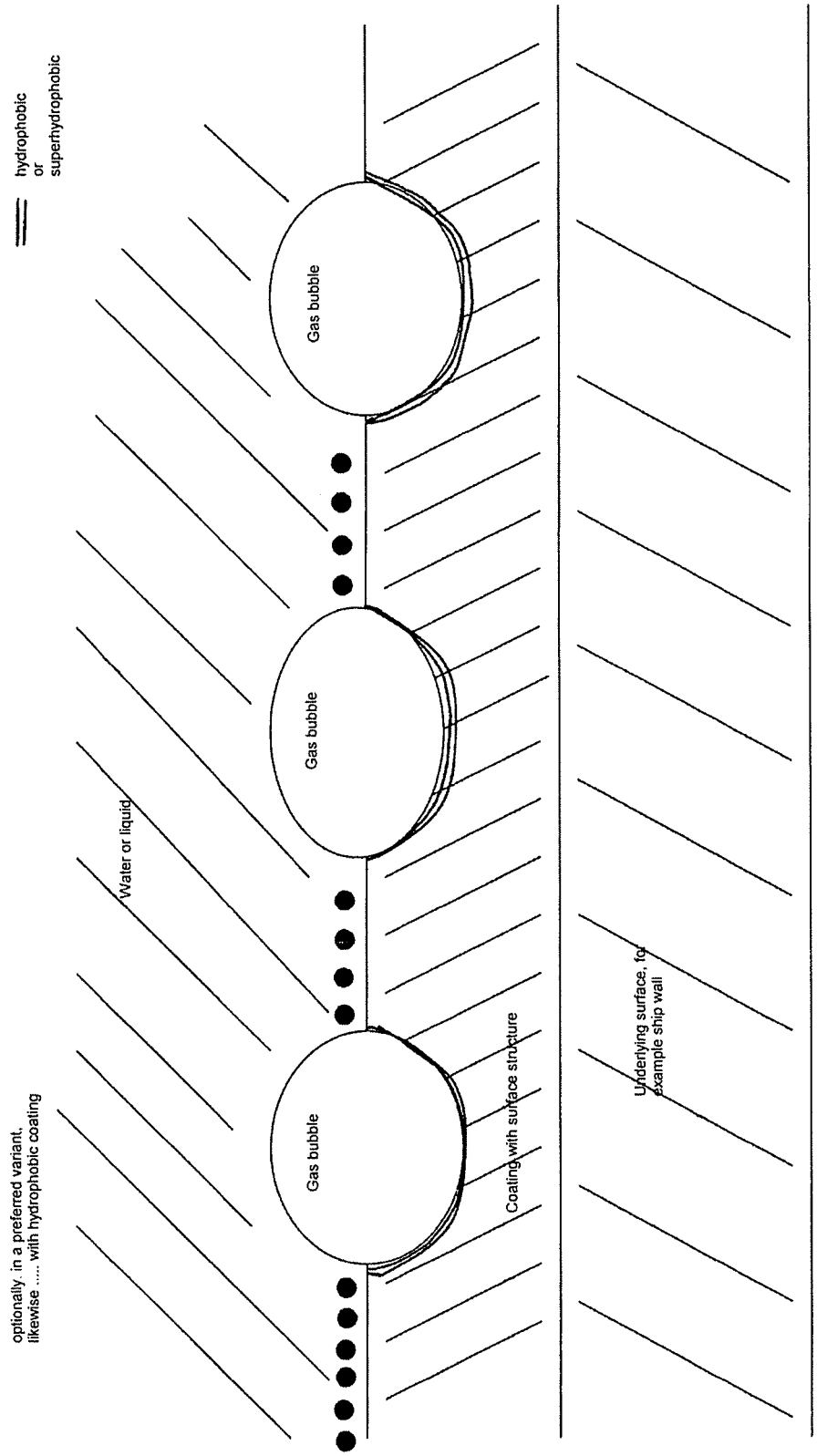
FIG. 22: shows a surface structure composed of depressions with hydrophobic coating.

FIG. 21 shows a surface structure composed of depressions. FIG. 22 likewise shows a surface structure composed of depressions, wherein the surface optionally has a hydrophobic coating.

Functional Elements for Applying a Gas Layer Under Liquid

In summary, one aspect describes gas layers on surfaces under liquid, which are of great technological interest for friction reduction in the case of ships and in pipelines and for protection of the surface against fogging, (bio)fouling, corrosion and chemical attack.

By means of suitable surface structuring, it is possible for a layer of gas or of gas bubbles, which adheres to the surface, to be entrained under liquid. The problem is that such surfaces are often of complex structure and are often difficult to produce over a large area, such as would be required, for example, for a ship coating. Production directly in a shipyard or on the offshore platform etc. is also possible only with difficulty.

Said problems are solved by the application of said structured, gas-retaining surface to a modular carrier or by the structuring of the surface of the carrier itself, wherein said modular carrier may be a rigid or elastic or ductile "tile" or "slab" or foil or foil element, which may preferably be composed of polymer, ceramic, metal (steel, copper, silver etc.), textile, a porous material, a semiconductor material or other materials, and which has a structured surface or hierarchically structured surface for retaining the air layer. The modular carrier itself is then applied, adhesively bonded, screwed, cemented, soldered or welded, or reversibly or irreversibly connected by thermal treatment, to the underlying surface, or fastened in some other way to the surface of the product or object which is to be equipped with a gas layer under liquid.

One aspect relates to the modular attachment of elements with friction-reducing properties or antifouling properties or with properties for retaining gas under liquid or generating or building up a gas layer.

The retention of a gas layer under liquids, for example under water, is of great technical interest. There is great usage potential for such surfaces for example in the field of ship coatings, inter alia for friction reduction and for the attainment of antifouling effects.

Such surfaces have already been produced on a laboratory scale. Among others, the *Salvinia*, effect, hierarchical structuring based on the example of *Notonecta*, and sharkskin and dolphin skin effects have been implemented successfully.

The problem consists in the reversible and also retroactive, inexpensive application of partially complex surface structures.

In the method according to the invention and the device according to the invention, use is made of modular areal elements (which are the subject of this invention) which have the above-stated surface properties and which can be applied to the surface, for example the outside of ships or the inside of pipelines, even retroactively, for example by adhesive bonding.

Optional variants and features relate to the application in the form of tiles, slabs etc. with the desired surface properties;

application of flexible areal elements;

application by reversible or irreversible adhesive bonding;

coating of ship surfaces—entirely or in part;

use of metallic surface structures;

use of surfaces and/or surface structures composed of copper or silver;

use of surfaces and/or surface structures composed of iron or steel;

use of surfaces, surface structures, pillars, spines, fabrics, fiber structures, fiber felts and meshes composed of iron or iron alloys, steel or high-grade steel without or with coating, in the latter case said coating preferably being realized by thin polymer coatings;

use of ceramic surface structures;

use of surfaces and/or surface structures composed of polymers, resins, epoxy;

use of surfaces with continuous air layer;

use of surfaces which form, build up or retain only a regular or irregular pattern of gas pockets or gas bubbles under liquid;

use of said pattern of gas pockets or gas bubbles under liquid as a form of "ball bearing with balls composed of gas or air"—for mechanical guidance and/or for friction reduction;

use as a coating on ships, in flow ducts, in pipes or in chemical reaction vessels;

combination of the above charging of the gas layer ("replenishing") with additional devices for artificially refilling or replenishing the gas layer, for example capillaries, membranes, textiles etc.;

coating of the surfaces with Teflon, polytetrafluoroethylene and the derivatives thereof, in particular also microparticles and nanoparticles of said substances;

coating of the surfaces with commercially available antiadhesion sprays or else microparticles and nanoparticles;

use of surface structures composed of polymers, resins, PDMS, silicon, silicon dioxide and silicon hydroxide, metals, steel and steel fibers, high-grade steel, epoxy;

embossing the surface structures into lacquer, including ship lacquer, with and without subsequent surface functionalization or coating, for example with Teflon or Nano Teflon (preferred layer thickness 0.15 nm to 500 nm);

device as described immediately above, possibly also coupled with measurement and/or control and/or regulating devices which measure and control the state of the gas layer overall or in spatially resolved fashion and automatically trigger gas replenishment if required;

coating of ship surfaces—entirely or in part;

use of metallic surface structures;

use of surfaces with continuous air layer;

use of surfaces which form, build up or retain a regular or irregular pattern of gas pockets or gas bubbles under liquid;

use of hydrophobic or superhydrophobic surfaces and surface structures for the gas-retaining surfaces;

use of hairs, pillars, coronet structures, eggbeater structures, turrets and other raised structures, which are preferably provided with a liquid-repelling coating (with a hydrophobic or superhydrophobic coating if the liquid is water), for the surfaces for the purpose of retaining gas in or between said structures;

use of depressions, hollows, holes and recesses and other recessed structures, which are preferably provided with a liquid-repelling coating (with a hydrophobic or superhydrophobic coating if the liquid is water), for the surfaces for the purpose of retaining gas in or between said structures;

use of a combination of hairs, pillars, coronet structures, eggbeater structures, turrets and other raised structures, and depressions, hollows, holes and recesses, which are preferably provided with a liquid-repelling coating (with a hydrophobic or superhydrophobic coating if the liquid is water), for the surfaces for the purpose of retaining gas in or between said structures;

use of valves and throughflow regulators and actuating elements for the control and/or regulation of the gas feed to the outlet openings which effect the initial filling or refilling of the gas layer;

use as a coating on ships, in flow ducts, in pipes or in chemical reaction vessels.

A device for retaining an air layer under water, or more generally a gas layer under liquid, may be characterized in that the gas layer is divided into individual "compartments"; area elements which, at the edge, are specially protected against the escape of gas in the edge region by zones of relatively dense hair, by hydrophilic webs or pins in a high-density arrangement or by projecting hydrophilic walls, that is to say hydrophilic walls that protrude upward to a certain extent.

The retention of a gas layer under liquids, for example under water, is of great technical interest. There is great usage potential for such surfaces for example in the field of ship coatings, inter alia for friction reduction and for the attainment of antifouling effects.

Such surfaces have already been produced on a laboratory scale. Among others, the *Salvinia*, effect, hierarchical structuring based on the example of *Notonecta*, and shark skin and dolphin skin effects have been implemented successfully.

The problem however consists in that (i) the air escapes at the edges of the coating, and (ii) in the case of extensive surfaces covered with gas layers, considerable pressure differences often exist between different points of the layer. An example is a vertical wall under water. Owing to the hydrostatic pressure, which increases linearly with water depth, the different points of the surface are subjected to different static pressure. If the surface is equipped with a gas-retaining layer and is thus covered by a gas layer under liquid, the gas is forced from regions of high pressure to regions of low pressure. A gas layer of homogeneous thickness is thus not formed, and—even more seriously—the gas layer in the zones of relatively high pressure will ultimately escape.

(iii) a corresponding problem also exists if the pressure gradient in the layer is not based on hydrostatic pressure but is based on dynamic pressure differences for example owing to different flow speeds of the surrounding liquid at different locations on the surface.

In the method according to the invention and the device according to the invention, the problem is solved in that the gas-retaining surfaces do not retain a continuous gas layer, and instead the gas layer is divided into individual "compartments"; segments which are sealed against gas flow and of which each is small enough—in particular, in the presence of gravitational pressure gradients, has a vertical extent small enough—that the pressure differences within a compartment are small enough to avoid a considerably inhomogeneous distribution of the gas within a compartment, that is to say to avoid considerable differences in air layer thickness.

In a further method according to the invention and the further device according to the invention, it is furthermore the case that the edges of the gas-retaining surface and the edges of the individual compartments are protected, by special measures, against an escape of gas at the edges, wherein said measures may consist in an increase in the areal density of the gas-retaining structures, in an enlargement of the hydrophilic pins, in the use of linearly extensive structures, in a special hydrophilic coating of the delimiting webs, hairs or pins.

Optional variants and features relate to the application in the form of tiles, slabs etc. (hereinafter also referred to as "air tiles") with the desired surface properties;

application of flexible areal elements;

application by reversible or irreversible adhesive bonding;

coating of ship surfaces—entirely or in part;

use of metallic surface structures;

use of surfaces with continuous air layer;

use of surfaces which only form, build up or retain a regular or irregular pattern of gas pockets or gas bubbles under liquid;

use of said pattern of gas pockets or gas bubbles under liquid as a form of ball bearing with balls composed of gas or air—for mechanical guidance and/or for friction reduction;

use as a coating on ships, in flow ducts, in pipes or in chemical reaction vessels.

The novel concept of the air tiles:

tiles and foils or foil elements that retain a gas layer under liquid;

can be applied in modular, flexible fashion to smooth or rough, curved or non-curved surfaces of any size;

can be easily applied to existing surfaces;

tiles with an air layer—or more generally: a gas layer—under liquid;

modular;

can be easily applied to existing surfaces;

tiles, that is to say areal elements of any desired shape, which retain or build up a gas layer under liquid, for example under water;

and arrangements of such elements;

and apparatuses, for example ships or pipelines, which have such elements on their outer or inner surfaces;

tiles, that is to say areal elements of any desired shape, which retain or build up a gas layer under liquid, for example under water;

and arrangements of such elements;

including areal elements which, in a periodic arrangement, completely cover the areas;

and apparatuses, for example ships or pipelines, which have such elements on their outer or inner surfaces;

no large pressure gradient within a tile;

hydrostatic pressure difference within a tile is at most density of the liquid×height of the tile×gravitational acceleration;

problems owing to edge effects are solved by compartmentalization and edge sealing within a tile;

in the case of systems with rechargeable gas layer, feed lines or gas charging systems may be integrated into the module or the modular carrier;

modular concept;

simple assembly;

simple exchange of damaged tiles;

owing to flexible carrier, can also be applied to curved surfaces;

reversible coating;

adhesive bonding and debonding have already been technically achieved;

requires no particular ship construction;

requires no specific underlying surface;

highly suited to the enormous refurbishing market;

and for new ships.

The novel concept of the air tiles:

even partial coatings are possible;

short assembly times;

suitable for a wide variety of ship sizes;

upscaling is thus very easily possible;

it is not necessary to produce large surfaces, only large unit quantities of individual tiles or foil elements or foil rolls;

a wide variety of materials are possible for the air-retaining layer, for the carrier material and for the adhesive;

this permits simple adaptation to the ambient conditions (fresh water, salt water etc.);

individual elements, preferably 0.2 cm×0.2 cm up to 10 cm×10 cm, within the surface of a carrier element ("air tile" or "tile") are partitioned off, as an air-retaining surface unit, by means of a terminating—preferably hydrophilic—edge;

concept: creating compartments for partitioning so as to prevent air exchange between the compartments;

10 cm×10 cm up to 100 cm×100 cm as preferred size for the air tiles (with assembly of compartments within each tile) and with assembly of the air tiles to cover larger areas;

friction reduction with modular coating, spatially selective, where and as required;

air retention under real operating conditions;

owing to the modular approach, simultaneous mounting of different types of tiles or foils or foil elements with different coating at different points of the object to be coated, for example of the ship, is possible in accordance with locally required function and locally prevailing pressure and flow conditions (for air retention) and light conditions (relevant with regard to biofouling).

Modular concept:

simple assembly;

simple exchange of damaged tiles;

further advantage: decoupling of production location of the surface coating from the location at which said surface coating is applied to the surface, for example the ship. This is important because the production of the surfaces, which are partially of complex structure, for retaining gas under liquid requires a special production process which cannot readily be implemented by way of production facilities adjacent to every ship to be coated or even at sea in the offshore sector.

further advantage: compact production plants because there is no need to produce extremely large surfaces, only small tiles or foil elements or foil webs.

further advantage: the size of the surfaces to be covered is not limited by the size of the production plant: with an adequate number of small tiles, surfaces of any size can be covered.

consequential advantage: there is no need for the production process to be scaled up to surfaces larger than the individual tile or the individual foil web or the individual foil element (=one surface element of a certain size and shape).

non-toxic;

inexpensive;

low weight;

visually appealing and can be adapted to the appearance of the ship (color, livery etc.);

non-combustible and non-flammable;

can be easily combined with tiles based on other friction-reducing technologies (tiles with shark skin/dolphin skin, hydrophobic or superhydrophobic surfaces etc.);

no particular expert knowledge required during the attachment process;

no special equipment required;

inexpensive mass production of a standard product at the factory rather than cumbersome special coating using special machines on location at the ship.

Objective: persistent air layers under water

Content: air retention on artificial surfaces

Air retention:

permanent or temporally limited under negative pressure in the flow gradient.

Advantages and properties modular production, adaptable to any object sizes and object shapes, surfaces can be covered completely;

permanent air retention;

air retention under negative pressure;

air retention in the flow gradient.

Figure 23:
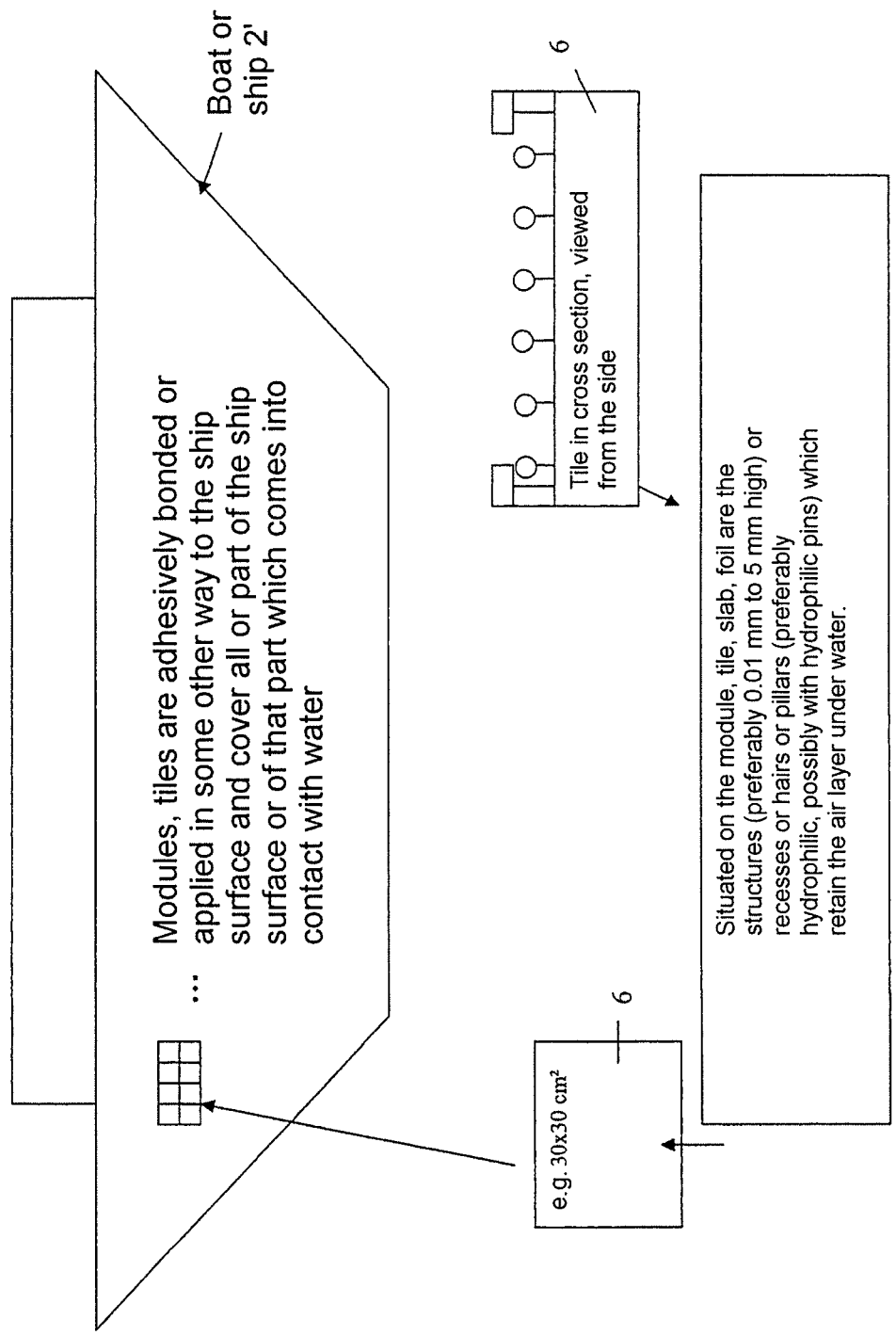
FIG. 23: shows a ship whose wall is equipped with a multiplicity of tiles with a gas-retaining layer.

FIG. 23 shows a ship 2', the wall of which is provided with a multiplicity of tiles 6 or slabs ("air tiles") such that there, a gas-retaining layer protects the ship wall against the influence of the water.

Figure 24:
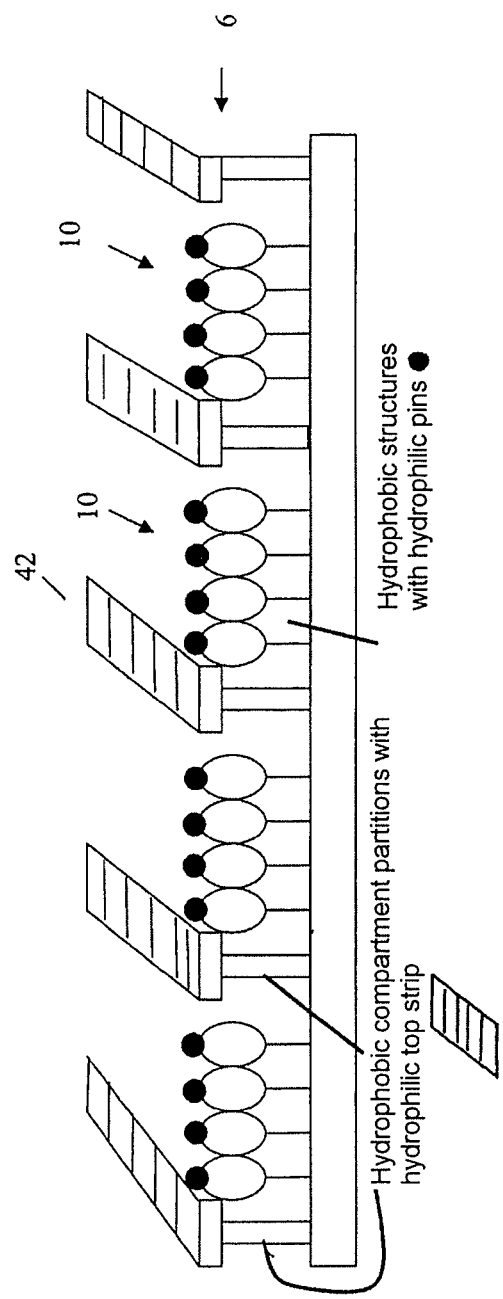
FIG. 24: shows a surface covering, or tile, which has partitions 42.

FIG. 24 shows a surface covering or tile 6 which has partitions 42 for fluidically separating a multiplicity of regions of the gas-retaining layer 10 from one another.

Figure 25:
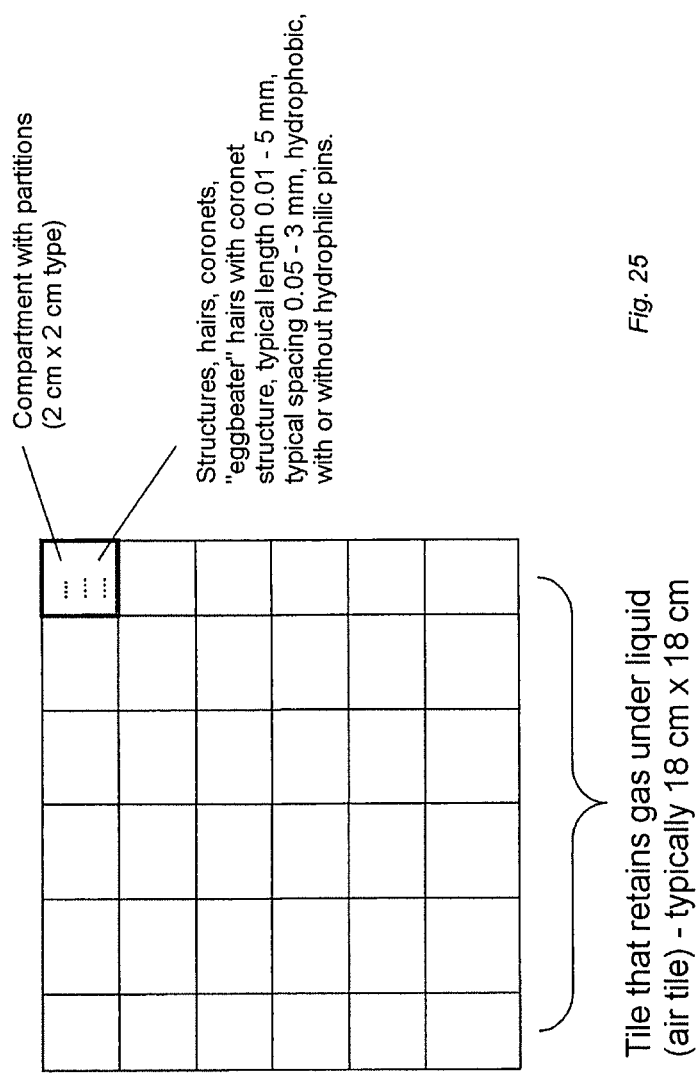
FIG. 25: shows a tile or slab.

FIG. 25 shows a tile or slab ("air tile").

Figure 26:
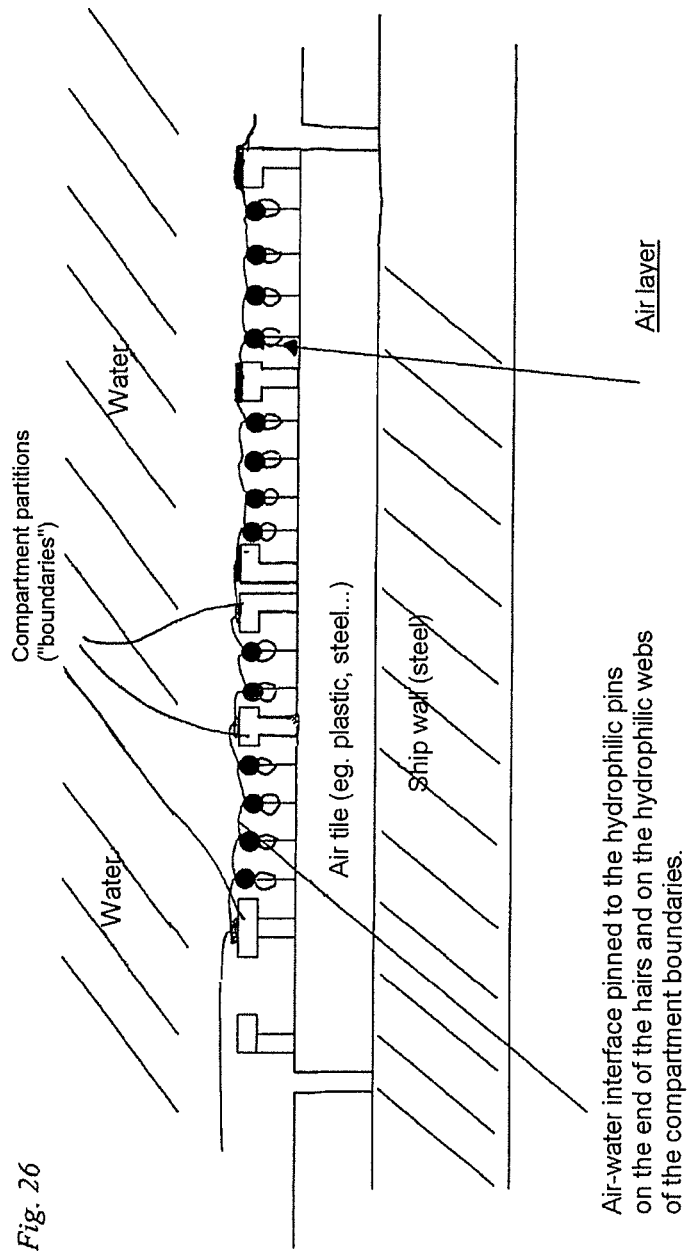
FIG. 26: shows a section through a ship wall equipped with tiles.

FIG. 26 shows a section through a ship wall that is provided with tiles 6 or slabs ("air tiles").

Use of Air-Retaining or Gas-Retaining Surfaces

In summary, one aspect describes the use of air-retaining or gas-retaining surfaces under water or some other liquid for the purpose of protecting surfaces against corrosion by the liquid or by components, ions or additives and constituents contained in the liquid—including possible reactive solid particles contained in the liquid.

The protection of surfaces against corrosion is of great technical significance. In particular, solid body surfaces, for example metal surfaces under liquid, for example under water, in particular under salt water, are subject to intense corrosion attack. Providing corrosion-preventing lacquer coatings is expedient here, though this is also associated with considerable disadvantages. These include in particular: (i) over time, lacquers become brittle and cracked and become detached, (ii) they often release toxic constituents into the water, (iii) they often exhibit only limited long-term temperature resistance in applications in the range of relatively high temperatures, and (iv) they are—in particular in the case of use under chemically aggressive media such as acids, brines, strong oxidants or reductants—often themselves not adequately resistant to the liquid medium.

With the method according to the invention and the device according to the invention, said four problems are solved in that the liquid medium is prevented entirely from coming into contact with the vessel or with the pipe or other wall, and instead, use is made of containers and vessels composed of air (or some other gas), that is to say, between the actual vessel wall or pipe wall or other boundary, a layer composed of a gas (which is preferably inert in the given chemical environment) is applied, as a gas layer, to the surface, and thus contact between reactive liquid and vessel wall is prevented, wherein, for the application of a persistent gas layer to the surface, a gas-retaining coating is applied, for example utilizing the *Salvinia*, or the *Notonecta*, effect.

Optional variants and features relate to the
utilization of the gas layer also for gas exchange, for introduction of reaction gases (reagents), for the removal of reaction products or for cleaning and flushing purposes.
application of flexible gas-retaining surface elements.
coating of ship surfaces—entirely or in part.
use of surfaces with continuous air layer.
use of surfaces which form, build up or retain only a regular or irregular pattern of gas pockets or gas bubbles under liquid.
use of said gas layer or said pattern of gas pockets or gas bubbles under liquid also for friction reduction.
use as a coating on ships, in flow ducts, in pipes or in chemical reaction vessels.

The production of surfaces which retain gas under liquid using a periodic or non-periodic array of metallic pins (small metal bars or spikes or wires which stand perpendicular or obliquely to the surface to which they have been applied), composed preferably of high-grade steel, with or without capillary for the refilling of the gas layer, with or without utilization of the *Salvinia*, effect utilizing a hydrophilic region on the end of an otherwise hydrophobic metal pin.

The retention of a gas layer under liquids, for example under water, is of great technical interest. There is great usage potential for such surfaces for example in the field of ship coatings, inter alia for friction reduction and for the attainment of antifouling effects.

The problem consists in technically implementing such surfaces, based on the example of *Salvinia molesta*, or *Notonecta glauca*, for example, such that they exhibit long service lives under the mechanically and chemically demanding operating conditions of deep-sea shipping, for example:

it is thus necessary to ensure mechanical stability of the coating in the presence of intense swell and wave surge and corresponding corrosion resistance under the corrosive action of the sea water.

An ideal material that meets the two stated conditions is high-grade steel. Therefore, in the method according to the invention and the device according to the invention, corresponding layers that retain air under water are designed such that main components of the layer, preferably also the hairs, pillars or other structures applied to the surface for the purpose of retaining the air layer, are composed of steel, preferably rust-resistant high-grade steel.

A further advantage is that, in one variant of the method, the air-retaining structures may be formed entirely or partially as high-grade steel cannulas, on the side or at the end of which there is situated an opening via which the air or gas layer can be refilled ("recharged") with gas in the event of a loss of gas.

Further variants or features relate to the
application of metal chips or steel chips.
application of arrays of small metal pins.
use of steel, iron and iron alloys, or else other metals or carbon fibers, as air-retaining structures.
use of metal felts or metal wire meshes or fabrics.
use of metallic surface structures by embossment or other machining of metallic surfaces.
use of embossed or otherwise structured metal sheets or metal foils, including the use of thin and extremely thin steel sheets.
use of surface structures that form, build up or retain only a regular or irregular pattern of gas pockets or gas bubbles under liquid, rather than a continuous gas layer.
use for friction reduction in liquid.
use as a coating on ships, in flow ducts, in pipes or in chemical reaction vessels.

Use of air-retaining or gas-retaining surfaces under water, or some other liquid, for protection against adhesion to the solid wall or vessel surface in the event of solidification of the liquid, for example in the event of freezing of water.

Vessels into which a medium is to be introduced for solidification, for example water, for example in an icemaker or in the ice compartment of a refrigerator, normally have two problems: (i) the thermal contraction or expansion during the solidification process and (ii) the adhesion of the solidified medium to the vessel wall.

In the method according to the invention and the device according to the invention, the adhesion problem is solved by virtue of the vessel being equipped with a gas-retaining coating and the liquid itself thus not coming into contact with the vessel or pipe walls. If the gas-retaining structures are made so as to be elastic—preferably so as to be inclined relative to the surface—and also long enough that, during the phase change, they can compensate for the expansion or contraction by deformation of the structures and by a change in their angle of inclination, and the simultaneous change in the gas volume of the layer, problem (i) is also solved. Use may alternatively be made of elastic vessel walls, composed for example of rubber, silicon rubber etc., which then bear the gas-retaining coating.

Further variants or features relate to the
application in the form of tiles, slabs etc. with the desired surface properties.
application of flexible areal elements.
application by reversible or irreversible adhesive bonding.
coating of vessel walls and surfaces—entirely or in part.
use of metallic surface structures.
use of surfaces with continuous air layer.

use of surfaces which form, build up or retain only a regular or irregular pattern of gas pockets or gas bubbles under liquid.

use of said pattern of gas pockets or gas bubbles under liquid as a form of "ball bearing with balls composed of gas or air"—for mechanical guidance and/or for friction reduction.

use as a coating in pipes or in chemical reaction vessels.

Device for retaining an air layer under water or generally a gas layer under liquid, characterized in that the gas layer is not of continuous form but is in the form of an array of small gas bubbles at predefined points on the surface, in a preferred embodiment configured such that the gas bubbles form at predefined points on the surface which, by topographical structure and/or by the chemical functionalization of the surface, exhibit preference, in terms of energy, for the stabilization of the gas bubbles, wherein, in a preferred variant of the method, nucleation centers are formed at the points at which the gas bubbles are intended to form and the nucleation centers are characterized by the fact that—for example by way of a point of increased topographical roughness or chemical inhomogeneity of the surface—they locally decrease, at a defined location, the activation energy for forming a gas bubble.

The retention of a gas layer under liquids, for example under water, is of great technical interest. There is great usage potential for such surfaces for example in the field of ship coatings, inter alia for friction reduction and for the attainment of antifouling effects.

Such surfaces have already been produced on a laboratory scale. Among others, the *Salvinia*, effect, hierarchical structuring based on the example of *Notonecta*, and shark skin and dolphin skin effects have been implemented successfully.

The problem however consists in that
(i) the air escapes at the edges of the coating, and
(ii) in the case of extensive surfaces covered with gas layers, considerable pressure differences often exist between different points of the layer. An example is a vertical wall under water. Owing to the hydrostatic pressure, which increases linearly with water depth, the different points of the surface are subjected to different static pressure. If the surface is equipped with a gas-retaining layer and is thus covered by a gas layer under liquid, the gas is forced from regions of high pressure to regions of low pressure. A gas layer of homogeneous thickness is thus not formed, and—even more seriously—the gas layer in the zones of relatively high pressure will ultimately escape.
(iii) A corresponding problem also exists if the pressure gradients in the layer are not pressure gradients based on the hydrostatic pressure but are pressure gradients based on dynamic pressure differences for example owing to different flow speeds of the surrounding liquid at different locations on the surface.
(iv) The problem also consists in the reversible, also retroactive, inexpensive application of partially complex surface structures.
(v) There is also a desire for a simple means for realizing regeneration or—ideally—self-regeneration of the air layer.

In the method according to the invention and the device according to the invention, instead of a continuous air layer or compartments of air layers, use is made of an arrangement of individual air bubbles which preferably form at desired locations in a manner induced by surface structures. For this purpose, a device for retaining an air layer under water or generally a gas layer under liquid is produced and used, characterized in that the gas layer is not of continuous form but is in the form of an array of small gas bubbles at predefined points on the surface, in a preferred embodiment configured such that the gas bubbles form at predefined points on the surface which, by topographical structure and/or by the chemical functionalization of the surface, exhibit preference, in terms of energy, for the stabilization of the gas bubbles, wherein, in a preferred variant of the method, nucleation centers are formed at the points at which the gas bubbles are intended to form and the nucleation centers are characterized by the fact that—for example by way of a point of increased topographical roughness or chemical inhomogeneity of the surface—they locally decrease, at a defined location, the activation energy for forming a gas bubble.

In one variant of the stated device, use is made of areal elements (which are the subject of an invention filed in parallel) which have the above-stated surface properties and which can be applied to the surface, for example the outside of ships or the inside of pipelines, even retroactively, for example by adhesive bonding.

Further variants or features relate to the
application in the form of tiles, slabs etc. with the desired surface properties.
application of flexible areal elements.
application by reversible or irreversible adhesive bonding.
coating of ship surfaces—entirely or in part.
use of metallic surface structures.
use of surfaces with continuous air layer.
use of surfaces which form, build up or retain only a regular or irregular pattern of gas pockets or gas bubbles under liquid.
use of said pattern of gas pockets or gas bubbles under liquid as a form of "ball bearing with balls composed of gas or air"—for mechanical guidance and/or for friction reduction.
use as a coating on ships, in flow ducts, in pipes or in chemical reaction vessels.

Device for retaining an air layer under water or generally a gas layer under liquid, characterized in that the gas layer under liquid is formed autonomously, that is to say there is no need to introduce an air layer under water, instead the continuous or discontinuous gas layer (the latter being in the form of gas bubbles on surfaces) forming of its own accord, for example through utilization of gas molecules dissolved in the liquid or evaporation of the liquid under negative pressure,
characterized in that, by topographical and/or chemical structuring, regions are produced in which the ingress of liquid would expend such a high level of surface energy that liquid-free regions under liquid are formed of their own accord ("air pockets")—in one variant of the method, by the periodic or non-periodic arrangement, on the surface, of hairs or spikes of a particular shape, preferably of nonwetting hairs or other structures which form an open or closed "crown" which entirely or partially surrounds the gas bubble that forms The retention of a gas layer under liquids, for example under water, is of great technical interest. There is great usage potential for such surfaces for example in the field of ship coatings, inter alia for friction reduction and for the attainment of antifouling effects.

Such surfaces have already been produced on a laboratory scale. Among others, the *Salvinia*, effect, hierarchical structuring based on the example of *Notonecta*, and shark skin and dolphin skin effects have been implemented successfully.

The problem consists in that, under adverse operating conditions (wave surge, wave impact in the case of ship coatings etc.) or over relatively long periods of time, partial or complete, local or extensive gas loss occurs in places or overall.

Subsequent artificial refilling or replenishment of the gas is cumbersome, requires monitoring and requires suitable, possibly expensive apparatuses for filling and monitoring, and even a filling facility for each compartment in the case of a compartment structure of the air layer, and even a filling facility for each gas bubble in the case of a gas bubble structure.

In the method according to the invention and the device according to the invention, said problem is solved in that use is made of a device for retaining an air layer under water or generally a gas layer under liquid, characterized in that the gas layer under liquid is formed autonomously, that is to say there is no need to introduce an air layer under water, instead the continuous or discontinuous gas layer (the latter being in the form of gas bubbles on surfaces) forming of its own accord, for example through utilization of gas molecules dissolved in the liquid or evaporation of the liquid under negative pressure, characterized in that, by topographical and/or chemical structuring, regions are produced in which the ingress of liquid would expend such a high level of surface energy that liquid-free regions under liquid are formed of their own accord ("air pockets")—in one variant of the method, by the periodic or non-periodic arrangement, on the surface, of hairs or spikes of a particular shape, preferably of nonwetting hairs or other structures which form an open or closed "crown" which entirely or partially surrounds the gas bubble that forms.

In one variant of the stated device, use is made of areal elements (which are the subject of an invention filed in parallel) which have the above-stated surface properties and which can be applied to the surface, for example the outside of ships or the inside of pipelines, even retroactively, for example by adhesive bonding.

Further variants or features relate to a
- combination of the above self-charging of the gas layer with additional devices for artificially refilling or replenishing the gas layer, for example capillaries, membranes, textiles etc.,
- device as described immediately above, possibly also coupled with measurement and/or control and/or regulating devices which measure and control the state of the gas layer overall or in spatially resolved fashion and automatically trigger replenishment if required.
- application in the form of tiles, slabs etc. with the desired surface properties.
- application of flexible areal elements.
- application by reversible or irreversible adhesive bonding.
- coating of ship surfaces—entirely or in part.
- use of metallic surface structures.
- use of surfaces with continuous air layer.
- use of surfaces which form, build up or retain only a regular or irregular pattern of gas pockets or gas bubbles under liquid.
- use of said pattern of gas pockets or gas bubbles under liquid as a form of "ball bearing with balls composed of gas or air"—for mechanical guidance and/or for friction reduction.
- use as a coating on ships, in flow ducts, in pipes or in chemical reaction vessels.

Device for retaining air or gas bubbles ("air pockets") under liquid, characterized in that use is made of hairs with an open or closed coronet structure or else groups of simple curved hairs directly on the surface such that the hairs, as a group, form a coronet, that is to say an open "vessel" in which the air or gas bubble is enclosed and securely retained under liquid even in the flowing medium or counter to the action of buoyancy—in a preferred embodiment, with the hair surfaces being equipped with a hydrophobic or superhydrophobic surface or surface coating, likewise preferably with elastic hairs which, under mechanical load, can deform together with the gas bubble, furthermore—in one variant of the invention—use of the gas bubbles in the coronet as nucleation centers for the autonomous or artificial refilling of a gas layer proceeding from gas bubbles in the coronet.

The retention of a gas layer under liquids, for example under water, is of great technical interest. There is great usage potential for such surfaces for example in the field of ship coatings, inter alia for friction reduction and for the attainment of antifouling effects.

Such surfaces have already been produced on a laboratory scale. Among others, the *Salvinia*, effect, hierarchical structuring based on the example of *Notonecta*, and shark skin and dolphin skin effects have been implemented successfully.

A problem consists in the controlled nucleation and retention of individual gas bubbles at a defined location, and the secure retention thereof with respect to external forces.

In the method according to the invention and the device according to the invention, a device for retaining air or gas bubbles ("air pockets") under liquid is produced and used, characterized in that use is made of hairs with an open or closed coronet structure or else groups of simple curved hairs directly on the surface such that the hairs, as a group, form a coronet, that is to say an open "vessel" in which the air or gas bubble is enclosed and securely retained under liquid even in the flowing medium or counter to the action of buoyancy—in a preferred embodiment, with the hair surfaces being equipped with a hydrophobic or superhydrophobic surface or surface coating, likewise preferably with elastic hairs which, under mechanical load, can deform together with the gas bubble, furthermore—in one variant of the invention—use of the gas bubbles in the coronet as nucleation centers for the autonomous or artificial refilling of a gas layer proceeding from gas bubbles in the coronet.

In one variant of the method, use is made of open or closed coronets which are situated not directly on the surface but which are situated on the end of a stem of a multi-core or forked stem (open or closed "eggbeater structure").

In a further variant of the stated device, use is made of areal elements (which are the subject of an invention filed in parallel) which have the above-stated surface properties and which can be applied to the surface, for example the outside of ships or the inside of pipelines, even retroactively, for example by adhesive bonding.

Further variants or features relate to the
- use of elastic hairs or structures for forming the coronet structure.
- use of hairs or coronets which have entirely or partially hydrophobic or superhydrophobic surfaces or are entirely or partially provided with a coating which is hydrophobic or superhydrophobic.
- use of open or closed coronet structures.
- use in combination with a gas-retaining underply layer ("aerenchyma").
- production of the coronet structures from polymers, metals or ceramic materials.
- production of the coronet structures by molding of master structures and/or by three-dimensional laser structuring or production of master structures by three-dimensional laser structuring or laser lithography and subsequent molding of said structures without or after an inversion process having taken place.

combination of the above self-charging of the gas layer with additional devices for artificially refilling or replenishing the gas layer, for example capillaries, membranes, textiles etc., device as described immediately above, possibly also coupled with measurement and/or control and/or regulating devices which measure and control the state of the gas layer overall or in spatially resolved fashion and automatically trigger replenishment if required.

application in the form of tiles, slabs etc. with the desired surface properties.

application of flexible areal elements.

application by reversible or irreversible adhesive bonding.

coating of ship surfaces—entirely or in part.

use of metallic surface structures.

use of surfaces with continuous air layer.

use of surfaces which form, build up or retain only a regular or irregular pattern of gas pockets or gas bubbles under liquid.

use of said pattern of gas pockets or gas bubbles under liquid as a form of "ball bearing with balls composed of gas or air"—for mechanical guidance and/or for friction reduction.

use as a coating on ships, in flow ducts, in pipes or in chemical reaction vessels.

Device for retaining an air layer under water or generally a gas layer under liquid, characterized in that, under the layer that retains the air, based on the example of *Notonecta glauca*, or *Salvinia molesta*, for example, there is situated a porous, microporous or nanoporous, hydrophobic or superhydrophobic layer which can act as an air store in the event of mechanical load on the air layer, such that the air layer is not released but is forced into the air storage layer and, after the load ceases to act, is partially or entirely released again.

The retention of a gas layer under liquids, for example under water, is of great technical interest. There is great usage potential for such surfaces for example in the field of ship coatings, inter alia for friction reduction and for the attainment of antifouling effects.

Such surfaces have already been produced on a laboratory scale. Among others, the *Salvinia*, effect, hierarchical structuring based on the example of *Notonecta*, and shark skin and dolphin skin effects have been implemented successfully.

The problem consists in that, under adverse operating conditions (wave surge, wave impact in the case of ship coatings etc.) or over relatively long periods of time, partial or complete, local or extensive gas loss occurs in places or overall.

Subsequent artificial refilling or replenishment of the gas is cumbersome, requires monitoring and requires suitable, possibly expensive apparatuses for filling and monitoring, and even a filling facility for each compartment in the case of a compartment structure of the air layer, and even a filling facility for each gas bubble in the case of a gas bubble structure.

In the method according to the invention and the device according to the invention, the loss of air in the event of pressure loads acting on the layer is prevented by providing protective withdrawal facilities for the air. This is achieved through the use of a device for retaining an air layer under water or generally a gas layer under liquid, characterized in that, under the layer that retains the air, based on the example of *Notonecta glauca*, or *Salvinia molesta*, for example, there is situated a porous, microporous or nanoporous, hydrophobic or superhydrophobic layer which can act as an air store in the event of mechanical load on the air layer, such that the air layer is not released but is forced into the aerenchyma and, after the load ceases to act, is released again.

In a further variant of the stated device, use is made of areal elements (which are the subject of an invention filed in parallel) which have the above-stated surface properties and which can be applied to the surface, for example the outside of ships or the inside of pipelines, even retroactively, for example by adhesive bonding.

Further variants or features relate to the use of an air storage layer in the form of a dense arrangement of fine thin hairs or wires in the form of a "pelt".

use of an air storage layer in the form of a dense arrangement of fine thin hairs or wires in the form of a felt or fibre network with disordered or preferably oriented fibres.

use of an air storage layer as described immediately above, wherein the felt or the network is constructed from textile fibers or from metal wires.

use of an air storage layer in the form of a porous, microporous or nanoporous material.

use of an air storage layer as described immediately above, wherein the porous material is a polymer or a metal or a ceramic material.

use of an air storage layer as described immediately above, wherein the porous material is a polymer blend layer from which one of the polymer components has been removed by way of a selective solvent—preferably after the layer formation process with accompanying phase separation—in this way a porous layer has been produced which then—with or without additional hydrophobization of the pore inner surfaces and/or of the layer surface—serves as an air store.

use of a precursor for the production of a metallic or ceramic layer as one of the two components and production of such a porous metallic or ceramic layer by subsequent thermal treatment.

application in the form of tiles, slabs etc. with the desired surface properties.

application of flexible areal elements.

application by reversible or irreversible adhesive bonding.

coating of ship surfaces—entirely or in part.

use of metallic surface structures.

use of surfaces with continuous air layer.

use of surfaces which form, build up or retain only a regular or irregular pattern of gas pockets or gas bubbles under liquid.

use of said pattern of gas pockets or gas bubbles under liquid as a form of "ball bearing with balls composed of gas or air"—for mechanical guidance and/or for friction reduction.

use as a coating on ships, in flow ducts, in pipes or in chemical reaction vessels.

Ball bearing composed of air or gas balls: reduction of friction of surfaces under liquid by coating or partial coating with an arrangement of gas bubbles, preferably in "air pockets", niches or clasping means which are preferred from an energy aspect and which are pinned against detachment and which may be situated directly on the surface but which themselves may in turn be situated on the end of a hair or of a rod or miniature leaf spring or other holding means, and the formation of rotary, antifriction and plain bearings under liquid from gas balls of said type, wherein the pinned gas balls perform the function of the balls in conventional ball bearings—with the advantages of the self-recharging, the freedom from wear and thus the unlimited service life with regard to mechanical abrasion, and with additional advantages with regard to the freedom from abraded particles (must be held in suspension, lead to further mechanical wear, can be deposited and form solid sediments which can limit the service life of mechanical moving components) and freedom from lubricants (oils etc. age, must be changed, are poisonous and are incompatible with living organisms, and must be disposed of).

The development of bearings, for example of rolling, antifriction and plain bearings, which have a long service life, low wear and low friction and in which, in particular, adhesive friction upon start-up and bearing damage during long standstill periods are eliminated, is a technical challenge. Magnetic bearings are expensive and cannot be used under all ambient conditions.

In particular under liquids, above all also if these are corrosive liquids (such as salt water) or chemically aggressive liquids (acids, brines, oxidants), a real technical problem exists.

In the method according to the invention and the device according to the invention, the problem is solved through the use of ball bearings, antifriction and plain bearings composed of air or gas bubbles and of arrangements of such balls (for plain bearings, for example of planar surfaces which are coated with such balls composed of gas under liquid (gas bubbles)): a reduction in friction of surfaces under liquid is achieved by coating or partial coating with an arrangement of gas bubbles, preferably in "air pockets", niches or clasping means which are preferred from an energy aspect and which are pinned against detachment and which may be situated directly on the surface but which themselves may also in turn be situated on the end of a hair or of a rod or miniature leaf spring or other holding means, and the formation of rotary, antifriction and plain bearings under liquid from gas balls of said type, wherein the pinned gas balls perform the function of the balls in conventional ball bearings—with the advantages of the self-recharging, the freedom from wear and thus the quasi-unlimited service life with regard to mechanical abrasion, and with additional advantages with regard to the freedom from abraded particles (must be held in suspension, lead to further mechanical wear, can be deposited and form solid sediments which can limit the service life of mechanical moving components) and freedom from lubricants (oils etc. undergo aging, must be changed, are poisonous and are incompatible with living organisms, and must be disposed of).

Further variants or features relate to the
  use of a persistent gas layer or of compartments composed of gas layers which are retained on the surface, instead of the individual gas balls (gas bubbles).
  use of positionally fixed, pinned gas bubbles.
  use of non-positionally fixed or non-pinned gas bubbles which can move in a defined environment, similarly to the balls of "normal" ball bearings, movable in and possibly with its ball cage.
  combination with facilities for charging the gas layer or the gas balls ("replenishing"), in the event of a loss of gas, by means of additional devices for artificially refilling or replenishing the gas layer, for example capillaries, membranes, textiles, etc.,
  device as described immediately above, possibly also coupled with measurement and/or control and/or regulating devices which measure and control the state of the gas layer overall or in spatially resolved fashion and automatically trigger replenishment if required.
  application in the form of tiles, slabs etc. with the desired surface properties.
  application of flexible areal elements.
  application by reversible or irreversible adhesive bonding.
  coating of ship surfaces—entirely or in part.
  use of metallic surface structures.
  use of surfaces with continuous air layer.
  use of surfaces which form, build up or retain only a regular or irregular pattern of gas pockets or gas bubbles under liquid.
  use of said pattern of gas pockets or gas bubbles under liquid as a form of "ball bearing with balls composed of gas or air"—for mechanical guidance and/or for friction reduction.
  use as a coating on ships, in flow ducts, in pipes or in chemical reaction vessels.

Chemical reaction vessels, pipes and conduits with walls composed of air: chemical reaction vessels of stable form for reactions of liquids or of liquids with included solid components and particles, characterized in that the reaction vessel walls—which in a preferred design variant are dimensionally stable and dimensionally defined—are composed of an air or gas layer generated by way of a solid vessel wall coated with structures for gas retention under liquid, and the use of such devices for the execution of chemical reactions and physical and chemical processes, in one variant of the method with additional utilization of the gas layer for the feed of reaction reagents and for the discharge of reaction products, in a further variant of the method for utilizing the gas layer for cleaning and flushing with gas, for monitoring the pressure in the reaction vessel, for the discharge or feed of heat energy, or for a combination of the stated things.

The provision of suitable reaction vessels for reactions under extreme conditions, high temperatures or with chemically reactive liquid media places high demands on the vessel walls.

A further problem is that, after coming into contact with a liquid, the vessel walls must often be cleaned in a cumbersome manner before another liquid can be introduced into the vessel or passed through the line. This applies in particular in the case of vessels for foodstuffs. After the transportation of toxic liquids into a vessel or a pipeline, this must be carefully cleaned before being filled with liquid foodstuffs such as beverages, milk etc.

In the method according to the invention and the device according to the invention, the stated problems are solved in that the vessel walls do not come into contact with the liquid and, therefore, it is also not possible for liquid residues to remain on the vessel walls, and it is also not possible for chemical reactions to take place between the liquid and the vessel walls by virtue of the fact that a persistent gas layer is introduced between the liquid and the vessel wall. In effect, use is made of "chemical reaction vessels, pipes and conduits with walls composed of air": Use is made of chemical reaction vessels of stable form for reactions of liquids or of liquids with included solid components and particles, characterized in that the reaction vessel walls—which in a preferred design variant are dimensionally stable and dimensionally defined—are composed of an air or gas layer generated by way of a solid vessel wall coated with structures for gas retention under liquid.

Also claimed is the use of such devices for the execution of chemical reactions and physical and chemical processes, in one variant of the method with additional utilization of the gas layer for the feed of reaction reagents and for the discharge of reaction products.

A further variant of the method involves utilizing the gas layer for cleaning and flushing with gas, for monitoring the pressure in the reaction vessel, for the discharge or feed of heat energy, or for a combination of the stated things.

Further variants or features relate to the
- use of a persistent gas layer or of compartments composed of gas layers which are retained on the surface, instead of the individual gas balls (gas bubbles).
- use of positionally fixed, pinned gas bubbles.
- use of non-positionally fixed or non-pinned gas bubbles which can move in a defined environment, similarly to the balls of "normal" ball bearings, movable in and possibly with its ball cage.
- combination with facilities for charging the gas layer or the gas balls ("replenishing"), in the event of a loss of gas, by means of additional devices for artificially refilling or replenishing the gas layer, for example capillaries, membranes, textiles, etc.,
- device as described immediately above, possibly also coupled with measurement and/or control and/or regulating devices which measure and control the state of the gas layer overall or in spatially resolved fashion and automatically trigger replenishment if required.
- application in the form of tiles, slabs etc. with the desired surface properties.
- application of flexible areal elements.
- application by reversible or irreversible adhesive bonding.
- coating of inner and outer surfaces—entirely or in part.
- use of metallic surface structures.
- use of surfaces with continuous air layer.
- use of surfaces which form, build up or retain only a regular or irregular pattern of gas pockets or gas bubbles under liquid.
- use of said pattern of gas pockets or gas bubbles under liquid as a form of "ball bearing with balls composed of gas or air"—for mechanical guidance and/or for friction reduction.
- use as a coating on ships, in flow ducts, in pipes or in chemical reaction vessels.

Underwater air-retaining structured surfaces with air retention in the form of "air layers", "air compartments" and "air pockets": continuous air layers, air compartments of limited areal extent and local air pockets and bubbles and the variant of irregular structuring with continuous transition between these cases.

Gas layers on surfaces under liquid are of great technological interest for friction reduction in the case of ships and in pipelines and for protection of the surface against fogging, (bio)fouling, corrosion and chemical attack.

By means of suitable surface structuring, it is possible for a layer of gas or of gas bubbles, which adheres to the surface, to be entrained under liquid. The problem is that of finding suitable surface structures which, even in the event of pressure fluctuations, retain the continuous or discontinuous gas layer under liquid permanently or at least for certain periods of time.

Said problems are solved by means of a hydrophobic or superhydrophobic surface which is topographically structured such that the gas layer or gas bubbles are retained, and in a preferred variant additionally impeded from escaping by hydrophilic pins, and/or, for the gas bubbles, certain topographically pre-shaped regions, "air pockets", in the surface structure are created which permit stable storage of small gas volumes under liquid in stable fashion. Here, use may be made of rough surfaces even on the millimeter scale or micrometer scale or nanometer scale, or a combination of several of said length scales, in order thereby to realize superhydrophobic characteristics by way of the nanoroughness and to realize the air pockets by way of the roughness in the millimeter and micrometer range, said air pockets preferably having typical dimensions in the range between 10 μm and 5 mm, particularly preferably between 0.1 mm and 3 mm. Said air pockets may then likewise, in a preferred variant, have hydrophilic pinning centers on their otherwise hydrophobic or superhydrophobic surface in order to securely retain the air-water interface and thus prevent the escape of gas bubbles.

Here, the pinning may also take place on multiple structuring planes (hierarchical pinning or two-level or multi-level pinning effect) or on irregularly structured surfaces even with a continuous hierarchy (which corresponds to an infinite number of hierarchical planes). Here, in the event of the pinning taking place in the upper hierarchical planes, extensive air-coated regions can be formed, with even continuous, coherent air layers being formed above a so-called percolation threshold; only when air escapes somewhere and the water reaches the lower hierarchical planes are spatially mutually separate air volumes formed on the surface ("compartment structure") until, in the event of a yet further ingress of water, for example owing to very high pressure fluctuations, yet more air is lost and finally only the air pockets remain as a final air reserve. Said air pockets then have a triple function:

- they serve as a final air reservoir that can be eliminated only with difficulty, as an "emergency reserve of air".
- They nevertheless protect a major part, typically 60% to 98% of the entire surface, against oxidation, chemical attack or (bio)fouling and have a friction-reducing action, and above all:
- They act as nuclei for the restoration of the air layer, both in the case of active refilling of the gas layer ("replenishing") and also in the self-regeneration process of the air layer.

This targeted structuring on multiple planes, or length and possibly also height scales, and—in a preferred variant—additionally hierarchical pinning, exhibits the said three stages of air retention in the simplest case:

1. Continuous air layer, borne and supported by only individual supporting structures (hairs, pillars, elevations) which may be hydrophobic or superhydrophobic with or without hydrophilic pinning centers (the latter, if present, preferably on the upper end of said supporting structures). The friction between liquid and solid body is thereby massively reduced, in part to below 5% of the value without air layer. However, in this state (which is virtually ideal for all other technical properties), the susceptibility to air loss in the event of pressure fluctuations is high. The activation barriers with regard to air loss—for example by escape of gas bubbles—are relatively low with regard to the force required per unit area or with regard to the energy required per unit area.
2. In the event of a loss of air having occurred, stage 1, (state as described immediately above) transitions into stage 2: Relatively large, coherent air-covered regions of the surface under liquid are formed, but the percolation threshold for continuous air layers is undershot. The individual air-covered surface regions are delimited by partitions or by non-air-coated surface regions which are in contact with water and which generally block an exchange of gas between the individual air islands or compartments. In this state, the friction reduction is still significant but is considerably reduced in relation to state 1. The protection of the surfaces against contact with the water or the liquid is still substantially completely or at least for the most part maintained (typically, only at most 2% to 10% of the overall surface is in contact with the water). The activation threshold required for the detachment of air from the layer, or generally gas from the layer, is significantly higher than in stage 1.

3. In the event of a yet further loss of gas, for example owing to very intense pressure fluctuations, the final remaining stage is stage 3, in which the surface stores only small air volumes in hydrophobic niches, the so-called air pockets. These, too, may have hydrophilic pinning centers on their side facing toward the water. The friction-reducing action of the air layer is significantly weakened in this state in relation to stage 1, and in the extreme case no longer exists. Nevertheless, even in stage 3, depending on the topographical configuration, a considerable reduction in the contact area between the solid body surface of the immersed solid body and the water is obtained, usually by more than a factor of 10, that is to say only less than 10% of the surface is in direct contact with the water, or more generally the liquid, in relation to the state without gas-filled "air pockets".

The air may self-evidently be replaced, very generally, by any desired gas. The water may also be substituted by any other desired liquid. "Hydrophobic or superhydrophobic" should then be replaced by "nonwetting or super-nonwetting with regard to said liquid" (defined, very analogously to hydrophobic and superhydrophobic, by way of the corresponding contact angle), and the hydrophilic pins should be replaced by pins which are "liquidophilic", that is to say wetting, with regard to said liquid. Here, relatively small differences are sufficient: The "hydrophilic pins" need not imperatively be actually hydrophilic in the sense of the textbook definition; in some cases, it is sufficient for these to merely be more wetting than the other hydrophobic (or generally for any desired liquid: "liquidophobic") surface.

In variants of the embodiment, it may also be provided either that the three hierarchical planes of the structuring are not provided (with only one plane being provided) or that two planes or all three planes are provided, or, instead of a regular or quasi-regular structured surface, a randomly structured surface may be provided which has a certain roughness and which has relatively small or relatively large pinning centers at certain locations and the natural depressions of which serve as air pockets. Likewise suitable as surfaces of a particular roughness, of course, are porous surfaces in which the pores situated on the surface can serve as air pockets.

One particular variant of a surface of said type is fibers or textile fibers which, owing to a surface configured as described above, can retain a continuous or discontinuous layer of air under water. Everything is as described immediately above, with the only exception being that the described structured surface is now the surface of a fiber. This, too, may again be structured—like the surfaces already described above by regular or irregular topographical structuring or
 by regular or irregular chemical structuring (that is to say a spatially dependent chemical or biochemical surface functionalization) or
 by surface roughness or
 by surface porosity or by a combination of the stated forms, and may or may not have hydrophilic pinning centers. With regard to the fibers that retain gas on their surface under liquid, it is of interest that it is possible from these to construct or produce textiles, fabrics, meshes, mats, strands, cords, felts, bathing wear (swimming trunks, swimsuit etc.) etc. that retain gas or their surface under liquid. It is likewise conceivable for ships, boats, water sport devices (including surfboards etc.), buoys, drilling platforms, measurement stations, measurement appliances, water-exposed components of offshore wind farms, other structures in water etc. to be coated with such air-retaining textiles, for example in order to achieve friction reduction, antifouling action or corrosion prevention.

Uses of the Salvinia effect:
Contactless vessels for highly reactive liquids.
Liquids surrounded by a gas cushion of a reaction partner to which the gas or a constituent of the gas or in the form of fine droplets or of fine particles can be fed.
Use of the air cushion for thermal insulation.
Use of the air cushion for friction reduction.
Use of the air cushion to attain an antifouling effect.
Use of the air cushion for preventing biofilm formation.
The fouling of the hairs and of the substrate surface itself could be prevented by coating with bactericides, fungicides, nanosilver, nanocopper or silver-containing and copper-containing components.
Use of the air cushion for electrical insulation and galvanic separation, in particular in the case of electrolytes.

Durable attainment of the *Salvinia*, effect by rechargeable air layers:
Recharging of the air layer by means of pumps or pressurized gas bottles via fine nozzles or via a gas-permeable surface between the individual hairs.
Recharging of the air layer by galvanic, catalytic, photocatalytic or galvanocatalytic decomposition of the liquid medium (for example water).
Recharging of the air layer by way of dissolved gas components in the liquid, by virtue of the surface energy of the ingressing water being increased to such an extent that it is held away and thus the sum of the partial pressures of all of the gases and liquids in the liquid medium is equal to the gas pressure in the *Salvinia*, gas layer—which can mean that this is less than the hydrostatic pressure in the liquid,
and targeted utilization of this effect in order to increase the activation energy for the formation of gas bubbles: the liquid medium is still "drawn" to the surface of the leaf hairs owing to the negative pressure in the gas layer.

Generation of air layers with and without *Salvinia* effect:
Use inter alia for:
Air retention.
Friction reduction.
Buoyancy.
Antifouling.
Corrosion prevention.
Adhesion prevention—production of anti-adhesive surfaces by "coating with air" in the described manner.
In combination with auto-reloading or active reloading of the air layer, it would be possible here to construct a highly efficient system for friction reduction.
Further friction reduction would be realized by non-polar Teflon gliders on the end of the hairs.
By making the angle of inclination of the upper ends of the hairs shallower, the derivative of the wetting energy with respect to the penetration depth of the water into the hair layer, and thus the repelling force with which the liquid is repelled when it ingresses, is massively increased.

The elasticity of the angled hairs should furthermore, through suitable selection of the spring constant, ensure that the hair bends rather than being wetted by the liquid.

Figure 27:
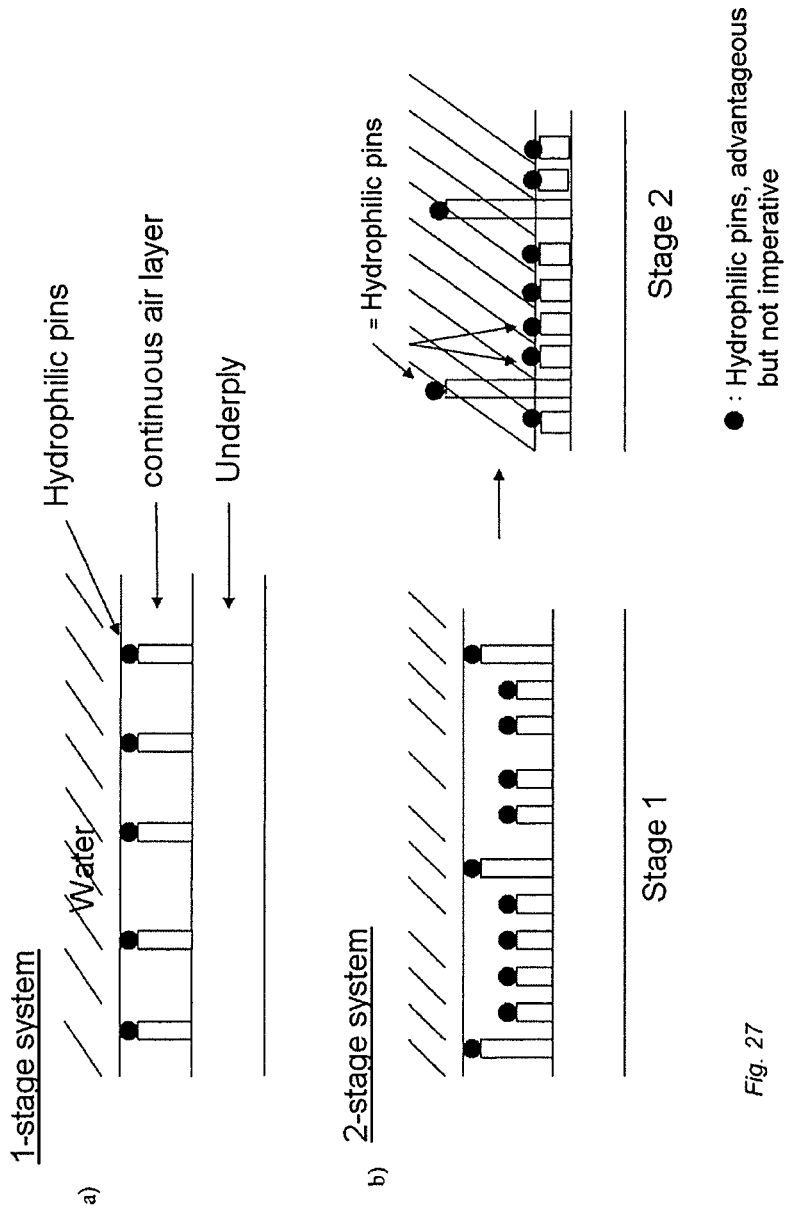
FIG. 27: shows a gas-retaining layer as a single-stage system and as a two-stage system.

FIG. 27a, shows a gas-retaining layer with a single-stage system of projections, wherein all of the projections have substantially the same longitudinal extent.

FIG. 27b, shows a gas-retaining layer with a two-stage system of projections, wherein projections are divided into short and long projections.

Figure 28:
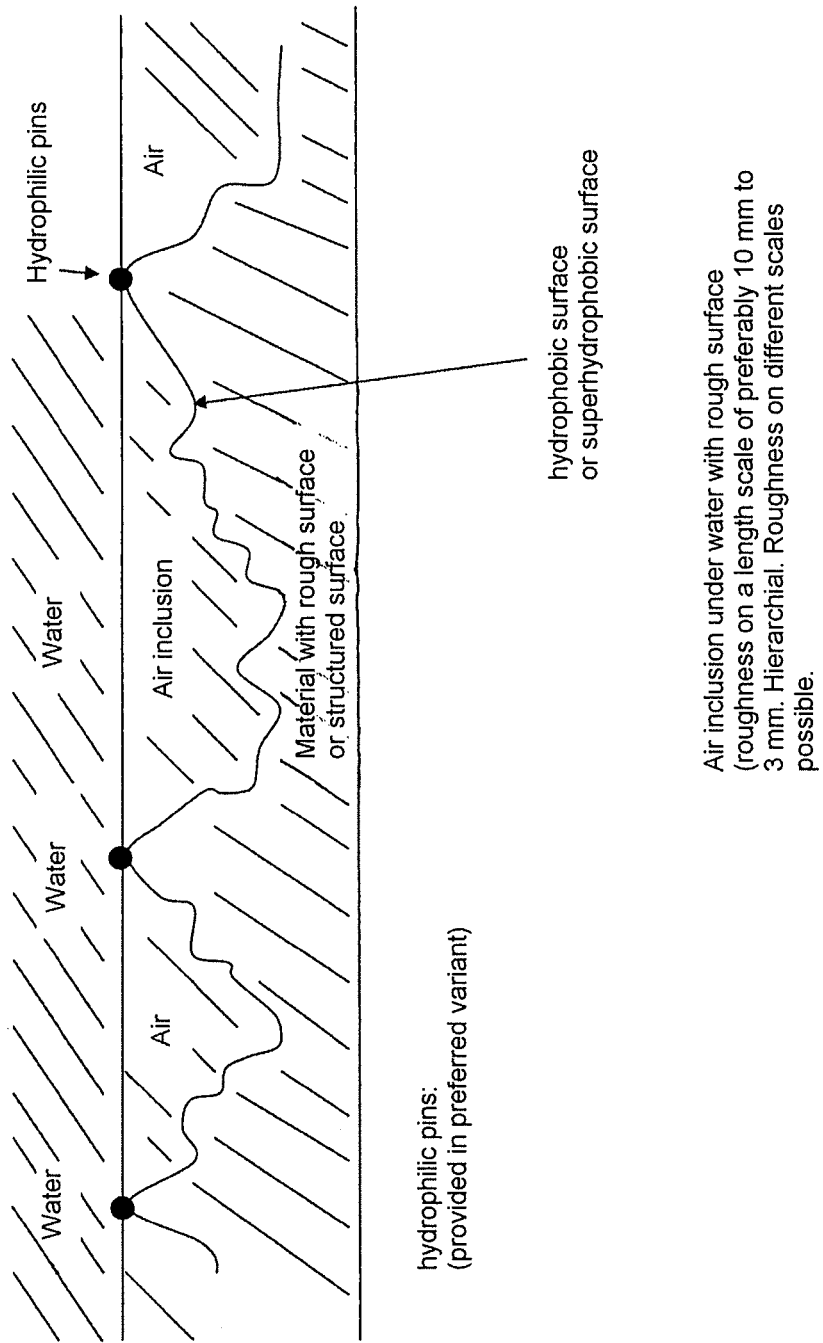
FIG. 28: shows a gas-retaining layer which is formed by a rough surface.

FIG. 28 shows a gas-retaining layer which is formed by a rough surface, wherein the roughness on surface may have a length scale from approximately 10 µm to approximately 3 mm.

FIG. 29a, shows a gas-retaining layer with a rough surface which is in the form of a single-stage system.

FIG. 29b, shows a gas-retaining layer with a rough surface which is in the form of a two-stage system. FIG. 29c, shows a gas-retaining layer with a rough surface which is in the form of a three-stage system.

FIG. 30a, shows a gas-retaining layer which is formed on a filiform element. FIG. 30b, shows a filiform or fiber-like element with a gas-retaining layer which is in the form of a two-stage system.

Figure 31:
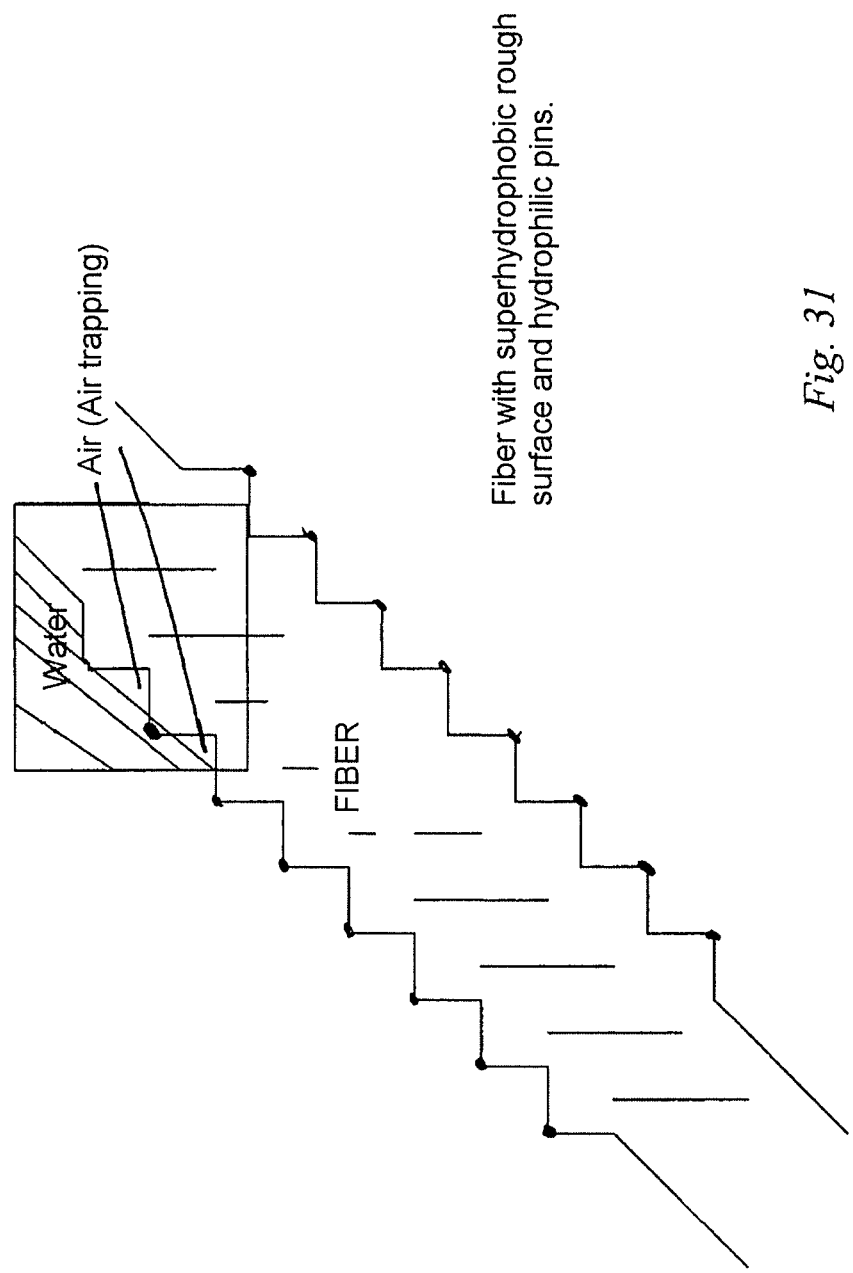
FIG. 31: shows a gas-retaining layer which is formed on a filiform element.

FIG. 31 shows a gas-retaining layer which is formed on a filiform element and has a superhydrophobic surface on which hydrophilic points or pins are optionally formed.

Figure 32:
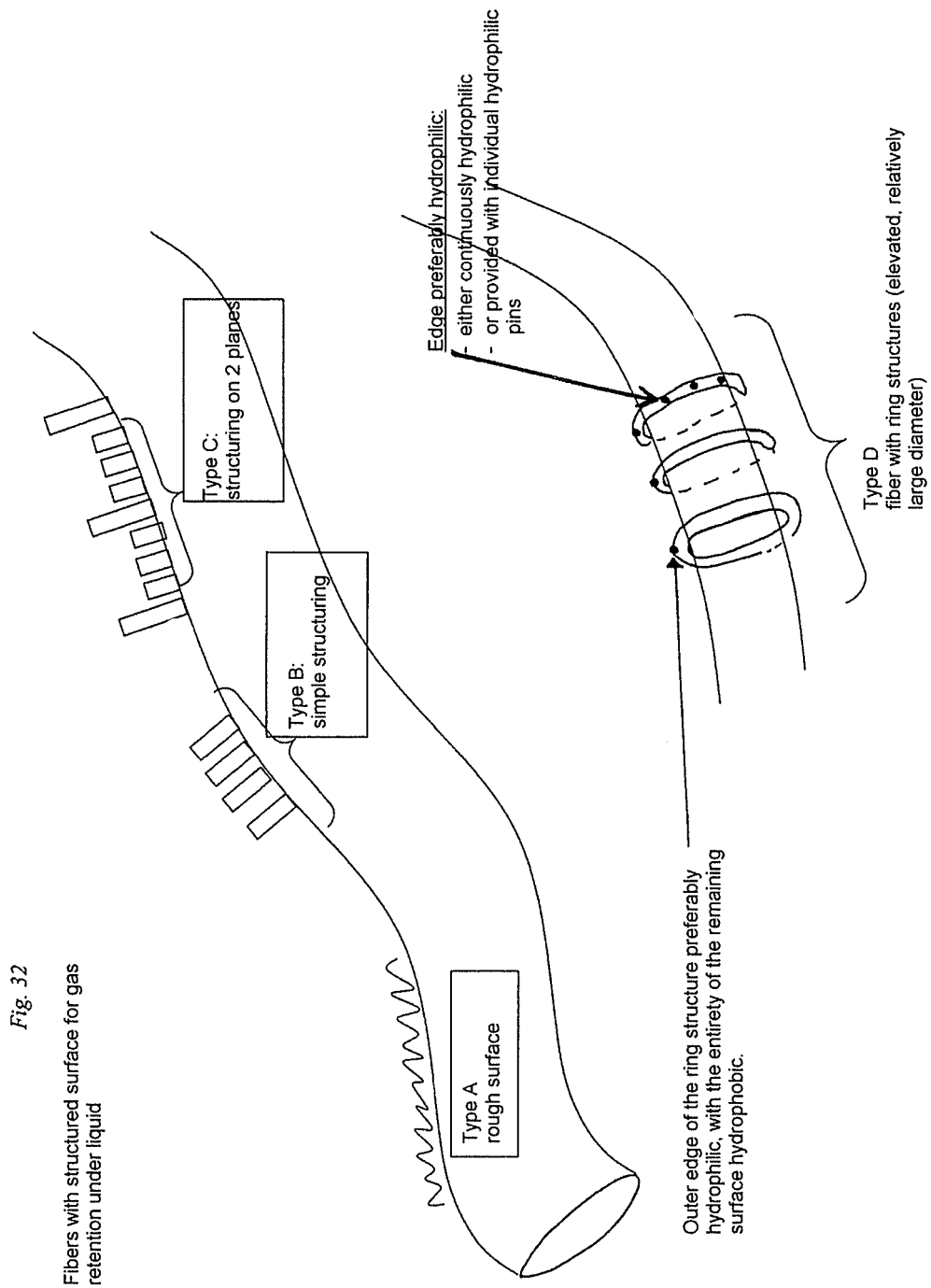
FIG. 32: shows a gas-retaining layer which is formed on a filiform element.

FIG. 32 shows a gas-retaining layer which is formed on a filiform element, wherein different surface configurations are shown.

Figure 33:
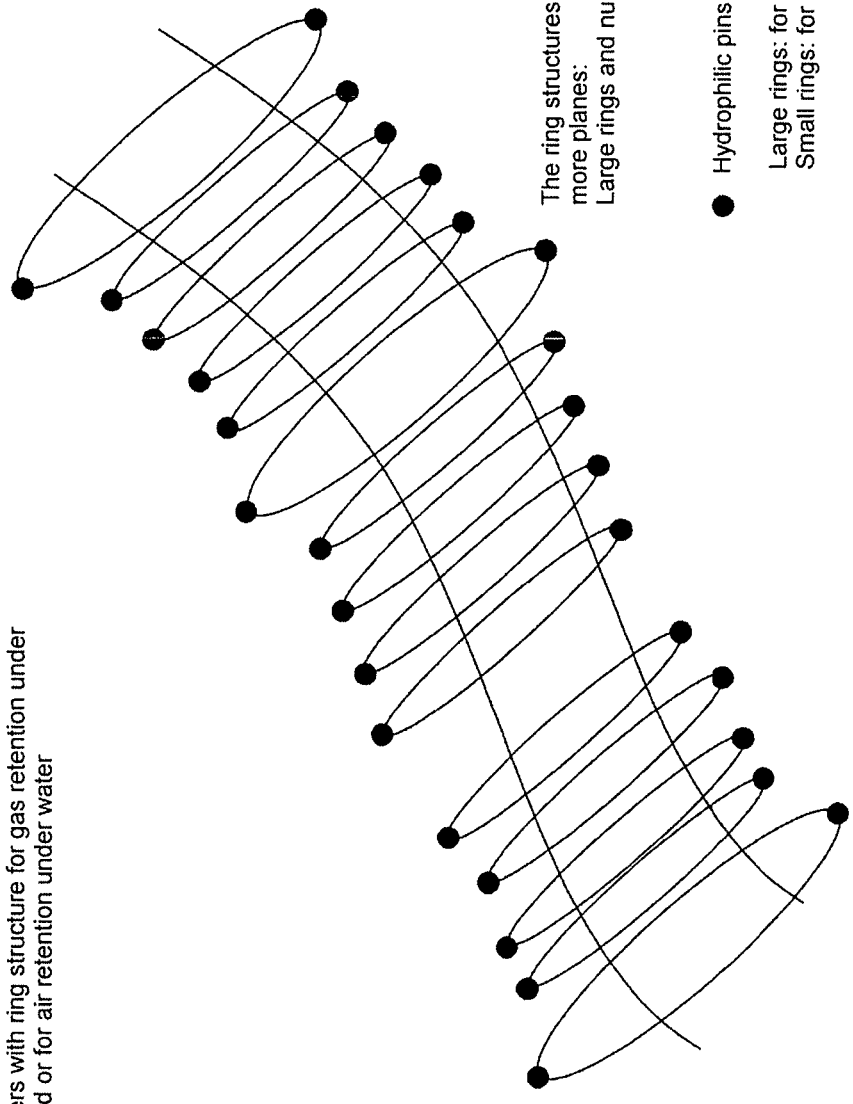
FIG. 33: shows a gas-retaining layer which is formed on a filiform element.

FIG. 33 shows a gas-retaining layer which is formed on a filiform element, wherein the gas-retaining layer has a ring structure.

LIST OF REFERENCE SIGNS

2 Wall
4 Liquid
5 Gas
6 Surface covering
10 Gas-retaining layer
10c, Base of the gas-retaining layer 10
12 Gas-permeable ply
14 Gas feed device
16 Gas duct
18 Gas source
20 Valve
22 Regulating device
24 Sensor device
26 Protruding element
27 Protruding element
28 Gas discharge device
30 Depression
32 Opening of the depression 30
34 Hydrophobic coating of the depression 30
36 Surface coating
38 Rough surface
40 Fiber
42 Partition
44 Sub-region of the gas-retaining layer 10
A Gas discharge direction
L Longitudinal direction

What is claimed:

1. A method for protecting a body that is placed in contact with a liquid, said method comprising arranging a gas-retaining layer on at least a portion of a body that can be immersed in a liquid or wetted by a liquid and which is in contact by way of a liquid-facing side with a liquid when the body is immersed in/wetted by the liquid, wherein the gas-retaining layer has on the liquid-facing side recesses and/or protruding elements whose surfaces are hydrophobic at least regionally, and a gas layer which is retained in the immersed/wetted region of the gas-retaining layer separates the liquid and the immersed/wetted region of the body from one another at least regionally, wherein the gas-retaining layer is divided into a multiplicity of sub-regions by fluid-impermeable partitions.

2. The method according to claim 1, wherein a corrosion prevention coating and/or an antifouling coating is arranged between the gas-retaining layer and a wall of the body and wherein the gas-retaining layer separates the corrosion prevention coating and/or the antifouling coating from the liquid at least regionally.

3. The method according to claim 1, wherein the fluid-impermeable partitions, which are of equal length, are arranged so as to form hexagonal sub-regions, or wherein the fluid-impermeable partitions are arranged so as to form elongate honeycomb-shaped or hexagonal sub-regions.

4. The method according to claim 1, wherein the partitions are of hydrophilic form at least regionally.

5. The method according to claim 1, wherein protruding elements are present in all of the sub-regions.

6. A method for protecting a body that is placed in contact with a liquid, said method comprising:
providing a gas-retaining layer having a liquid-facing side and protruding elements on the liquid-facing side, the protruding elements having a central surface region which is hydrophilic and which is surrounded by a hydrophobic surface region of the protruding elements; and
arranging the gas-retaining layer on at least a portion of a body that can be immersed in a liquid or wetted by a liquid and which is in contact by way of the liquid-facing side with a liquid when the body is immersed in/wetted by the liquid,
wherein the gas-retaining layer has optionally recesses whose surfaces are hydrophobic at least regionally, and a gas layer which is retained in the immersed/wetted region of the gas-retaining layer separates the liquid and the immersed/wetted region of the body from one another at least regionally, wherein the protruding elements have a central surface region which is hydrophilic and which is surrounded by a hydrophobic surface region of the protruding elements.

7. The method according to claims 1 or 6, wherein the gas-retaining layer is charged with gas from a body-facing side situated opposite the liquid-facing side, of the gas-retaining layer.

8. The method according to claims 1 or 6, wherein a gas-permeable layer is arranged on the body-facing side of the gas-retaining layer.

9. The method according to claim 8, wherein the gas-permeable layer is in the form of a liquid-impermeable and/or hydrophobic layer.

10. The method according to claim 8, wherein a gas feed device is connected to the gas-permeable layer such that gas can flow from a gas feed device to the gas-retaining layer through the gas-permeable layer.

11. The method according to claim 8, wherein the gas-permeable layer is in the form of a porous semipermeable membrane.

12. The method according to claim 10, wherein the gas feed device is in the form of a gas-permeable layer which is arranged on the body-facing side of the gas-permeable layer.

13. The method according to claims 1 or 6, wherein a surface structure of the gas-retaining layer (10) comprises a material selected from polymers, lacquers, ceramics, PDMS, rubber, silicon rubber and metals.

14. The method according to claim 13, wherein the gas-retaining layer is composed of an embossed plastics resin or lacquer.

15. The method according to claim 1 or 6, wherein the body is in the form of tiles, foils, balls, or walls of watercrafts, pipes and vessels.

16. The method according to claim 1 or 6 as antifouling and/or corrosion prevention and/or prevention of contamination of the liquid with poisonous substances contained on the liquid-facing side of the body and/or friction reduction.

17. A method for protecting a body that is placed in contact with a liquid, said method comprising arranging a gas-retaining layer on at least a portion of a body that can be immersed in a liquid or wetted by a liquid and which is in contact by way of a liquid-facing side with a liquid when the body is immersed in/wetted by the liquid, wherein the gas-retaining layer has on the liquid-facing side recesses and/or protruding elements whose surfaces are hydrophobic at least regionally, and a gas layer which is retained in the immersed/wetted region of the gas-retaining layer separates the liquid and the immersed/wetted region of the body from one another at least regionally, wherein the gas-retaining layer is charged with gas from the liquid-facing side of the gas-retaining layer.

18. The method according to claim 17, wherein at least one gas discharge device is provided which has a gas discharge opening at the liquid-facing side of the gas-retaining layer; and wherein a gas feed device is provided which is connected to the gas discharge device, wherein gas provided by the gas feed device flows out of the gas discharge device and is at least partially received by the gas-retaining layer.

19. The method according to claim 18, wherein the gas discharge device extends through the gas-retaining layer.

20. The method according to claim 17, wherein a gas-permeable layer is arranged on the body-facing side of the gas-retaining layer.

21. The method according to claim 20, wherein the gas-permeable layer is in the form of a liquid-impermeable and/or hydrophobic layer.

22. The method according to claim 20, wherein the gas-permeable layer is in the form of a porous semipermeable membrane.

23. The method according to claim 17, wherein the gas-retaining layer is fed with a fouling-inhibiting gas upon the onset or in the presence of biological fouling on a wall of the body.

24. The method according to claim 17, wherein a surface structure of the gas-retaining layer comprises a material selected from polymers, lacquers, ceramics, PDMS, rubber, silicon rubber and metals.

25. The method according to claim 24, wherein the gas-retaining layer is composed of an embossed plastics resin or lacquer.

26. The method according to claim 17, wherein the body is in the form of tiles, foils, balls, or walls of watercrafts, pipes and vessels.

27. The method according to claim 17, wherein the gas layer is in the form of an array of small gas bubbles at predefined points on the surface of the gas-retaining layer.

28. The method according to claim 17 as antifouling and/or corrosion prevention and/or prevention of contamination of the liquid with poisonous substances contained on the liquid-facing side of the body and/or friction reduction.

* * * * *